(12) United States Patent
Luo et al.

(10) Patent No.: US 9,809,573 B2
(45) Date of Patent: Nov. 7, 2017

(54) SUBSTITUTED PYRIDINE DERIVATIVES USEFUL AS GSK-3 INHIBITORS

(71) Applicant: BRISTOL-MYERS SQUIBB COMPANY, Princeton, NJ (US)

(72) Inventors: Guanglin Luo, Madison, CT (US); Ling Chen, Middletown, CT (US); Gene M. Dubowchik, Middlefield, CT (US); Swanee E. Jacutin-Porte, Madison, CT (US); Prasanna Sivaprakasam, Middletown, CT (US); John E. Macor, Washington Crossing, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/033,770

(22) PCT Filed: Nov. 3, 2014

(86) PCT No.: PCT/US2014/063666
§ 371 (c)(1),
(2) Date: May 2, 2016

(87) PCT Pub. No.: WO2015/069593
PCT Pub. Date: May 14, 2015

(65) Prior Publication Data
US 2016/0289210 A1    Oct. 6, 2016

Related U.S. Application Data

(60) Provisional application No. 61/900,547, filed on Nov. 6, 2013.

(51) Int. Cl.
| | | |
|---|---|---|
| *C07D 401/12* | (2006.01) | |
| *C07D 401/14* | (2006.01) | |
| *C07D 405/14* | (2006.01) | |
| *C07D 409/14* | (2006.01) | |
| *C07D 413/14* | (2006.01) | |
| *C07D 417/12* | (2006.01) | |
| *C07D 417/14* | (2006.01) | |
| *C07D 487/08* | (2006.01) | |
| *C07D 513/04* | (2006.01) | |
| *C07D 213/81* | (2006.01) | |
| *C07D 401/04* | (2006.01) | |
| *C07D 405/04* | (2006.01) | |
| *C07D 409/04* | (2006.01) | |

(Continued)

(52) U.S. Cl.
CPC ......... *C07D 401/12* (2013.01); *C07D 213/81* (2013.01); *C07D 401/04* (2013.01); *C07D 401/14* (2013.01); *C07D 405/04* (2013.01); *C07D 405/14* (2013.01); *C07D 409/04* (2013.01); *C07D 409/14* (2013.01); *C07D 413/04* (2013.01); *C07D 413/14* (2013.01); *C07D 417/04* (2013.01); *C07D 417/12* (2013.01); *C07D 417/14* (2013.01); *C07D 487/08* (2013.01); *C07D 513/04* (2013.01)

(58) Field of Classification Search
CPC .. C07D 401/12; C07D 401/14; C07D 405/14; C07D 409/14; C07D 413/14; C07D 417/12; C07D 417/14; C07D 487/08; C07D 513/04
USPC ... 514/210.2, 217.04, 237.2, 253.13, 255.05, 514/256, 318, 341, 342, 343; 540/597; 544/124, 322, 333, 365, 405; 546/143, 546/162, 193, 269.7, 270.1, 271.1, 271.4, 546/272.1, 274.7, 275.4, 277.4, 278.1, 546/279.1
See application file for complete search history.

(56) References Cited

U.S. PATENT DOCUMENTS

| | | |
|---|---|---|
| 6,756,385 B2 | 6/2004 | Sanner et al. |
| 7,273,865 B2 | 9/2007 | Norcross |

(Continued)

FOREIGN PATENT DOCUMENTS

| | | |
|---|---|---|
| WO | WO 2009/007751 A2 | 1/2009 |
| WO | WO 2009/106209 A1 | 9/2009 |
| WO | WO 2012/116586 A1 | 9/2012 |

OTHER PUBLICATIONS

Database Registry [Online] Chemical Abstracts Service, Columbus, Ohio, Jan. 2010 (Jan. 24, 2010), retrieved from STN Database accession No. 1203041-90-0.*

(Continued)

*Primary Examiner* — Brenda Coleman
(74) *Attorney, Agent, or Firm* — James Epperson

(57) ABSTRACT

The disclosure generally relates to compounds of formula I, including their salts, as well as compositions and methods of using the compounds. The compounds are ligands, antagonists of the NR2B receptor and may be useful for the treatment of various disorders of the central nervous system.

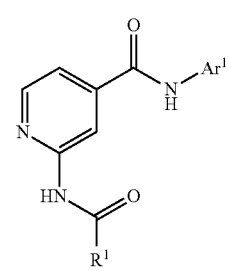

I

3 Claims, No Drawings

(51) Int. Cl.
*C07D 413/04* (2006.01)
*C07D 417/04* (2006.01)

(56) References Cited

U.S. PATENT DOCUMENTS

| | | |
|---|---|---|
| 7,531,556 B2 | 5/2009 | Green |
| 2007/0225292 A1 | 9/2007 | Amin et al. |
| 2008/0146536 A1 | 6/2008 | Cole et al. |
| 2016/0272621 A1 | 9/2016 | Luo et al. |

OTHER PUBLICATIONS

Database Registry [Online] Chemical Abstracts Service, Columbus, Ohio, Jan. 2010 (Jan. 24, 2010), retrieved from STN Database accession No. 1203187-94-3.

Helal, C.J., "Discovery and SAR of 2-amkinothiazole inhibitors of cyclin-dependent kinase 5/p25 as a potential treatment of Alzheimer's disease," Bioorganic & Medicinal Chemistry Letters, 14, pp. 5521-5525, (2004).

Yoshida, Ken-ichi, et al., "MexAB-OprM specific efflux pump inhibitors in *Pseudomonas aeruginosa*. Part 7: Highly soluble and in vivo active quaternary ammonium analogue D13-9001, a potential preclinical candidate," Bioorganic & Medicinal Chemistry, 15, pp. 7087-7097 (2007).

\* cited by examiner

SUBSTITUTED PYRIDINE DERIVATIVES USEFUL AS GSK-3 INHIBITORS

The application claims priority to Provisional Patent Application U.S. Ser. No. 61/900,547 filed Nov. 6, 2013, hereby incorporated by reference in its entirety.

BACKGROUND OF THE INVENTION

The disclosure generally relates to compounds of formula I, including their salts, as well as compositions and methods of using the compounds. The compounds inhibit GSK-3 and may be useful for the treatment of various disorders of the central nervous system.

GSK-3 is a proline directed serine/threonine kinase that carries out the phosphorylation of multiple protein substrates. Many of these proteins are involved in the regulation of numerous diverse cellular functions, including metabolism, differentiation, proliferation and apoptosis. GSK-3 is constitutively active, with its base level of activity being positively modulated by phosphorylation on Tyr216/219, depending on isoform. GSK-3 has a unique substrate selectivity profile that is distinguished by the strong preference for the presence of a phosphorylated residue optimally located four amino acids C-terminal to the site of GSK-3 phosphorylation. Most commonly, GSK-3 activity is associated with inducing a loss of substrate function, such that GSK-3 inhibition will frequently result in increased downstream substrate activity.

GSK-3 exists in two isoforms, GSK-3α (51 kDa) and GSK-3β (47 kDa), that share 84% overall identity and greater than 98% identity within their respective catalytic domains. Both primary isoforms are ubiquitously expressed, with high levels observed in the brain, particularly in the cortex and hippocampus. In most brain areas, GSK-3β is the predominant isoform. However, some studies suggest that GKS-3α and GSK-3β share very similar, if not entirely redundant functions in a number of cellular processes. The activity of GSK-3β is significantly reduced by phosphorylation at Ser9 in the N-terminal domain, most notably by protein kinase B (PKB or AKT). This inhibitory pathway has been proposed to result in neuroprotection, neurogenesis, and favorable outcomes following pharmacological treatment in various mood disorders.

Alzheimer's disease (AD) pathology is prominently associated with the formation of beta-amyloid (Aβ) plaques, soluble forms of Aβ such as Aβ1-42 that are associated with increased neuronal toxicity, and neurofibrillary tangles (NFTs). There is evidence to suggest that certain pathological mechanisms in AD, such as Aβ1-42, cause increases in GSK-3 activity in the brain. A principal consequence of this dysregulation is the hyperphosphorylation of the microtubule associated protein tau. This function of GSK-3 has been demonstrated both in cell culture, and in in vivo studies looking at tau and NFT formation. Hyper-phosphorylated tau disengages from microtubules resulting in structural destabilization of microtubules with concomitant negative effects on intracellular structures and transport mechanisms. In addition, the uncomplexed hyperphosphorylated tau assembles into paired helical filaments (PHFs) that aggregate to produce the stereotypic intracellular NFTs associated with AD. Other potential pathological consequences of over-activation of GSK-3 include neuroinflammation and neuronal apoptosis. In addition, GSK-3 has been demonstrated to be involved in mechanisms underlying memory and learning, and dysregulation of GSK-3 function may explain some of the early cognitive deficits observed in AD.

GSK-3 is also known to play a key role in glucose metabolism, and was first identified as the enzyme responsible for effecting the inhibitory phosphorylation of glycogen synthase, the result of which is to reduce the rate of conversion of glucose to glycogen, giving rise to elevated blood glucose levels. This function of GSK-3 is controlled by insulin. Binding of insulin to its receptor leads indirectly to the activation of AKT and subsequent inhibitory Ser9 phosphorylation of GSK-3.

These results and observations suggest that modulation of GSK-3 activity may be useful in the treatment of both the neuropathologic and symptomatic aspects of Alzheimer's disease, as well as other neurodegenerative diseases. These include, but are not limited to, tauopathies (for example, frontotemporal dementia, progressive supranuclear palsy, argyophilic grain disease, corticobasal degeneration, Pick's disease), Parkinson's disease, amyotrophic lateral sclerosis, stroke, Huntington's disease, peripheral neuropathies, traumatic brain injury, spinal cord trauma, and vascular dementias.

Compounds that inhibit GSK-3 may also have utility in the treatment of diabetes, inflammatory diseases such as rheumatoid arthritis and osteoarthritis, treatment-resistant depression, schizophrenia, bipolar disorder, manic depression, osteoporosis, cardioprotection, and various cancers such as gliomas, non-small cell lung cancer, pancreatic cancer, breast cancer, T- or B-cell leukemia, and multiple myeloma.

Recent reviews on the functions of GSK-3, potential therapeutic applications, and other compounds that inhibit the enzyme are listed below:

Kaidanovich-Beilin O and Woodgett J R (2011) GSK-3: functional insights from cell biology and animal models. *Front. Mol. Neurosci.* 4:40. doi: 10.3389/fnmol.2011.00040.

"Glycogen Synthase Kinase 3 (GSK-3) and Its Inhibitors", Martinez, Ana/Castro, Ana/Medina, Miguel (eds.), John Wiley and Sons (2006).

Gentles, R G, Hu, S. and Dubowchik, G M (2009) Recent Advances in the Discovery of GSK-3 Inhibitors and a Perspective on their Utility for the Treatment of Alzheimer's Disease. *Annual Reports in Medicinal Chemistry* 44, 3-26.

The invention provides technical advantages, for example, the compounds are novel inhibitors of GSK-3 and may be useful for the treatment of various disorders of the central nervous system. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, pharmaceutical compositions, and their use in treating disorders related to levels of tachykinins or serotonin or both.

One aspect of the invention is a compound of formula I

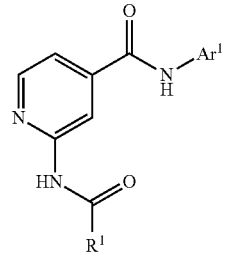

where:
R[1] is alkyl, haloalkyl, cycloalkyl, halocycloalkyl alkylcycloalkyl, dialkylcycloalkyl, phenylcycloalkyl, hydroxycycloalkyl, or ketocycloalkyl;
R[2] is hydrogen or alkyl;
R[3] is hydrogen or alkyl;
or N(R[2])(R[3]) taken together is azetidinyl, pyrrolidinyl, piperidinyl, piperazinyl, morpholinyl, or azabicycloheptane, and is substituted with 0-4 halo or alkyl substituents;
Ar[1] is 4-pyrazolyl, 5-imidazolyl, 4-thiazolyl, 3-pyridinyl, 5-pyrimidinyl, 4-pyrazinyl, 2-benzothiazolyl, 2-azabenzothiazolyl, 3-quinolinyl, 3-isoquinolinyl, or 3-tetrahydroisoquinolinyl, and is substituted with 0-3 substituents selected from cyano, halo, alkyl, haloalkyl, hydroxyalkyl, (hydroxyl)haloalkyl, alkoxyalkyl, (N(R[2])(R[3]))alkyl, benzyl, alkenyl, cycloalkyl, hydroxy, alkoxy, haloalkoxy, (hydroxyl)alkoxy, (alkoxy)alkoxy, (cycloalkyl)alkoxy, phenoxy, alkylcarbonyl, (haloalkyl)carbonyl, phenylcarbonyl, alkoxycarbonyl, carboxy, aminocarbonyl, acetamido, N(R[2])(R[3]) and Ar[2]; and
Ar[2] is phenyl, naphthalenyl, pyrrolyl, furanyl, thienyl, pyrrazolyl, isoxazolyl, isothiazolyl, imidazolyl, oxazolyl, thiazolyl, pyridinyl, pyrimidinyl, pyrazinyl, pyridazinyl, indolyl, benzofuranyl, benzothiophenyl, or quinolinyl, and is substituted with 0-3 substituents selected from the group consisting of cyano, halo, alkyl, haloalkyl, alkoxy, haloalkoxy, alkylcarbonyl, and N(R[2])(R[3]);
or a pharmaceutically acceptable salt thereof.

Another aspect of the invention is a compound of formula I where R[1] is isopropyl, haloisopropyl, cyclopropyl, halocyclopropyl, methylcyclopropyl, dimethylcyclopropyl, phenylcyclopropyl, cyclobutyl, halocyclobutyl, dimethylcyclobutyl, hydroxycyclobutyl, ketocyclobutyl, cyclopentyl, halocyclopentyl, hydroxycyclopentyl, or ketocyclopentyl.

Another aspect of the invention is a compound of formula I where R[1] is cyclopropyl.

Another aspect of the invention is a compound of formula I where Ar[1] is 3-pyridinyl substituted with 0-3 substituents selected from cyano, halo, alkyl, haloalkyl, hydroxyalkyl, (hydroxyl)haloalkyl, alkoxyalkyl, (N)(R[2])(R[3])alkyl, benzyl, alkenyl, cycloalkyl, hydroxy, alkoxy, haloalkoxy, (hydroxyl)alkoxy, (alkoxy)alkoxy, (cycloalkyl)alkoxy, phenoxy, alkylcarbonyl, (haloalkyl)carbonyl, phenylcarbonyl, alkoxycarbonyl, carboxy, aminocarbonyl, acetamido, N(R[2])(R[3]) and Ar[2].

Another aspect of the invention is a compound of formula I where is Ar[2] is phenyl, naphthalenyl, pyrrolyl, furanyl, thienyl, pyrrazolyl, imidazolyl, thiazolyl, pyridinyl, pyrimidinyl, indolyl, benzofuranyl, benzothiophenyl, quinolinyl, and is substituted with 0-1 substituents selected from the group consisting of cyano, halo, alkyl, haloalkyl, alkoxy, haloalkoxy, alkylcarbonyl, or N(R[2])(R[3]).

For a compound of formula I, the scope of any instance of a variable substituent, including R[1], R[2], R[3], Ar[1], and Ar[2], can be used independently with the scope of any other instance of a variable substituent. As such, the invention includes combinations of the different aspects.

Unless specified otherwise, these terms have the following meanings. "Halo" includes fluoro, chloro, bromo, and iodo. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. "Haloalkyl" and "haloalkoxy" include all halogenated isomers from monohalo to perhalo. Terms with a hydrocarbon moiety (e.g. alkoxy) include straight and branched isomers for the hydrocarbon portion. "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a four- to six-membered aromatic or non-aromatic carbocyclic ring. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some Formula I compounds contain at least one asymmetric carbon atom, an example of which is shown below. The invention includes all stereoisomeric forms of the compounds, both mixtures and separated isomers. Mixtures of stereoisomers can be separated into individual isomers by methods known in the art.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Synthetic Methods

Compounds of Formula I may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention. The schemes encompass reasonable variations known in the art.

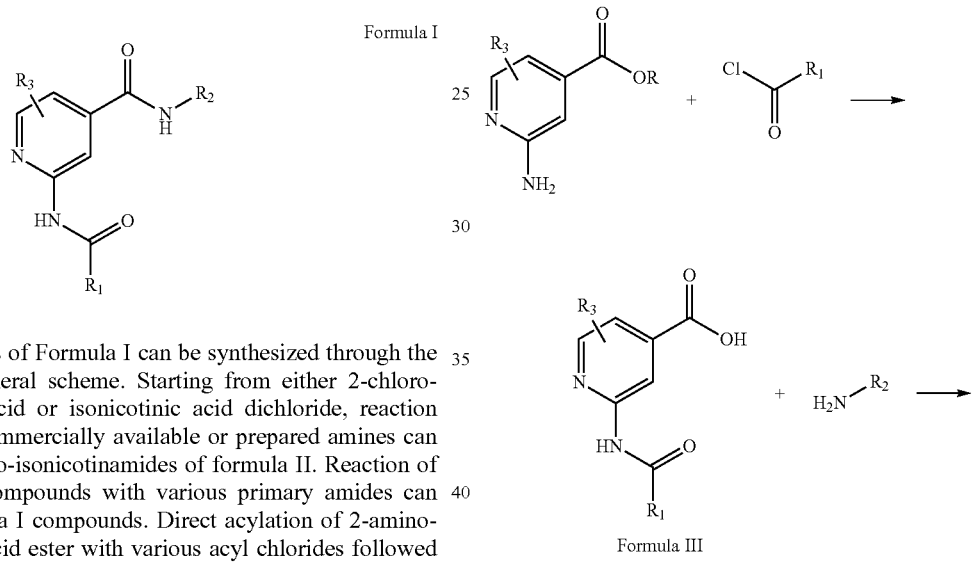

Formula I

Compounds of Formula I can be synthesized through the following general scheme. Starting from either 2-chloro-isonicotinic acid or isonicotinic acid dichloride, reaction with many commercially available or prepared amines can afford 2-chloro-isonicotinamides of formula II. Reaction of Formula II compounds with various primary amides can afford Formula I compounds. Direct acylation of 2-amino-isonicotinic acid ester with various acyl chlorides followed by hydrolysis can afford the intermediate acids of Formula III, which after brief amide formation reaction with various amines, commercial or prepared, can also lead to the desired Formula I compounds.

General Scheme I:

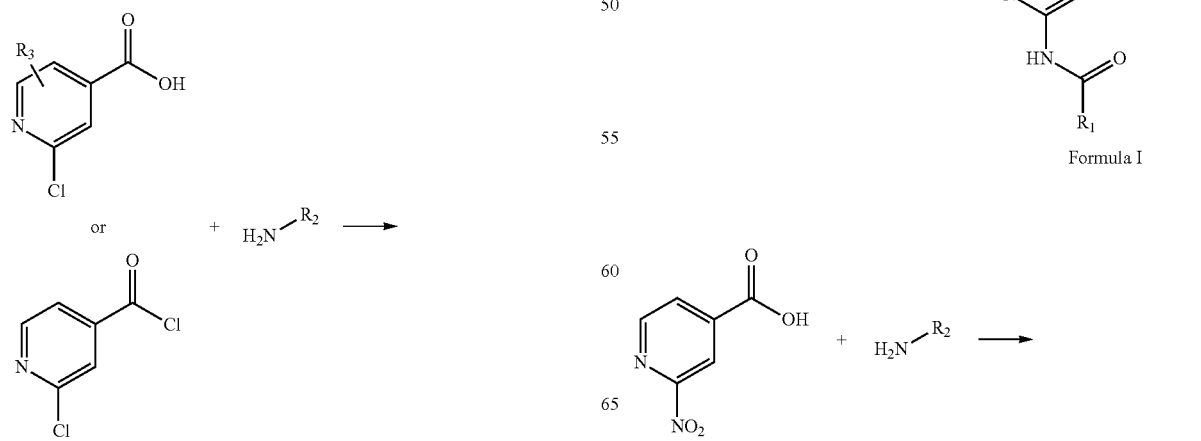

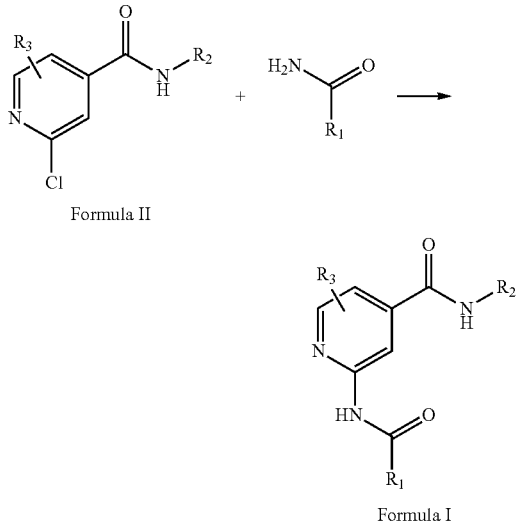

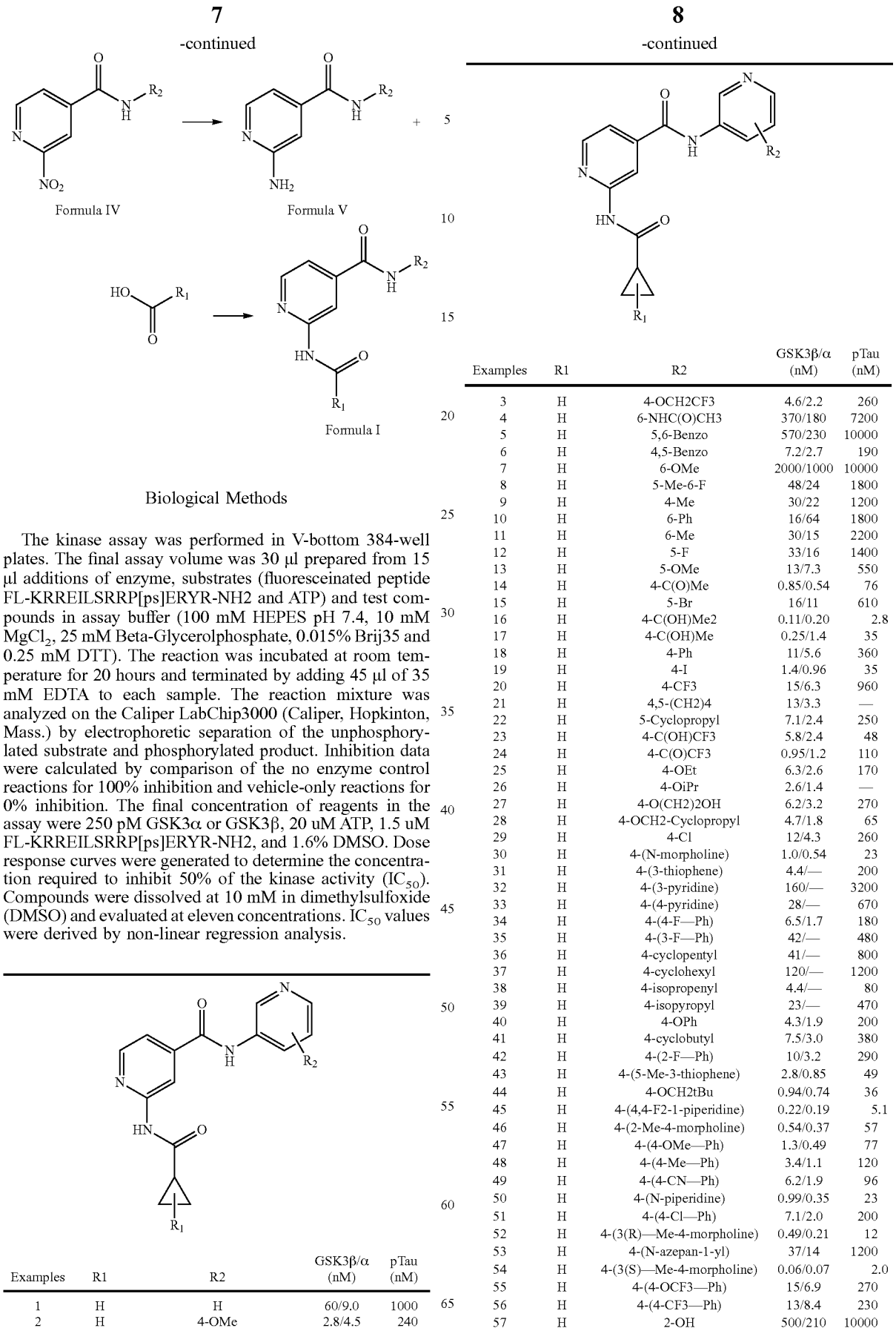

Biological Methods

The kinase assay was performed in V-bottom 384-well plates. The final assay volume was 30 μl prepared from 15 μl additions of enzyme, substrates (fluoresceinated peptide FL-KRREILSRRP[ps]ERYR-NH2 and ATP) and test compounds in assay buffer (100 mM HEPES pH 7.4, 10 mM $MgCl_2$, 25 mM Beta-Glycerolphosphate, 0.015% Brij35 and 0.25 mM DTT). The reaction was incubated at room temperature for 20 hours and terminated by adding 45 μl of 35 mM EDTA to each sample. The reaction mixture was analyzed on the Caliper LabChip3000 (Caliper, Hopkinton, Mass.) by electrophoretic separation of the unphosphorylated substrate and phosphorylated product. Inhibition data were calculated by comparison of the no enzyme control reactions for 100% inhibition and vehicle-only reactions for 0% inhibition. The final concentration of reagents in the assay were 250 pM GSK3α or GSK3β, 20 uM ATP, 1.5 uM FL-KRREILSRRP[ps]ERYR-NH2, and 1.6% DMSO. Dose response curves were generated to determine the concentration required to inhibit 50% of the kinase activity ($IC_{50}$). Compounds were dissolved at 10 mM in dimethylsulfoxide (DMSO) and evaluated at eleven concentrations. $IC_{50}$ values were derived by non-linear regression analysis.

| Examples | R1 | R2 | GSK3β/α (nM) | pTau (nM) |
|---|---|---|---|---|
| 1 | H | H | 60/9.0 | 1000 |
| 2 | H | 4-OMe | 2.8/4.5 | 240 |
| 3 | H | 4-OCH2CF3 | 4.6/2.2 | 260 |
| 4 | H | 6-NHC(O)CH3 | 370/180 | 7200 |
| 5 | H | 5,6-Benzo | 570/230 | 10000 |
| 6 | H | 4,5-Benzo | 7.2/2.7 | 190 |
| 7 | H | 6-OMe | 2000/1000 | 10000 |
| 8 | H | 5-Me-6-F | 48/24 | 1800 |
| 9 | H | 4-Me | 30/22 | 1200 |
| 10 | H | 6-Ph | 16/64 | 1800 |
| 11 | H | 6-Me | 30/15 | 2200 |
| 12 | H | 5-F | 33/16 | 1400 |
| 13 | H | 5-OMe | 13/7.3 | 550 |
| 14 | H | 4-C(O)Me | 0.85/0.54 | 76 |
| 15 | H | 5-Br | 16/11 | 610 |
| 16 | H | 4-C(OH)Me2 | 0.11/0.20 | 2.8 |
| 17 | H | 4-C(OH)Me | 0.25/1.4 | 35 |
| 18 | H | 4-Ph | 11/5.6 | 360 |
| 19 | H | 4-I | 1.4/0.96 | 35 |
| 20 | H | 4-CF3 | 15/6.3 | 960 |
| 21 | H | 4,5-(CH2)4 | 13/3.3 | — |
| 22 | H | 5-Cyclopropyl | 7.1/2.4 | 250 |
| 23 | H | 4-C(OH)CF3 | 5.8/2.4 | 48 |
| 24 | H | 4-C(O)CF3 | 0.95/1.2 | 110 |
| 25 | H | 4-OEt | 6.3/2.6 | 170 |
| 26 | H | 4-OiPr | 2.6/1.4 | — |
| 27 | H | 4-O(CH2)2OH | 6.2/3.2 | 270 |
| 28 | H | 4-OCH2-Cyclopropyl | 4.7/1.8 | 65 |
| 29 | H | 4-Cl | 12/4.3 | 260 |
| 30 | H | 4-(N-morpholine) | 1.0/0.54 | 23 |
| 31 | H | 4-(3-thiophene) | 4.4/— | 200 |
| 32 | H | 4-(3-pyridine) | 160/— | 3200 |
| 33 | H | 4-(4-pyridine) | 28/— | 670 |
| 34 | H | 4-(4-F—Ph) | 6.5/1.7 | 180 |
| 35 | H | 4-(3-F—Ph) | 42/— | 480 |
| 36 | H | 4-cyclopentyl | 41/— | 800 |
| 37 | H | 4-cyclohexyl | 120/— | 1200 |
| 38 | H | 4-isopropenyl | 4.4/— | 80 |
| 39 | H | 4-isopyropyl | 23/— | 470 |
| 40 | H | 4-OPh | 4.3/1.9 | 200 |
| 41 | H | 4-cyclobutyl | 7.5/3.0 | 380 |
| 42 | H | 4-(2-F—Ph) | 10/3.2 | 290 |
| 43 | H | 4-(5-Me-3-thiophene) | 2.8/0.85 | 49 |
| 44 | H | 4-OCH2tBu | 0.94/0.74 | 36 |
| 45 | H | 4-(4,4-F2-1-piperidine) | 0.22/0.19 | 5.1 |
| 46 | H | 4-(2-Me-4-morpholine) | 0.54/0.37 | 57 |
| 47 | H | 4-(4-OMe—Ph) | 1.3/0.49 | 77 |
| 48 | H | 4-(4-Me—Ph) | 3.4/1.1 | 120 |
| 49 | H | 4-(4-CN—Ph) | 6.2/1.9 | 96 |
| 50 | H | 4-(N-piperidine) | 0.99/0.35 | 23 |
| 51 | H | 4-(4-Cl—Ph) | 7.1/2.0 | 200 |
| 52 | H | 4-(3(R)—Me-4-morpholine) | 0.49/0.21 | 12 |
| 53 | H | 4-(N-azepan-1-yl) | 37/14 | 1200 |
| 54 | H | 4-(3(S)—Me-4-morpholine) | 0.06/0.07 | 2.0 |
| 55 | H | 4-(4-OCF3—Ph) | 15/6.9 | 270 |
| 56 | H | 4-(4-CF3—Ph) | 13/8.4 | 230 |
| 57 | H | 2-OH | 500/210 | 10000 |

-continued

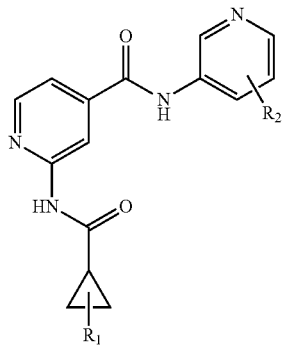

| Examples | R1 | R2 | GSK3β/α (nM) | pTau (nM) |
|---|---|---|---|---|
| 58 | H | 2-F | 35/34 | 1600 |
| 59 | H | 2-Cl-4-Ph | 78/70 | 8200 |
| 60 | H | 4-N (7-azanorbornane) | 16/5.7 | 620 |
| 61 | H | 2-CN | 65/43 | — |
| 62 | H | 2-Ph-4-OMe | 2.6/4.8 | 310 |
| 63 | H | 2-Ph-4,5-Benzo | 12/56 | 4100 |
| 64 | H | 4-(5-pyrimidine) | 97/76 | 10000 |
| 65 | H | 4-(2,4-(CF3)2—Ph) | 29/25 | — |
| 66 | H | 4-(2,4-Cl2—Ph) | 3.6/2.1 | — |
| 67 | H | 4-(2-CF3—Ph) | 1.4/0.66 | 28 |
| 68 | H | 4-(2-Cl—Ph) | 2.3/0.88 | 61 |
| 69 | H | 4-(2-Cl-4-F—Ph) | 0.70/0.28 | 29 |
| 70 | H | 4-(2-Cl-4-CF3—Ph) | 7.0/4.5 | 280 |
| 71 | H | 4-(2-CF3-4-F—Ph) | 0.33/0.17 | 14 |
| 72 | H | 4-(4-nPr—Ph) | 3.1/6.4 | 250 |
| 73 | H | 4-(2,4-F2—Ph) | 1.0/0.34 | 62 |
| 74 | H | 4-(4-tBu—Ph) | 5.4/19 | 800 |
| 75 | H | 4-(4-iPr—Ph) | 30/7.4 | 460 |
| 76 | H | 4-(2-F-4-Cl—Ph) | 4.9/1.2 | 75 |
| 77 | H | 4-(2(R)—Me-4-morpholine) | 8.8/2.7 | 220 |
| 78 | H | 4-(2(S)—Me-4-morpholine) | 0.99/0.35 | 18 |
| 79 | H | 4-(2,6(cis)-Me2-4-morpholine) | 14/5.5 | 190 |
| 80 | H | 4-(3,3-F2-1-piperidine) | 1.5/0.46 | 34 |
| 81 | H | 4-(2-F-4-OMe—Ph) | 1.3/0.58 | 31 |
| 82 | H | 4-(2-F-4-CF3—Ph) | 9.6/4.0 | 200 |
| 83 | H | 4-(3,3-F2-1-pyrrolidine) | 71/49 | 4400 |
| 84 | H | 4-(2,5-F2—Ph) | 28/15 | 770 |
| 85 | H | 4-(2-F-4-CN—Ph) | 2.9/0.94 | 33 |
| 86 | H | 4-(2-F-5-Cl—Ph) | 54/26 | 630 |
| 87 | H | 4-(2,2-Me2-4-morpholine) | 0.79/0.39 | 25 |
| 88 | H | 2-F-4-(4-morpholine) | 9.1/3.9 | 170 |
| 89 | H | 4-(2-CN-4-F—Ph) | 470/190 | — |
| 90 | H | 4-(3,3-Me2-4-morpholine) | 0.15/0.10 | 0.40 |
| 91 | H | 4-(2,3-F2—Ph) | 19/6.4 | 230 |
| 92 | H | 4-(2-F-4-C(O)NMe2—Ph) | 24/11 | 460 |
| 93 | H | 4-(4-OCHF2—Ph) | 7.8/3.1 | 180 |
| 94 | H | 4-(2-F-4-OCF3—Ph) | 13/5.0 | 120 |
| 95 | H | 4-(2-benzofuran) | 1.9/1.4 | 100 |
| 96 | H | 4-(1-Me-2-indole) | 4.1/1.7 | 66 |
| 97 | 2,2-Me2 | 4-Ph | 1.1/8.5 | 870 |
| 98 | 2,2-F2 | 4-Ph | 11/17 | 1400 |

-continued

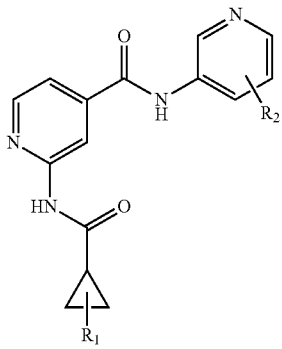

| Examples | R1 | R2 | GSK3β/α (nM) | pTau (nM) |
|---|---|---|---|---|
| 99 | 2(trans)-Ph | 4-Ph | 1.8/24 | 4500 |
| 100 | 2(trans)-Me | 4-Ph | 26/7.5 | 350 |
| 101 | H | 5-COOMe | 30/13 | 3100 |
| 102 | H | 5-Me | 9.5/5.4 | 740 |
| 103 | H | 5-COOH | 197/121 | 10000 |
| 104 | H | 5-Ph | 5/2 | 270 |
| 105 | H | 5-CONH2 | 6.5/3.6 | 6900 |
| 106 | H | 5-(4-Py) | 4.8/2.5 | 320 |
| 107 | H | 5-(OPh) | 19/9.1 | 3300 |
| 108 | H | 5-(N-piperidine) | 130/23 | 5400 |
| 109 | H | 5-(N-Morpholine) | 73/17 | 2000 |
| 110 | H | 5-(CH2Ph) | 73/11 | 5600 |
| 111 | H | 5-(4-F—Ph) | 6.4/0.95 | 570 |
| 112 | H | 5-(3,4-diF—Ph) | BMT | 041729 |
| 113 | H | 5-cyclobutyl | 1.0/1.75 | 330 |
| 114 | H | 5-(2,4-diF—Ph) | 1.6/1.3 | 990 |
| 115 | H | 5-(4-CN—Ph) | 4.1/4.3 | 780 |
| 116 | H | 5-(2-F—Ph) | 0.35/0.28 | 180 |
| 117 | H | 5-(3-thiophene) | 1.2/1.9 | — |
| 118 | H | 5-(1-pyrazole) | 1.5/0.74 | 330 |
| 119 | H | 5-(1-imidazole) | 2.4/1.0 | 410 |
| 120 | H | 5-(4-OCF3—Ph) | 11/8.0 | 5400 |
| 121 | H | 5-(3-furan) | 2.4/0.99 | — |
| 122 | H | 5-(2-Me—Ph) | 7.3/3.3 | — |
| 123 | H | 5-(2-OMe—Ph) | 3.7/1.4 | 200 |
| 124 | H | 5-(2-CF3—Ph) | 12/6.1 | 510 |
| 125 | H | 5-(3-pyridine) | 2.0/0.86 | — |
| 126 | H | 5-(3-F—Ph) | 2.5/1.1 | — |
| 127 | H | 5-(2-Cl—Ph) | 1.3/0.54 | — |
| 128 | H | 5-(2-pyridine) | 0.5/2.6 | — |
| 129 | H | 5-(3-benzo[b]thiophene) | 5.1/7.0 | — |
| 130 | H | 5-(4-Me-3-thiophene) | 2.5/0.41 | — |
| 131 | H | 5-(4-CN-3-thiophene) | 0.41/0.76 | — |
| 132 | H | 5-cyclopentyl | 4.1/8.0 | — |
| 133 | H | 5-(4-Cl—Ph) | 3.3/4.4 | — |
| 134 | H | 5-(2-iPr—Ph) | 2.7/— | — |
| 135 | H | 5-(2,5 diMe 3-thiophene) | 2.7/— | — |
| 136 | H | 5-(2-OiPr—Ph) | 19/5.4 | — |
| 137 | H | 5-(2,3-diF—Ph) | 3.4/0.74 | — |
| 138 | H | 5-(2,3-diCl—Ph) | 10.5/1.8 | — |
| 139 | H | 5-(2-F,3-OMe—Ph) | 3.7/0.81 | — |
| 140 | H | 5-(2-F,3-Cl—Ph) | 13/2.8 | — |
| 141 | H | 5-(2,6-diF—Ph) | 21/4.3 | — |
| 142 | H | 5-(2,5-diF—Ph) | 1.5/0.76 | 100 |
| 143 | H | 5-(8-quinoline) | 190/35 | — |
| 144 | H | 5-(2-COCH3—Ph) | 55/15 | — |
| 145 | H | 5-(2-CH2N(Me)2) | 780/170 | 1400 |
| 146 | H | 5-(2-OPr—Ph) | 4.5/3.4 | — |
| 147 | H | 5-(8-1H-indole) | 27/5.9 | 950 |
| 148 | H | 5-(2,4-diCl—Ph) | 9.7/2.4 | 620 |
| 149 | H | 5-(2-OCF3—Ph) | 8.5/1.75 | — |
| 150 | H | 5-CF3 | 88/17 | — |
| 151 | H | 5-(1-methyl-1H-pyrrol-3-yl) | 8.8/3.1 | 240 |
| 152 | H | 5-(1-methyl-1H-pyrazol-4-yl) | 4.9/1.4 | — |
| 153 | H | 5-(2-F,5-Cl—Ph) | 5.3/1.6 | — |
| 154 | H | 5-(2-NMe2—Ph) | 40/18 | — |
| 155 | H | 5-(3-Cl—Ph) | 9.1/3.3 | 770 |

-continued

| Examples | R1 | R2 | GSK3β/α (nM) | pTau (nM) |
|---|---|---|---|---|
| 156 | H | 5-(3-morpholino-Ph) | 11/3.6 | 420 |
| 157 | H | 5-(3-OCHF2—Ph) | 7.9/3.3 | 670 |
| 158 | H | 5-(2-Cl,3-OEt—Ph) | 7.7/2.5 | 425 |
| 159 | H | 5-(2-Me,5-yl- thiazole) | 4.7/1.9 | — |
| 160 | H | 5-(3-Cl, pyridine-5-yl) | 3.9/1.6 | 150 |
| 161 | H | 5-(3-F, pyridine-5-yl) | 1.7/0.6 | 175 |
| 162 | H | 5-(2-Me, pyridine-5-yl) | 2.5/1.1 | 115 |
| 163 | H | 5-(2-F, pyridine-5-yl) | 6.0/1.7 | 130 |
| 164 | H | 5-(2-OMe,pyridine-6-yl) | 6.0/1.4 | 270 |
| 165 | H | 5-(2-F, pyridine-6-yl) | 3.8/1.3 | 125 |
| 166 | H | 5-(2,3-diF, pyridine-4-yl) | 44/11 | 360 |
| 167 | H | 4-(2,5 diBr—Ph) | 20/9.3 | 5500 |
| 168 | H | 4-(4-Br—Ph) | 6.8/2.2 | 240 |
| 169 | H | 4-(4-I—Ph) | 2.8/1.5 | 170 |

| Examples | R | GSK3β/α (nM) | pTau (nM) |
|---|---|---|---|
| 170 | 3-methylpyrazine | 8.1/2.9 | 570 |
| 171 | 4-methyl-1-isopropylpyrazole | 370/170 | 4000 |
| 172 | 4-methyl-1-(2,2,2-trifluoroethyl)pyrazole | 35/14 | 700 |
| 173 | 5-methylthiazole | 18/14 | 2500 |
| 174 | 1,5-dimethylimidazole | 2000/1200 | 10000 |
| 175 | 1,4,5-trimethylimidazole | 68/33 | 3700 |
| 176 | 4-methyl-2-(pyridin-2-yl)thiazole | 650/— | 5500 |
| 177 | 2,5-dimethylthiazole | 61/— | 3900 |
| 178 | 5-methylpyrimidine | 14/12 | 1200 |
| 179 | 4-(4,4-difluoropiperidin-1-yl)-5-methylpyrimidine | 160/40 | 3000 |
| 180 | 6-(2-fluorophenyl)-2-methylpyrazine | 6.2/1.2 | 190 |
| 181 | 5-methyl-2-phenylthiazole | 2000/— | 5500 |

-continued

[Structure: pyridine-4-carboxamide with N-R substituent and 2-(cyclopropanecarbonylamino) group]

| Examples | R | GSK3β/α (nM) | pTau (nM) |
|---|---|---|---|
| 182 | [2-methyl-thiazolo[5,4-c]pyridine] | 1300/470 | 10000 |
| 183 | [2-methyl-thiazole-5-carboxamide] | 530/200 | 10000 |
| 184 | [2,4-dimethylbenzothiazole] | 800/170 | 10000 |

[Structure: pyridine-4-carboxamide with N-(pyridin-3-yl-R) and 2-(isobutyrylamino) group]

| Example | R | GSK3β/α (nM) | pTau (nM) |
|---|---|---|---|
| 185 | 4-Ph | 1.4/4.2 | 180 |
| 186 | 4-(4-Cl—Ph) | 20/6.5 | 360 |
| 187 | 4-OCH2CHF2-6-F | 2.7/1.2 | 210 |
| 188 | [2-methoxyethyl-pyrrolidine] | 39/19 | 2200 |

-continued

[Structure: pyridine-4-carboxamide with N-(pyridin-3-yl-R) and 2-(isobutyrylamino) group]

| Example | R | GSK3β/α (nM) | pTau (nM) |
|---|---|---|---|
| 189 | [2-methoxyethyl-morpholine] | 2.3/1.1 | 99 |
| 190 | [3-methoxy-2-methyl-butan-2-ol] | 3.3/1.4 | 19 |
| 191 | [4-(2-ethyl-1,3-dioxolan-2-yl)]-6-Cl | 0.08/0.12 | 12 |
| 192 | 5-(2,5 diF—Ph) | 4.6/1.4 | 94 |
| 193 | 5-(2 F—Ph) | 5.6/2.2 | 85 |
| 194 | 5-(2,3 diF—Ph) | 3.8/1.4 | 140 |
| 195 | 5-(2 Cl—Ph) | 10/1.5 | 107 |
| 196 | 4-(COPh) | 13/5.9 | 520 |
| 197 | 4-(CHOHPh) | 19/12 | 320 |
| 198 | 4-(CF2Ph) | 390/230 | 9900 |
| 199 | 4-(CHFPh) | 10/12 | 720 |
| 200 | 4-(CH2=CPh) | 6.1/4.7 | 510 |
| 201 | 4-[OCH2-(1-methylcyclopropyl)] | 1.1/0.4 | 26 |
| 202 | 4-OCH2CF2CH3 | 1.0/0.46 | 50 |
| 203 | 4-OCH2CF3 | 0.72/0.35 | 70 |
| 204 | 4-OCH2CF2H | 1.8/0.97 | 41 |

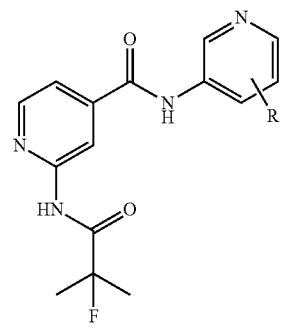

| Example | R | GSK3β/α (nM) | pTau (nM) |
|---|---|---|---|
| 205 | Ph | 49/52 | 5100 |

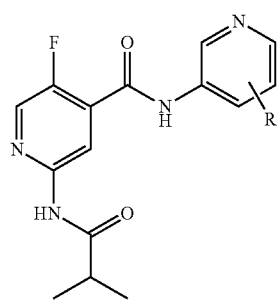

| Example | R | GSK3β/α (nM) | pTau (nM) |
|---|---|---|---|
| 206 | 4-(4,4-F2-piperidine) | 3.0/2.1 | 190 |

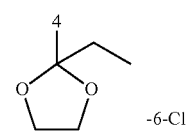

| Example | | GSK3β/α (nM) | pTau (nM) |
|---|---|---|---|
| 207 | | 2.5/1.1 | 160 |

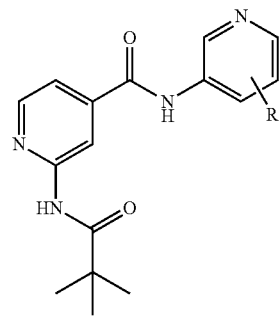

| Example | R1 | R | GSK3β/α (nM) | pTau (nM) |
|---|---|---|---|---|
| 208 | | 4-(4,4-F2-piperidine) | 4.2/3.1 | 120 |
| 209 | | 5-(2,3 diF Ph) | 24/14 | 2100 |
| 210 | | (2-ethyl-1,3-dioxolane)-6-Cl | 3.6/1.3 | 250 |

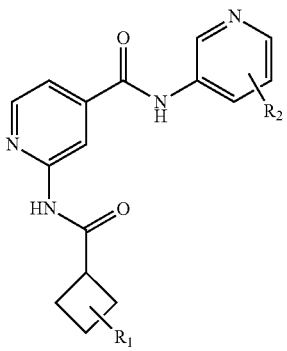

| Example | R1 | R2 | GSK3β/α (nM) | pTau (nM) |
|---|---|---|---|---|
| 211 | H | 4-OEt | 2.2/0.90 | 72 |
| 212 | H | 4-Ph | 4.3/4.4 | 96 |
| 213 | H | 5-Ph | —/2.8 | 1600 |
| 214 | 3,3-F2 | 5-Ph | 4.1/2.9 | 490 |
| 215 | 3-Cl | 4-Ph | 0.40/0.25 | — |
| 216 | 3,3-F2 | 4-Ph | 1.9/3.4 | 120 |
| 217 | 3,3-Me2 | 4-Ph | 1.7/3.2 | 170 |
| 218 | 3-Keto | 4-Ph | 3.9/— | — |
| 219 | 3-OH(trans) | 4-Ph | 17/6.4 | 450 |
| 220 | 3-Cl(trans)* | 4-(4,4-F2-1-piperidine) | 0.37/0.22 | 1.7 |
| 221 | 3-Cl(cis)* | 4-(4,4-F2-1-piperidine) | 0.16/0.09 | 1.9 |
| 222 | 3-F(trans)* | 4-(4-Cl—Ph) | 1.7/1.3 | 37 |
| 223 | 3-F(cis)* | 4-(4-Cl—Ph) | 6.9/3.1 | 150 |
| 224 | 3-Cl(trans)* | 4-(4-Cl—Ph) | —/— | 15 |
| 225 | 3-Cl(cis)* | 4-(4-Cl—Ph) | —/— | 43 |

*Arbitrarily assigned.

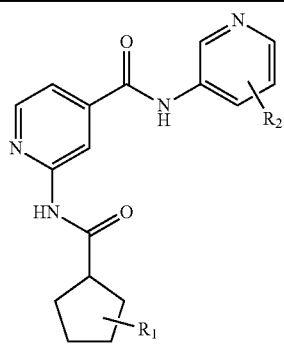

| Example | R1 | R2 | GSK3β/α (nM) | pTau (nM) |
|---|---|---|---|---|
| 226 | H | 4-OEt | 0.62/0.41 | 31 |
| 227 | H | 4-Ph | 1.6/1.4 | 47 |
| 228 | H | 4,5-Benzo | 1.6/1.1 | 130 |
| 229 | 3-Keto | 4-Ph | 1.6/— | — |
| 230 | 3-OH(trans) | 4-Ph | 2.5/0.68 | 73 |
| 231 | 3,3-F2 | 4-(4-Cl—Ph) | 0.46/0.90 | 30 |
| 232 | H | 5-Ph | 1.2/0.51 | 330 |
| 233 | 3,3-F2 | 5-Ph | 1.0/0.33 | 340 |
| 234 | 3,3-F2 | 5-(2F—Ph) | 1.4/0.9 | 160 |
| 235 | 3,3-F2 | 5-(2,3 diF—Ph) | 1.4/0.6 | 130 |
| 236 | 3,3-F2 | 5-(2,5 diF—Ph) | 4.3/2.1 | 180 |
| 237 | 3,3-F2 | 5-(2Cl—Ph) | 4.1/0.78 | 94 |
| 238 | 3,3-F2 | 4-(ethyl-dioxolane)-6-Cl | 0.11/0.07 | 8.3 |

Pharmaceutical Compositions and Methods of Treatment

Compounds of formula I can be useful in treating neurological or psychiatric disorders. Therefore, another aspect of the invention is a composition comprising a compound of formula I or a pharmaceutically acceptable salt thereof, and a pharmaceutically acceptable carrier.

Another aspect of the invention is a method for the treatment of depression, Alzheimer's disease, Parkinson's disease, or neuropathic pain, which comprises administering to a patient a therapeutically affective amount of a compound of formula I.

Another aspect of the invention is a method for the treatment of Alzheimer's disease which comprises administering to a patient a therapeutically affective amount of a compound of formula I.

Another aspect of the invention is the use of a compound of formula I in the manufacture of a medicament for the treatment of neurological or psychiatric disorders.

Another aspect of the invention is the use of a compound of formula I in the manufacture of a medicament for the treatment of depression, Alzheimer's disease, Parkinson's disease, neuropathic pain, or Parkinson's disease.

Another aspect of the invention is the use of a compound of formula I in the manufacture of a medicament for the treatment of Alzheimer's disease.

"Patient" means a person suitable for therapy as understood by practitioners in the field of affective disorders and neurodegenerative disorders.

"Treatment," "therapy," and related terms are used as understood by practitioners in the field of neurological and psychiatric disorders.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

DESCRIPTION OF SPECIFIC EMBODIMENTS

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC" for t-butoxycarbonyl, "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

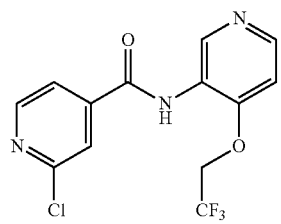

2-Chloro-N-(4-(2,2,2-trifluoroethoxy)pyridin-3-yl)isonicotinamide

MS (ESI) (m/z): 332 (M+H)$^+$.

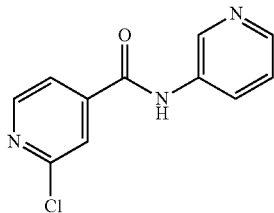 [SMILES: O=C(Nc1cccnc1)c1ccnc(Cl)c1]

2-Chloro-N-(pyridin-3-yl)isonicotinamide

In a 10 mL round-bottom flask was dissolved 2-chloroisonicotinoyl chloride (227.3 mg, 1.291 mmol) in methylene chloride to give a colorless solution. Pyridin-3-amine (134 mg, 1.42 mmol) was added, and a precipitate formed. Hunig's Base (0.248 mL, 1.421 mmol) was added and all solids dissolved. The mixture was stirred at rt for 18 h. The mixture was purified by flash column chromatography using silica gel and eluting with a gradient up to 8% methanol/methylene chloride affording the desired product (248.4 mg, 82%) as a white solid: MS (ESI) (m/z): 234 (M+H)$^+$; $^1$H NMR (400 MHz, CDCl$_3$) δ 8.73 (d, J=2.5 Hz, 1H), 8.62 (dd, J=5.1, 0.6 Hz, 1H), 8.47 (dd, J=4.8, 1.4 Hz, 1H), 8.30 (d, J=7.5 Hz, 1H), 8.20 (s, 1H), 7.85-7.79 (m, 1H), 7.69 (dd, J=5.1, 1.5 Hz, 1H), 7.40 (dd, J=8.3, 4.8 Hz, 1H).

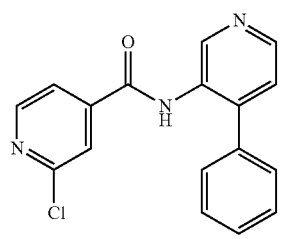 [SMILES: O=C(Nc1cnccc1-c1ccccc1)c1ccnc(Cl)c1]

2-Chloro-N-(4-phenylpyridin-3-yl)isonicotinamide

MS (ESI) (m/z): 310 (M+H)$^+$.

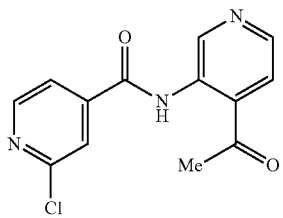 [SMILES: CC(=O)c1ccncc1NC(=O)c1ccnc(Cl)c1]

N-(4-Acetylpyridin-3-yl)-2-chloroisonicotinamide

MS (ESI) (m/z): 276 (M+H)$^+$.

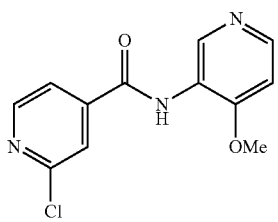

2-Chloro-N-(4-methoxypyridin-3-yl)isonicotinamide

MS (ESI) (m/z): 264 (M+H)$^+$; $^1$H NMR (400 MHz, CDCl$_3$) δ 9.41 (s, 1H), 8.58 (s, 1H), 8.52 (d, J=5.1 Hz, 1H), 8.29 (d, J=5.6 Hz, 1H), 7.75 (s, 1H), 7.63 (dd, J=5.1, 1.4 Hz, 1H), 6.86 (d, J=5.6 Hz, 1H), 3.97 (s, 3H).

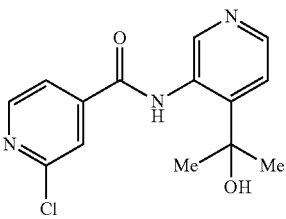 [SMILES: CC(C)(O)c1ccncc1NC(=O)c1ccnc(Cl)c1]

2-Chloro-N-(4-(2-hydroxypropan-2-yl)pyridin-3-yl)isonicotinamide

MS (ESI) (m/z): 292 (M+H)$^+$; $^1$H NMR (400 MHz, MeOD) δ 9.58 (s, 1H), 8.62 (dd, J=5.2, 0.6 Hz, 1H), 8.32 (d, J=5.3 Hz, 1H), 7.92 (dd, J=1.5, 0.6 Hz, 1H), 7.83 (dd, J=5.2, 1.5 Hz, 1H), 7.46 (d, J=5.2 Hz, 1H), 1.69 (s, 6H).

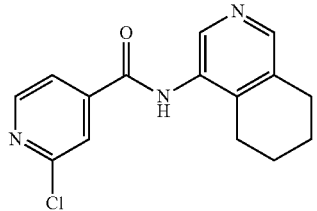 [SMILES: O=C(Nc1cncc2c1CCCC2)c1ccnc(Cl)c1]

2-Chloro-N-(5,6,7,8-tetrahydroisoquinolin-4-yl)isonicotinamide

MS (ESI) (m/z): 288 (M+H)⁺.

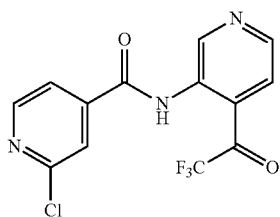

2-Chloro-N-(4-(2,2,2-trifluoroacetyl)pyridin-3-yl)isonicotinamide

MS (ESI) (m/z): 330 (M+H)⁺.

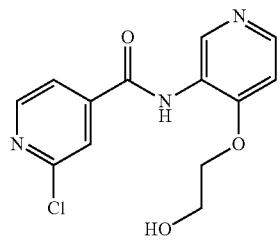 [SMILES: O=C(Nc1cnccc1OCCO)c1ccnc(Cl)c1]

2-Chloro-N-(4-(2-hydroxyethoxy)pyridin-3-yl)isonicotinamide

MS (ESI) (m/z): 294 (M+H)⁺; ¹H NMR (400 MHz, MeOD) δ 9.06 (s, 1H), 8.57 (dd, J=5.1, 0.6 Hz, 1H), 8.29 (d, J=5.8 Hz, 1H), 7.95 (d, J=0.7 Hz, 1H), 7.84 (dd, J=5.2, 1.5 Hz, 1H), 7.15 (d, J=5.8 Hz, 1H), 4.30-4.24 (m, 2H), 4.01-3.94 (m, 2H).

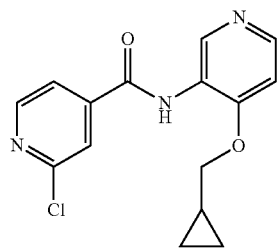 [SMILES: O=C(Nc1cnccc1OCC1CC1)c1ccnc(Cl)c1]

2-Chloro-N-(4-(cyclopropylmethoxy)pyridin-3-yl)isonicotinamide

MS (ESI) (m/z): 304 (M+H)⁺; ¹H NMR (400 MHz, CDCl3) δ 9.39 (s, 1H), 8.65 (s, 1H), 8.51 (dd, J=5.1, 0.5 Hz, 1H), 8.24 (d, J=5.6 Hz, 1H), 7.74 (d, J=0.7 Hz, 1H), 7.60 (dd, J=5.1, 1.5 Hz, 1H), 6.80 (d, J=5.6 Hz, 1H), 3.96 (d, J=7.1 Hz, 2H), 1.38-1.23 (m, 1H), 0.72-0.63 (m, 2H), 0.40-0.33 (m, 2H).

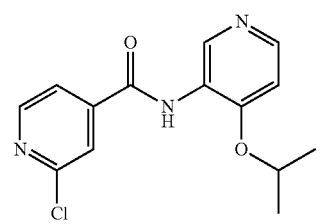 [SMILES: CC(C)Oc1ccncc1NC(=O)c1ccnc(Cl)c1]

2-Chloro-N-(4-isopropoxypyridin-3-yl)isonicotinamide

MS (ESI) (m/z): 292 (M+H)⁺; ¹H NMR (400 MHz, CDCl3) δ 9.33 (s, 1H), 8.64 (s, 1H), 8.47 (dd, J=5.1, 0.5 Hz, 1H), 8.20 (d, J=5.6 Hz, 1H), 7.70 (d, J=0.7 Hz, 1H), 7.56 (dd, J=5.1, 1.5 Hz, 1H), 6.80 (d, J=5.7 Hz, 1H), 4.70 (hept, J=6.1 Hz, 1H), 1.37 (d, J=6.1 Hz, 6H).

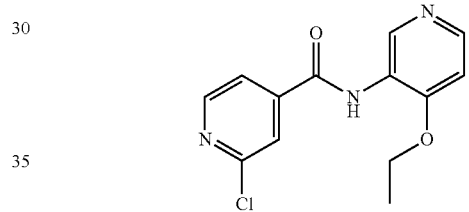

2-Chloro-N-(4-ethoxypyridin-3-yl)isonicotinamide

MS (ESI) (m/z): 278 (M+H)⁺; ¹H NMR (400 MHz, CHLOROFORM-d) δ 9.51 (s, 1H), 8.61-8.55 (m, 1H), 8.41 (br. s., 1H), 8.32 (d, J=5.5 Hz, 1H), 7.80-7.75 (m, 1H), 7.62 (dd, J=5.0, 1.5 Hz, 1H), 6.86 (d, J=5.5 Hz, 1H), 4.25 (q, J=7.0 Hz, 2H), 1.53 (t, J=7.0 Hz, 3H).

2-Chloro-N-(4-(2-hydroxypropan-2-yl)pyridin-3-yl)isonicotinamide

MS (ESI) (m/z): 276 (M+H)⁺.

Example 1

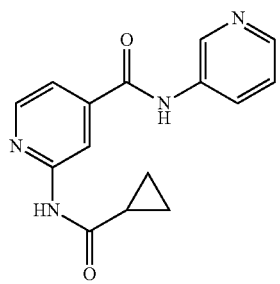 [SMILES: O=C(Nc1cccnc1)c1ccnc(NC(=O)C2CC2)c1]

2-(Cyclopropanecarboxamido)-N-(pyridin-3-yl)isonicotinamide

Into a 5 mL microwave tube under a nitrogen atmosphere was added 2-chloro-N-(pyridin-3-yl)isonicotinamide (50.5 mg, 0.216 mmol), cyclopropanecarboxamide (55.2 mg, 0.648 mmol), and potassium carbonate (44.8 mg, 0.324 mmol) in dioxane (2 mL) (degassed) to give a colorless suspension. PdOAc)$_2$ (7.28 mg, 0.032 mmol) and XANTPHOS (37.5 mg, 0.065 mmol) were added. The vial was sealed and heated at 150° C. for 2 h. Volatile components were removed in vacuo. The residue was suspended in 3 ml dimethylformamide and filtered. The solution was purified by prep-HPLC to afford the desired product (5 mg, 8%): MS (ESI) (m/z): 283 (M+H)$^+$; $^1$H NMR (500 MHz, DMSO) δ 11.06 (s, 1H), 10.74 (s, 1H), 8.92 (d, J=2.4 Hz, 1H), 8.55 (s, 1H), 8.53 (d, J=5.0 Hz, 1H), 8.36 (dd, J=4.7, 1.5 Hz, 1H), 8.19 (ddd, J=8.3, 2.5, 1.5 Hz, 1H), 7.57 (dd, J=5.1, 1.5 Hz, 1H), 7.43 (ddd, J=8.3, 4.7, 0.6 Hz, 1H), 2.14-1.99 (m, 1H), 0.93-0.81 (m, 4H).

Example 2

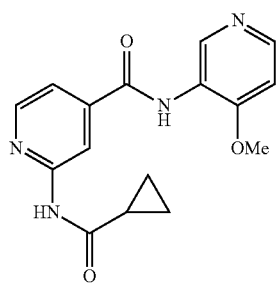 [SMILES: COc1ccncc1NC(=O)c1ccnc(NC(=O)C2CC2)c1]

2-(Cyclopropanecarboxamido)-N-(4-methoxypyridin-3-yl)isonicotinamide

MS (ESI) (m/z): 313 (M+H)$^+$; $^1$H NMR (500 MHz, DMSO) δ 11.02 (s, 1H), 10.07 (s, 1H), 8.57 (s, 1H), 8.54 (s, 1H), 8.50 (d, J=5.0 Hz, 1H), 8.38 (d, J=5.6 Hz, 1H), 7.57 (d, J=4.5 Hz, 1H), 7.19 (d, J=5.7 Hz, 1H), 3.90 (s, 3H), 2.05 (tt, J=6.9, 5.5 Hz, 1H), 0.92-0.80 (m, 4H).

Example 3

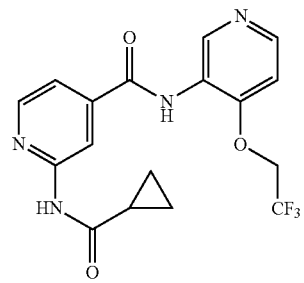 [SMILES: O=C(Nc1cnccc1OCC(F)(F)F)c1ccnc(NC(=O)C2CC2)c1]

2-(Cyclopropanecarboxamido)-N-(4-(2,2,2-trifluoroethoxy)pyridin-3-yl)isonicotinamide MS (ESI) (m/z): 381 (M+H)$^+$; $^1$H NMR (500 MHz, MeOD) δ 11.83 (s, 1H), 11.01 (s, 1H), 9.34 (s, 2H), 9.32 (d, J=5.2 Hz, 1H), 9.25 (d, J=5.7 Hz, 1H), 8.33 (d, J=4.3 Hz, 1H), 8.13 (d, J=5.7 Hz, 1H), 5.76 (q, J=8.7 Hz, 2H), 2.85 (dq, J=6.6, 5.7 Hz, 1H), 1.69-1.64 (m, 4H).

Example 4

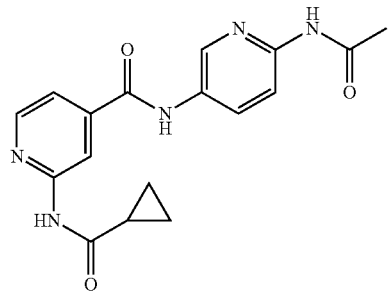 [SMILES: CC(=O)Nc1ccc(NC(=O)c2ccnc(NC(=O)C3CC3)c2)cn1]

N-(6-Acetamidopyridin-3-yl)-2-(cyclopropanecarboxamido)isonicotinamide

MS (ESI) (m/z): 340 (M+H)$^+$.

Example 5

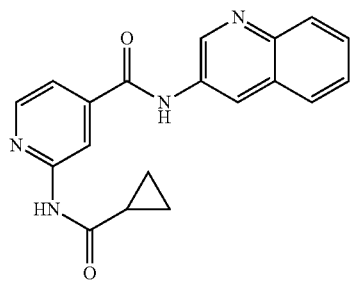 [SMILES: O=C(Nc1cnc2ccccc2c1)c1ccnc(NC(=O)C2CC2)c1]

2-(Cyclopropanecarboxamido)-N-(quinolin-3-yl)isonicotinamide

MS (ESI) (m/z): 333 (M+H)$^+$.

Example 7

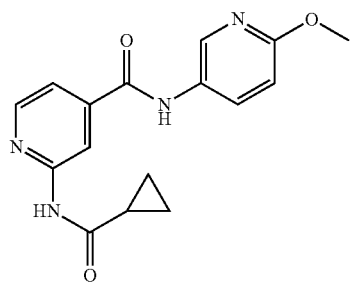 [SMILES: COc1ccc(NC(=O)c2ccnc(NC(=O)C3CC3)c2)cn1]

2-(Cyclopropanecarboxamido)-N-(6-methoxypyridin-3-yl)isonicotinamide

MS (ESI) (m/z): 313 (M+H)$^+$.

Example 8

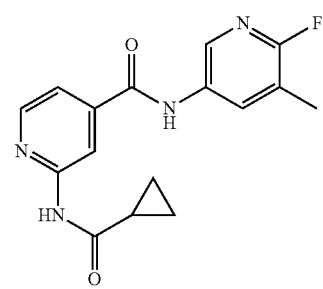 [SMILES: Cc1cc(NC(=O)c2ccnc(NC(=O)C3CC3)c2)cnc1F]

2-(Cyclopropanecarboxamido)-N-(6-fluoro-5-methylpyridin-3-yl)isonicotinamide

MS (ESI) (m/z): 315 (M+H)$^+$.

Example 9

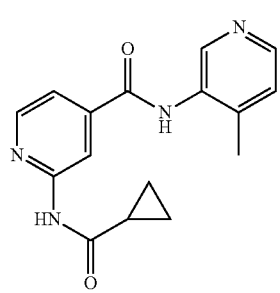 [SMILES: Cc1ccncc1NC(=O)c1ccnc(NC(=O)C2CC2)c1]

2-(Cyclopropanecarboxamido)-N-(4-methylpyridin-3-yl)isonicotinamide

MS (ESI) (m/z): 297 (M+H)$^+$.

Example 10

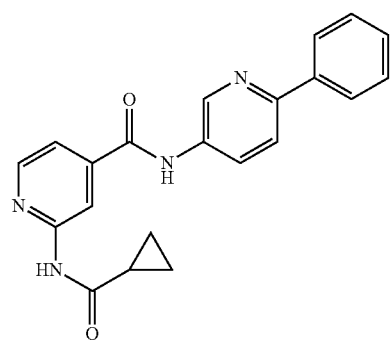 [SMILES: O=C(Nc1ccc(-c2ccccc2)nc1)c1ccnc(NC(=O)C2CC2)c1]

2-(Cyclopropanecarboxamido)-N-(6-phenylpyridin-3-yl)isonicotinamide

MS (ESI) (m/z): 359 (M+H)$^+$.

Example 11

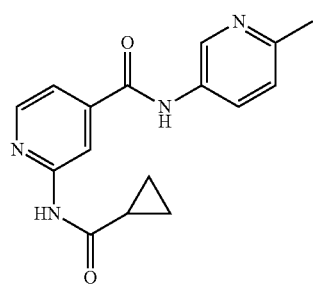 [SMILES: Cc1ccc(NC(=O)c2ccnc(NC(=O)C3CC3)c2)cn1]

2-(Cyclopropanecarboxamido)-N-(6-methylpyridin-3-yl)isonicotinamide

MS (ESI) (m/z): 297 (M+H)$^+$.

Example 12

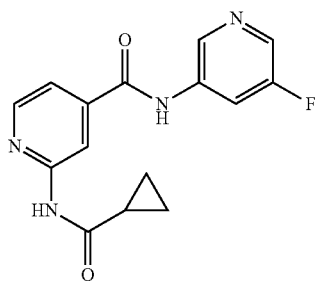 [SMILES: O=C(Nc1cncc(F)c1)c1ccnc(NC(=O)C2CC2)c1]

2-(Cyclopropanecarboxamido)-N-(5-fluoropyridin-3-yl)isonicotinamide

MS (ESI) (m/z): 301 (M+H)$^+$.

Example 13

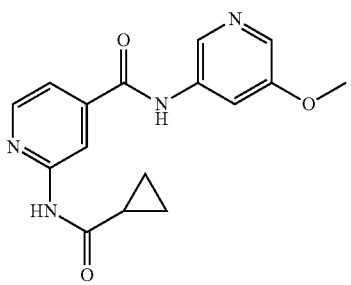 [SMILES: COc1cncc(NC(=O)c2ccnc(NC(=O)C3CC3)c2)c1]

2-(Cyclopropanecarboxamido)-N-(5-methoxypyridin-3-yl)isonicotinamide

MS (ESI) (m/z): 313 (M+H)$^+$.

Example 15

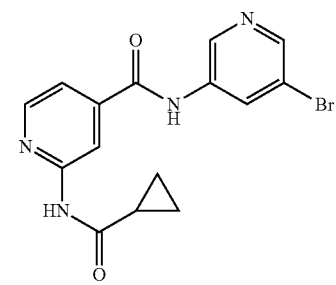 [SMILES: O=C(Nc1cncc(Br)c1)c1ccnc(NC(=O)C2CC2)c1]

2-(Cyclopropanecarboxamido)-N-(5-bromopyridin-3-yl)isonicotinamide

MS (ESI) (m/z): 363 (M+H)$^+$.

Example 14

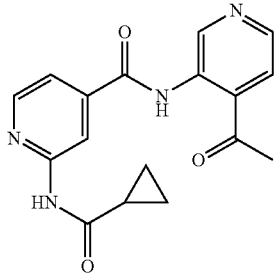

N-(4-acetylpyridin-3-yl)-2-(cyclopropanecarboxamido)isonicotinamide

MS (ESI) (m/z): 325 (M+H)$^+$; $^1$H NMR (400 MHz, CDCl3) δ 12.29 (s, 1H), 10.25 (s, 1H), 8.87 (s, 1H), 8.60 (d, J=5.1 Hz, 2H), 8.48 (dd, J=5.2, 0.7 Hz, 1H), 7.79-7.70 (m, 1H), 7.64 (dd, J=5.2, 1.6 Hz, 1H), 2.78 (s, 3H), 1.69-1.59 (m, 1H), 1.25-1.18 (m, 2H), 0.99-0.92 (m, 2H).

Example 16

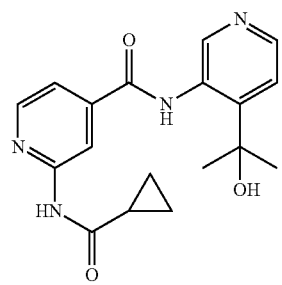 [SMILES: CC(C)(O)c1ccncc1NC(=O)c1ccnc(NC(=O)C2CC2)c1]

2-(Cyclopropanecarboxamido)-N-(4-(2-hydroxypropan-2-yl)pyridin-3-yl)isonicotinamide MS (ESI) (m/z): 341 (M+H)$^+$; $^1$H NMR (400 MHz, CDCl3) δ 11.29 (s, 1H), 9.72 (s, 1H), 8.73 (s, 1H), 8.54 (s, 1H), 8.46 (d, J=5.1 Hz, 1H), 8.35 (d, J=5.2 Hz, 1H), 7.67 (dd, J=5.1, 1.4 Hz, 1H), 7.17 (d, J=5.3 Hz, 1H), 3.87-3.71 (m, 1H), 1.74 (s, 6H), 1.65-1.60 (m, 1H), 1.16-1.09 (m, 2H), 0.98-0.92 (m, 2H).

Example 18

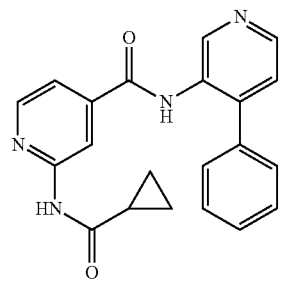 [SMILES: O=C(Nc1cnccc1-c1ccccc1)c1ccnc(NC(=O)C2CC2)c1]

2-(Cyclopropanecarboxamido)-N-(4-phenylpyridin-3-yl)isonicotinamide

MS (ESI) (m/z): 359 (M+H)$^+$; $^1$H NMR (500 MHz, DMSO) δ 11.00 (s, 1H), 10.46 (s, 1H), 8.63 (s, 1H), 8.58 (d, J=5.0 Hz, 1H), 8.46 (d, J=4.5 Hz, 2H), 7.55-7.48 (m, 3H), 7.48-7.43 (m, 2H), 7.40 (tt, J=6.2, 1.4 Hz, 2H), 2.04 (tt, J=7.1, 5.3 Hz, 1H), 0.90-0.80 (m, 4H).

Example 21

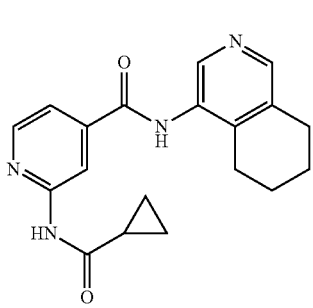 [SMILES: O=C(Nc1cncc2c1CCCC2)c1ccnc(NC(=O)C2CC2)c1]

2-(Cyclopropanecarboxamido)-N-(5,6,7,8-tetrahydroisoquinolin-4-yl)isonicotinamide MS (ESI) (m/z): 337 (M+H)$^+$; $^1$H NMR (500 MHz, DMSO) δ 11.04 (s, 1H), 10.25 (s, 1H), 8.57 (s, 1H), 8.51 (d, J=5.1 Hz, 1H), 8.28 (s, 1H), 8.22 (s, 1H), 7.58 (d, J=5.0 Hz, 1H), 2.78 (s, 2H), 2.63 (s, 2H), 2.06 (dq, J=6.6, 5.7 Hz, 1H), 1.83-1.68 (m, 4H), 0.91-0.78 (m, 4H).

Example 22

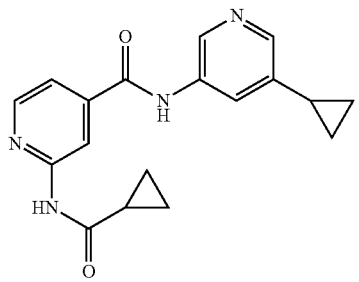 [SMILES: O=C(Nc1cncc(C2CC2)c1)c1ccnc(NC(=O)C2CC2)c1]

2-(Cyclopropanecarboxamido)-N-(5-cyclopropylpyridin-3-yl)isonicotinamide

MS (ESI) (m/z): 323 (M+H)$^+$.

Example 24

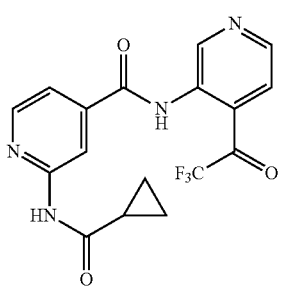 [SMILES: O=C(Nc1cnccc1C(=O)C(F)(F)F)c1ccnc(NC(=O)C2CC2)c1]

2-(Cyclopropanecarboxamido)-N-(4-(2,2,2-trifluoroacetyl)pyridin-3-yl)isonicotinamide MS (ESI) (m/z): 379 (M+H)$^+$.

Example 27

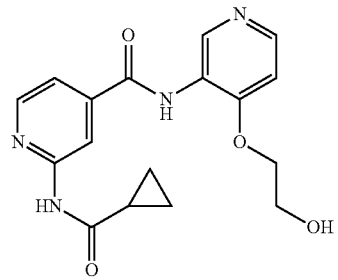 [SMILES: O=C(Nc1cnccc1OCCO)c1ccnc(NC(=O)C2CC2)c1]

2-(Cyclopropanecarboxamido)-N-(4-(2-hydroxyethoxy)pyridin-3-yl)isonicotinamide

MS (ESI) (m/z): 343 (M+H)$^+$; $^1$H NMR (500 MHz, DMSO) δ 11.04 (s, 1H), 8.75 (s, 1H), 8.54 (s, 1H), 8.51 (d, J=5.0 Hz, 1H), 8.32 (d, J=5.6 Hz, 1H), 7.55 (d, J=4.4 Hz, 1H), 7.19 (d, J=5.7 Hz, 1H), 4.16 (t, J=4.8 Hz, 2H), 3.78-3.71 (m, 2H), 2.06 (s, 1H), 0.91-0.85 (m, 4H).

Example 28

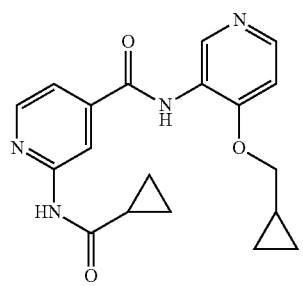 [SMILES: O=C(Nc1cnccc1OCC1CC1)c1ccnc(NC(=O)C2CC2)c1]

2-(Cyclopropanecarboxamido)-N-(4-(cyclopropylmethoxy)pyridin-3-yl)isonicotinamide MS (ESI) (m/z): 353 (M+H)$^+$; $^1$H NMR (400 MHz, DMSO) δ 11.03 (s, 1H), 9.98 (s, 1H), 8.57 (s, 2H), 8.51 (d, J=5.1 Hz, 1H), 8.34 (d, J=5.7 Hz, 1H), 7.56 (d, J=5.0 Hz, 1H), 7.16 (d, J=5.7 Hz, 1H), 4.01 (d, J=6.8 Hz, 2H), 2.10-1.98 (m, 1H), 1.27-1.23 (m, 1H), 0.86 (d, J=6.1 Hz, 4H), 0.59-0.51 (m, 2H), 0.42-0.32 (m, 2H).

Example 26

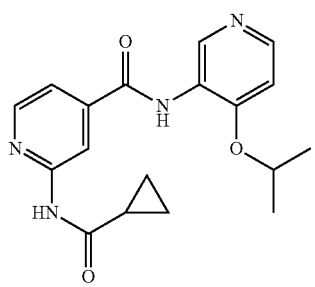 [SMILES: CC(C)Oc1ccncc1NC(=O)c1ccnc(NC(=O)C2CC2)c1]

2-(Cyclopropanecarboxamido)-N-(4-isopropoxypyridin-3-yl)isonicotinamide

MS (ESI) (m/z): 341 (M+H)$^+$; $^1$H NMR (500 MHz, DMSO) δ 11.03 (s, 1H), 9.86 (s, 1H), 8.60 (s, 1H), 8.55 (s,

1H), 8.51 (d, J=5.1 Hz, 1H), 8.32 (d, J=5.6 Hz, 1H), 7.54 (s, 1H), 7.18 (d, J=5.8 Hz, 1H), 4.80 (dt, J=12.1, 6.0 Hz, 1H), 2.10-2.01 (m, 1H), 1.31 (d, J=6.0 Hz, 6H), 0.90-0.84 (m, 4H).

Example 29

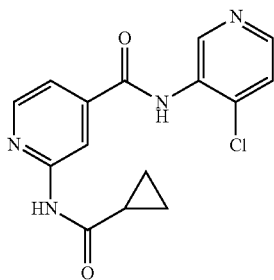

N-(4-chloropyridin-3-yl)-2-(cyclopropanecarboxamido)isonicotinamide

MS (ESI) (m/z): 317 (M+H)+; 1H NMR (400 MHz, CDCl3) δ 9.60 (s, 1H), 8.76 (s, 1H), 8.71 (d, J=0.7 Hz, 1H), 8.49 (dd, J=5.1, 0.7 Hz, 1H), 8.42 (s, 1H), 8.38 (d, J=5.3 Hz, 1H), 7.59 (dd, J=5.1, 1.6 Hz, 1H), 7.42 (d, J=5.2 Hz, 1H), 1.69-1.58 (m, 1H), 1.20-1.13 (m, 2H), 1.00-0.93 (m, 2H).

Example 25

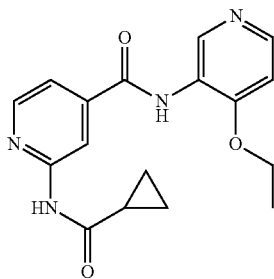 [SMILES: CCOc1ccncc1NC(=O)c1ccnc(NC(=O)C2CC2)c1]

2-(Cyclopropanecarboxamido)-N-(4-ethoxypyridin-3-yl)isonicotinamide

MS (ESI) (m/z): 327 (M+H)+; 1H NMR (400 MHz, CHLOROFORM-d) δ 9.58 (s, 1H), 8.70 (s, 1H), 8.50-8.41 (m, 3H), 8.35 (d, J=5.5 Hz, 1H), 7.59 (dd, J=5.0, 1.5 Hz, 1H), 6.87 (d, J=5.5 Hz, 1H), 4.24 (q, J=7.0 Hz, 2H), 1.67-1.60 (m, 1H), 1.59-1.54 (m, 3H), 1.17-1.12 (m, 2H), 0.99-0.94 (m, 2H).

Example 226

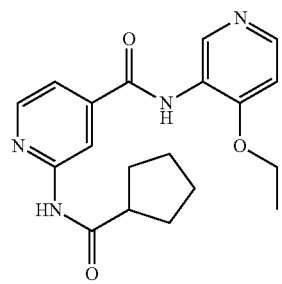 [SMILES: CCOc1ccncc1NC(=O)c1ccnc(NC(=O)C2CCCC2)c1]

2-(Cyclopentanecarboxamido)-N-(4-ethoxypyridin-3-yl)isonicotinamide

MS (ESI) (m/z): 355 (M+H)+; 1H NMR (400 MHz, DMSO-d6) δ 10.66-10.61 (m, 1H), 9.97-9.91 (m, 1H), 8.63-8.60 (m, 1H), 8.60-8.56 (m, 1H), 8.52-8.48 (m, 1H), 8.38-8.33 (m, 1H), 7.56-7.52 (m, 1H), 7.19-7.15 (m, 1H), 4.24-4.17 (m, 2H), 3.04-2.94 (m, 1H), 1.94-1.51 (m, 9H), 1.36 (s, 3H).

Example 211

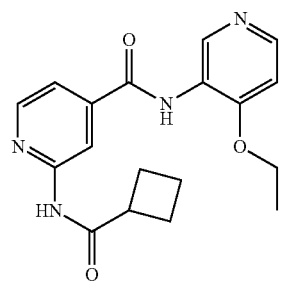 [SMILES: CCOc1ccncc1NC(=O)c1ccnc(NC(=O)C2CCC2)c1]

2-(Cyclobutanecarboxamido)-N-(4-ethoxypyridin-3-yl)isonicotinamide

MS (ESI) (m/z): 341 (M+H)+; 1H NMR (400 MHz, DMSO-d6) δ 10.53-10.48 (s, 1H), 9.97-9.90 (s, 1H), 8.61 (d, J=10.3 Hz, 2H), 8.51-8.47 (m, 1H), 8.35 (d, J=5.5 Hz, 1H), 7.57-7.52 (m, 1H), 7.18 (m, 1H), 4.21 (d, J=7.0 Hz, 2H), 3.47-3.37 (m, 1H), 2.31-2.09 (m, 4H), 2.03-1.76 (m, 2H), 1.37 (t, J=7.0 Hz, 3H)

Example 17

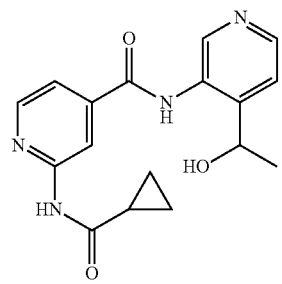 [SMILES: CC(O)c1ccncc1NC(=O)c1ccnc(NC(=O)C2CC2)c1]

2-(Cyclopropanecarboxamido)-N-(4-(1-hydroxyethyl)pyridin-3-yl)isonicotinamide

In a 100 mL round-bottom flask was dissolved N-(4-acetylpyridin-3-yl)-2-(cyclopropanecarboxamido)isonicotinamide (5.7 mg, 0.018 mmol) in methanol (1 mL) to give a colorless solution. Sodium borohydride (3.32 mg, 0.088 mmol) (excess) was added, and the mixture was stirred at rt for 1 h. LCMS showed complete conversion. The solvent was removed in vacuo. The residue was partitioned between saturated NaHCO$_3$ solution and ethyl acetate. The layers were separated. The organic layer was washed with brine, dried, and concentrated. The residue was purified by flash column chromatography on silica gel, eluting with 10% methanol/methylene chloride to afford the desired product (6.1 mg, 100%) as a white solid: MS (ESI) (m/z): 327 (M+H)$^+$; $^1$H NMR (400 MHz, CDCl$_3$) δ 10.64 (s, 1H), 9.58 (s, 1H), 8.73 (s, 1H), 8.68 (s, 1H), 8.45 (d, J=5.0 Hz, 1H), 8.34 (d, J=4.9 Hz, 1H), 7.64 (dd, J=5.1, 1.6 Hz, 1H), 7.09 (d, J=5.0 Hz, 1H), 5.14 (t, J=6.6 Hz, 1H), 4.44 (s, 1H), 1.68-1.59 (m, 4H), 1.15-1.08 (m, 2H), 0.99-0.90 (m, 2H).

Example 23

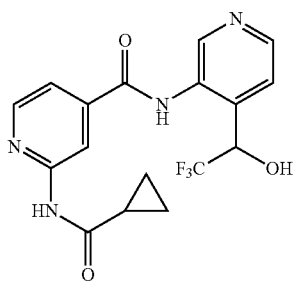 [SMILES: O=C(Nc1cnccc1C(O)C(F)(F)F)c1ccnc(NC(=O)C2CC2)c1]

2-(Cyclopropanecarboxamido)-N-(4-(2,2,2-trifluoro-1-hydroxyethyl)pyridin-3-yl)isonicotinamide A 100 mL round-bottom flask was charged with 2-(cyclopropanecarboxamido)-N-(4-(2,2,2-trifluoroacetyl)pyridin-3-yl)isonicotinamide (14 mg, 0.037 mmol) in methanol (2 mL) to give a white suspension. Sodium borohydride (7.00 mg, 0.185 mmol) (excess) was added, and the mixture was stirred at rt for 30 min. The crude material was purified by prep-HPLC to afford the desired product (10.3 mg, 73%): MS (ESI) (m/z): 381 (M+H)$^+$; $^1$H NMR (500 MHz, DMSO) δ 11.07 (s, 1H), 10.57 (s, 1H), 8.74 (s, 1H), 8.57 (d, J=5.0 Hz, 2H), 8.54 (d, J=5.1 Hz, 1H), 7.66 (d, J=5.0 Hz, 1H), 7.53 (d, J=5.1 Hz, 1H), 7.47 (d, J=5.8 Hz, 1H), 6.57 (s, 1H), 2.09-2.02 (m, 1H), 0.89-0.83 (m, 4H).

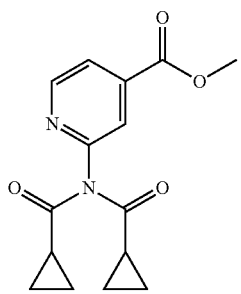 [SMILES: COC(=O)c1ccnc(N(C(=O)C2CC2)C(=O)C2CC2)c1]

Methyl 2-(N-(cyclopropanecarbonyl)cyclopropanecarboxamido)isonicotinate

Cyclopropanecarbonyl chloride (3.79 mL, 41.4 mmol) was added to a solution of methyl 2-aminoisonicotinamide and Hunig's base (7.23 mL, 41.4 mmol) in methylene chloride (150 mL) at 0° C. The reaction was stirred at 0° C. for 1 hour before quenching with water. The mixture was diluted with methylene chloride and washed with NaHCO$_3$ (sat.) and water. The organic layer was separated, dried (Na$_2$SO$_4$), filtered and concentrated. Flash column chromatography, eluting with ethyl acetate in hexane (0 to 50%) afforded the desired product (4.99 g, 88%) as a white solid: MS (ESI) (m/z): 311 (M+Na)$^+$.

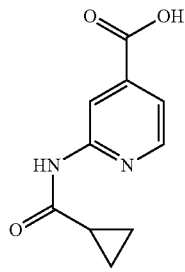 [SMILES: O=C(O)c1ccnc(NC(=O)C2CC2)c1]

2-(Cyclopropanecarboxamido)isonicotinic Acid

A mixture of LiOH (8.65 mL, 69.2 mmol, 8 M in water) and methyl 2-(N-(cyclopropanecarbonyl) cyclopropanecarboxamido)isonicotinate (4.99 g, 17.31 mmol) in tetrahydrofuran (20 mL) and methanol (2 mL) was stirred at room temperature for 18 h. The volatile components were removed in vacuo and the residue acidified by adding 1N HCl. The solid was filtered and washed with water. The white solid was used without further purification after drying under high vacuum for several hours (2.81 g, 79%): $^1$H NMR (400 MHz, DMSO-d$_6$) δ 11.02 (s, 1H), 8.56 (s, 1H), 8.48 (dd, J=5.3, 0.8 Hz, 1H), 7.51 (dd, J=5.0, 1.5 Hz, 1H), 2.06-1.98 (m, 1H), 0.88-0.81 (m, 4H).

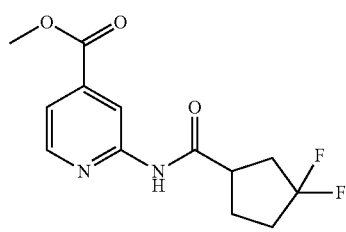 [SMILES: COC(=O)c1ccnc(NC(=O)C2CCC(F)(F)C2)c1]

Methyl 2-(3,3-difluorocyclopentanecarboxamido)isonicotinate

To a solution of ethyl 3-oxocyclopentanecarboxylate (0.5 g, 3.20 mmol) in methylene chloride (5 mL) at 0° C. was added DAST (2.115 mL, 16.01 mmol), dropwise over 30 seconds. The reaction was stirred at rt for 3 days. The mixture was quenched with methanol at 0° C. and then stirred for 5 mins. The solvent was removed and dried in vacuo. To the resulting crude product in tetrahydrofuran (2 mL) and ethanol (0.1 mL) was added 2N LiOH (1.094 mL, 2.189 mmol). The reaction mixture was stirred at rt for 1 h. The solvent was evaporated and 1N HCl was added. The mixture was extracted with ethyl acetate (3×). The organic extracts were combined and dried over sodium sulfate and concentrated.

To methyl 2-aminoisonicotinate (0.050 g, 0.330 mmol) and methyl 2-aminoisonicotinate (0.050 g, 0.330 mmol) in dimethylformamide (1 mL) was added DIEA (0.262 mL, 1.499 mmol) followed by 1-propanephosphonic acid cyclic anhydride (0.875 mL, 1.499 mmol) dropwise. The mixture was stirred at rt overnight. The reaction mixture was diluted with ethyl acetate and water. The organic extracts were combined and washed with brine, dried over sodium sulfate and evaporated. The crude product was purified by silica gel chromatography, eluting with 0-80% ethyl acetate/hexanes to give the desired product (0.045 g, 0.158 mmol, 53% yield). $^1$H NMR (400 MHz, Choroform-d) δ ppm 8.76 (s, 1H) 8.43 (dd, J=5.14, 0.98 Hz, 1H) 8.01 (br. s., 1H) 7.65 (dd, J=5.14, 1.47 Hz, 1H) 3.98 (s, 3H) 3.04 (quin, J=8.38 Hz, 1H) 2.40-2.67 (m, 2H) 2.12-2.39 (m, 4H). MS (ESI) (m/z): 285.1 (M+H)$^+$.

with 0-20% dichloromethane/methanol to the desired product (1.48 g, 6.32 mmol, 96% yield). MS (ESI) (m/z): 235.2 (M+H)$^+$.

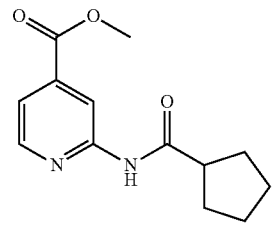

Methyl 2-(cyclopentanecarboxamido)isonicotinate $^1$H NMR (500 MHz, Chloroform-d) δ ppm 8.81 (s, 1H) 8.38 (dd, J=5.19, 0.61 Hz, 2H) 7.61 (dd, J=5.04, 1.37 Hz, 1H) 3.96 (s, 3H) 2.72-2.84 (m, 1H) 1.91-2.01 (m, 4H) 1.77-1.85 (m, 2H) 1.61-1.70 (m, 2H).

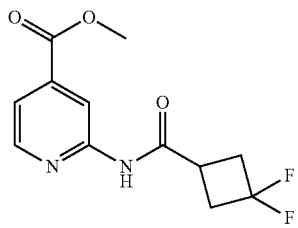 [SMILES: COC(=O)c1ccnc(NC(=O)C2CC(F)(F)C2)c1]

Methyl 2-(3,3-difluorocyclobutanecarboxamido) isonicotinate $^1$H NMR (400 MHz, Chloroform-d) δ ppm 8.77 (br. s., 1H) 8.43 (dd, J=5.14, 0.73 Hz, 1H) 8.07 (br. s., 1H) 7.66 (dd, J=5.14, 1.47 Hz, 1H) 3.98 (s, 3H) 2.96-3.10 (m, 3H) 2.76-2.93 (m, 2H).

Methyl 2-(3,3-difluorocyclobutanecarboxamido) isonicotinate

To methyl 2-(cyclobutanecarboxamido)isonicotinate (0.5 g, 2.134 mmol) in tetrahydrofuran (3 mL) and methanol (0.5 ml) was added LiOH, 2N (3 ml, 6.00 mmol). The reaction mixture was stirred at rt overnight. The solvent was removed and the residue was redissolved in ethyl acetate, neutralized with 1N HCl: White solid precipitated out. The mixture was filtered, the solid was washed with water and methanol and dried to give the desired product (0.15 g, 0.477 mmol, 22% yield). $^1$H NMR (500 MHz, DMSO-d$_6$) δ ppm 13.61 (br. s., 1H) 10.55 (s, 1H) 8.63 (s, 1H) 8.47 (d, J=4.88 Hz, 1H) 7.50 (dd, J=5.04, 1.37 Hz, 1H) 3.40 (t, J=8.39 Hz, 1H) 2.18-2.28 (m, 2H) 2.07-2.16 (m, 2H) 1.90-2.01 (m, 1H) 1.78-1.86 (m, 1H).

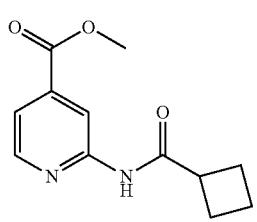 [SMILES: COC(=O)c1ccnc(NC(=O)C2CCC2)c1]

Methyl 2-(cyclobutanecarboxamido)isonicotinate

To a solution of methyl 2-aminoisonicotinate (1.0 g, 6.57 mmol) in methylene chloride (25 mL) was added pyridine (6 mL, 74.2 mmol), and then cyclobutanecarbonyl chloride (0.935 g, 7.89 mmol) was added dropwise. The reaction was stirred at rt overnight. The solvent was removed. The crude product was purified by silica gel chromatography, eluting

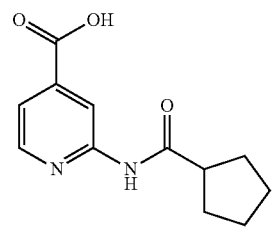 [SMILES: O=C(O)c1ccnc(NC(=O)C2CCCC2)c1]

2-(cyclopentanecarboxamido)isonicotinic Acid

MS (ESI) (m/z): 235.1 (M+H)$^+$.

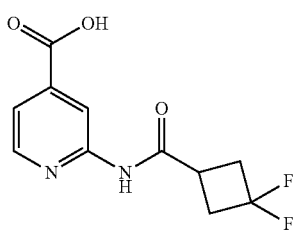 [SMILES: O=C(O)c1ccnc(NC(=O)C2CC(F)(F)C2)c1]

2-(3,3-difluorocyclobutanecarboxamido)isonicotinic Acid

MS (ESI) (m/z): 257.1 (M+H)+.

Example 30

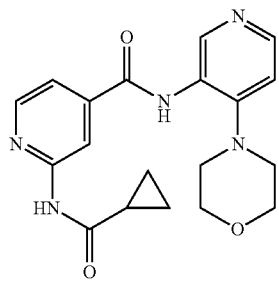 [SMILES: O=C(Nc1cnccc1N1CCOCC1)c1ccnc(NC(=O)C2CC2)c1]

2-(Cyclopropanecarboxamido)-N-(4-morpholinopyridin-3-yl)isonicotinamide

A 100 mL round-bottom flask was charged with 2-(cyclopropanecarboxamido)isonicotinic acid (28.1 mg, 0.136 mmol) in methylene chloride (1 mL) to give a white suspension. dimethylformamide (2.110 μl, 0.027 mmol) (one drop) and oxalyl chloride (0.014 mL, 0.164 mmol) were added. The mixture was stirred at rt for 30 min. 4-Morpholinopyridin-3-amine (24.42 mg, 0.136 mmol) and triethylamine (0.057 mL, 0.409 mmol) were added. The mixture was stirred at rt for 2 h. It was then concentrated, re-dissolved in 1.5 ml dimethylformamide, and purified by prep-HPLC to afford the desired product (7.2 mg, 14%): MS (ESI) (m/z): 368 (M+H)+; $^1$H NMR (400 MHz, DMSO) δ 11.00 (s, 1H), 10.05 (s, 1H), 8.56 (s, 1H), 8.51 (d, J=5.0 Hz, 1H), 8.47 (s, 1H), 8.29 (d, J=5.5 Hz, 1H), 7.55 (d, J=4.4 Hz, 1H), 7.04 (d, J=5.5 Hz, 1H), 3.80-3.66 (m, 4H), 3.18-3.05 (m, 4H), 2.06 (tt, J=6.9, 5.3 Hz, 1H), 0.97-0.84 (m, 4H).

Example 20

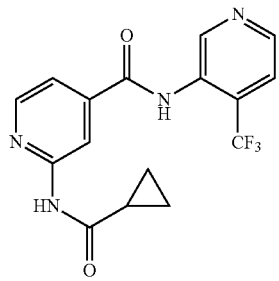 [SMILES: O=C(Nc1cnccc1C(F)(F)F)c1ccnc(NC(=O)C2CC2)c1]

2-(Cyclopropanecarboxamido)-N-(4-(trifluoromethyl)pyridin-3-yl)isonicotinamide

MS (ESI) (m/z): 351 (M+H)+; $^1$H NMR (500 MHz, DMSO-d$_6$) δ 11.04 (s, 1H), 10.80-10.64 (s, br, 1H), 8.85 (s, 1H), 8.78 (d, J=4.9 Hz, 1H), 8.59 (s, 1H), 8.53 (d, J=5.2 Hz, 1H), 7.85 (d, J=4.9 Hz, 1H), 7.56 (dd, J=5.0, 1.4 Hz, 1H), 2.12-2.01 (m, 1H), 0.92-0.82 (m, 4H).

Example 40

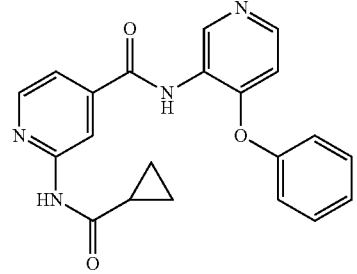 [SMILES: O=C(Nc1cnccc1Oc1ccccc1)c1ccnc(NC(=O)C2CC2)c1]

2-(Cyclopropanecarboxamido)-N-(4-phenoxypyridin-3-yl)isonicotinamide

MS (ESI) (m/z): 375 (M+H)+; $^1$H NMR (500 MHz, DMSO) δ 11.02 (s, 1H), 10.41 (s, 1H), 8.71 (s, 1H), 8.55 (s, 1H), 8.52-8.43 (m, 1H), 8.34 (d, J=5.6 Hz, 1H), 7.54-7.50 (m, 1H), 7.50-7.45 (m, 2H), 7.31-7.25 (m, 1H), 7.20-7.15 (m, 2H), 6.79 (d, J=5.6 Hz, 1H), 2.09-1.99 (m, 1H), 0.88-0.79 (m, 4H).

Example 59

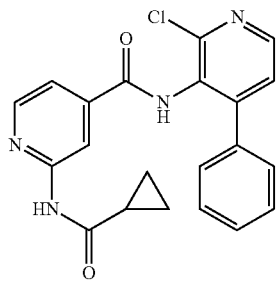 [SMILES: O=C(Nc1c(-c2ccccc2)ccnc1Cl)c1ccnc(NC(=O)C2CC2)c1]

N-(2-chloro-4-phenylpyridin-3-yl)-2-(cyclopropanecarboxamido)isonicotinamide

MS (ESI) (m/z): 393 (M+H)+; $^1$H NMR (500 MHz, DMSO) δ 10.99 (s, 1H), 10.59 (s, 1H), 8.46 (s, 3H), 7.56-7.50 (m, 3H), 7.46-7.37 (m, 4H), 2.07-1.99 (m, 1H), 0.88-0.81 (m, 4H).

Example 19

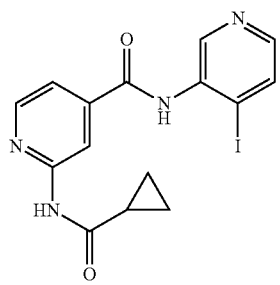 [SMILES: O=C(Nc1cnccc1I)c1ccnc(NC(=O)C2CC2)c1]

2-(Cyclopropanecarboxamido)-N-(4-iodopyridin-3-yl)isonicotinamide

A 250 mL round-bottom flask was charged with 2-(cyclopropanecarboxamido)isonicotinic acid (776.5 mg, 3.77 mmol) in methylene chloride (30 mL) to give a white suspension. After cooling to 0° C., dimethylformamide (0.029 mL, 0.377 mmol) and oxalyl chloride (0.363 mL, 4.14 mmol) were added. The mixture was stirred at 0° C. for 2 h. 4-Iodopyridin-3-amine (829 mg, 3.77 mmol) was added at 0° C., followed by triethylamine (2.1 mL, 15.06 mmol). The mixture became homogenous. It was then concentrated to give a tan oil. The residue was purified by flash column chromatography on silica gel, eluting with 0-10% methanol/methylene chloride (containing 1% acetic acid), giving a tan solid (100%) which was used without further characterization.

Example 31

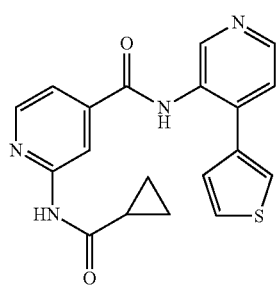 [SMILES: O=C(Nc1cnccc1-c1ccsc1)c1ccnc(NC(=O)C2CC2)c1]

2-(Cyclopropanecarboxamido)-N-(4-(thiophen-3-yl)pyridin-3-yl)isonicotinamide

In a 5 mL microwave tube under nitrogen was added 2-(cyclopropanecarboxamido)-N-(4-iodopyridin-3-yl)isonicotinamide (40 mg, 0.098 mmol), thiophen-3-ylboronic acid (18.81 mg, 0.147 mmol), and $Na_2CO_3$ (0.196 mL, 0.392 mmol, 2.0 M in water) in dioxane (1 mL) to give a tan suspension. $Pd(PPh_3)_4$ (1.132 mg, 0.980 μmol) was added under nitrogen. The vial was sealed and heated at 110° C. using microwaves for 30 min. Volatiles were removed in vacuo and the residue was dissolved in 1.5 mL dimethylformamide and purified by prep-HPLC to afford the desired product (7.6 mg, 21%): MS (ESI) (m/z): 365 (M+H)$^+$; $^1$H NMR (400 MHz, DMSO) δ 10.97 (s, 1H), 10.45 (s, 1H), 8.62 (s, 1H), 8.57-8.46 (m, 3H), 7.93 (dd, J=2.9, 1.3 Hz, 1H), 7.65 (dd, J=5.0, 2.9 Hz, 1H), 7.60 (d, J=5.1 Hz, 1H), 7.52 (d, J=4.4 Hz, 1H), 7.44 (dd, J=5.0, 1.3 Hz, 1H), 2.12-1.97 (m, 1H), 0.85 (dd, J=11.1, 3.5 Hz, 4H).

Example 32

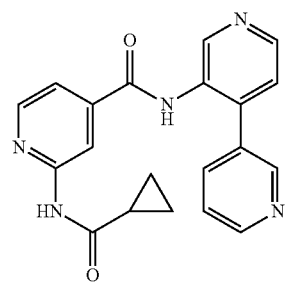

N-([3,4'-bipyridin]-3'-yl)-2-(cyclopropanecarboxamido)isonicotinamide

MS (ESI) (m/z): 360 (M+H)$^+$; $^1$H NMR (400 MHz, DMSO) δ 10.95 (s, 1H), 10.50 (s, 1H), 8.69 (d, J=2.7 Hz, 2H), 8.61 (d, J=5.0 Hz, 1H), 8.58 (dd, J=4.8, 1.6 Hz, 1H), 8.49-8.41 (m, 2H), 7.96-7.90 (m, 1H), 7.56 (d, J=5.0 Hz, 1H), 7.47 (ddd, J=7.9, 4.8, 0.7 Hz, 1H), 7.39 (d, J=5.1 Hz, 1H), 2.09-1.99 (m, 1H), 0.85 (dd, J=6.2, 3.8 Hz, 4H).

Example 33

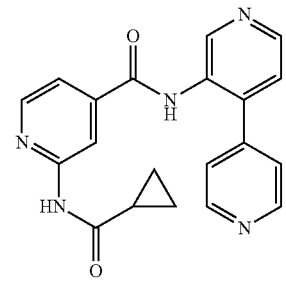 [SMILES: O=C(Nc1cnccc1-c1ccncc1)c1ccnc(NC(=O)C2CC2)c1]

N-([4,4'-bipyridin]-3-yl)-2-(cyclopropanecarboxamido)isonicotinamide

MS (ESI) (m/z): 360 (M+H)$^+$; $^1$H NMR (400 MHz, DMSO) δ 10.97 (s, 1H), 10.52 (s, 1H), 8.71 (s, 1H), 8.68-8.58 (m, 3H), 8.51-8.40 (m, 2H), 7.60-7.46 (m, 3H), 7.40 (dd, J=5.1, 1.3 Hz, 1H), 2.04 (dq, J=7.3, 5.4 Hz, 1H), 0.90-0.82 (m, 4H).

Example 34

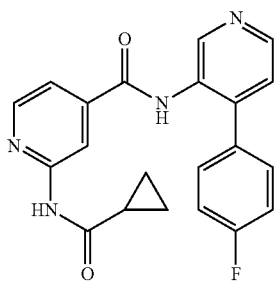 [SMILES: O=C(Nc1cnccc1-c1ccc(F)cc1)c1ccnc(NC(=O)C2CC2)c1]

2-(Cyclopropanecarboxamido)-N-(4-(4-fluorophenyl)pyridin-3-yl)isonicotinamide

MS (ESI) (m/z): 377 (M+H)$^+$; $^1$H NMR (500 MHz, DMSO) δ 11.00 (s, 1H), 10.42 (s, 1H), 8.65 (s, 1H), 8.57 (d, J=5.0 Hz, 1H), 8.50-8.41 (m, 2H), 7.56 (dd, J=8.7, 5.5 Hz, 2H), 7.49 (d, J=5.0 Hz, 1H), 7.40 (d, J=4.7 Hz, 1H), 7.35-7.24 (m, 2H), 2.10-1.98 (m, 1H), 0.88-0.82 (m, 4H).

Example 35

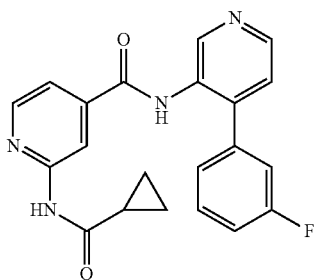 [SMILES: O=C(Nc1cnccc1-c1cccc(F)c1)c1ccnc(NC(=O)C2CC2)c1]

2-(Cyclopropanecarboxamido)-N-(4-(3-fluorophenyl)pyridin-3-yl)isonicotinamide

MS (ESI) (m/z): 377 (M+H)$^+$; $^1$H NMR (500 MHz, DMSO) δ 11.00 (s, 1H), 10.47 (s, 1H), 8.66 (s, 1H), 8.59 (d, J=5.0 Hz, 1H), 8.49-8.43 (m, 2H), 7.52 (d, J=5.0 Hz, 1H), 7.51-7.44 (m, 1H), 7.40 (d, J=4.9 Hz, 1H), 7.35 (d, J=8.0 Hz, 2H), 7.27-7.21 (m, 1H), 2.08-1.99 (m, 1H), 0.89-0.81 (m, 4H).

Example 38

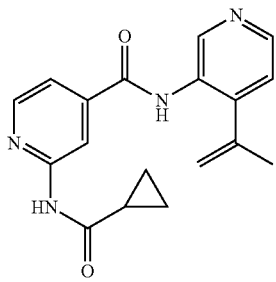 [SMILES: C=C(C)c1ccncc1NC(=O)c1ccnc(NC(=O)C2CC2)c1]

2-(Cyclopropanecarboxamido)-N-(4-(prop-1-en-2-yl)pyridin-3-yl)isonicotinamide

MS (ESI) (m/z): 323 (M+H)$^+$; $^1$H NMR (400 MHz, DMSO) δ 10.98 (s, 1H), 10.29 (s, 1H), 8.54 (d, J=5.8 Hz, 2H), 8.50 (d, J=5.1 Hz, 1H), 8.46 (d, J=5.0 Hz, 1H), 7.52 (dd, J=5.1, 1.4 Hz, 1H), 7.37 (d, J=5.0 Hz, 1H), 5.31-5.20 (m, 1H), 5.11 (dd, J=1.6, 0.9 Hz, 1H), 2.10-2.01 (m, 4H), 0.86 (dd, J=8.5, 2.3 Hz, 4H).

Example 39

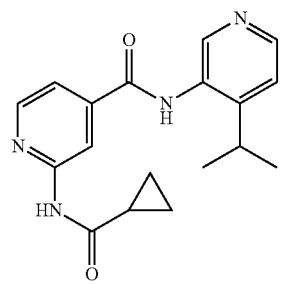 [SMILES: CC(C)c1ccncc1NC(=O)c1ccnc(NC(=O)C2CC2)c1]

2-(Cyclopropanecarboxamido)-N-(4-isopropylpyridine-3-yl)isonicotinamide

MS (ESI) (m/z): 325 (M+H)$^+$; $^1$H NMR (400 MHz, DMSO) δ 11.00 (s, 1H), 10.33 (s, 1H), 8.58 (s, 1H), 8.52 (d, J=5.0 Hz, 1H), 8.45 (d, J=5.1 Hz, 1H), 8.41 (s, 1H), 7.59 (d, J=4.5 Hz, 1H), 7.43 (d, J=5.1 Hz, 1H), 3.22-3.06 (m, 1H), 2.13-2.00 (m, 1H), 1.20-1.16 (m, 6H), 0.86 (d, J=8.2 Hz, 4H).

Example 42

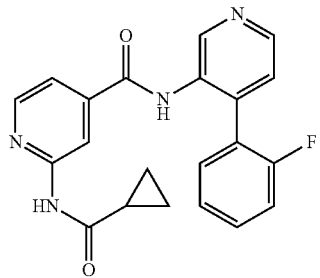 [SMILES: O=C(Nc1cnccc1-c1ccccc1F)c1ccnc(NC(=O)C2CC2)c1]

2-(Cyclopropanecarboxamido)-N-(4-(2-fluorophenyl)pyridin-3-yl)isonicotinamide

MS (ESI) (m/z): 377 (M+H)$^+$; $^1$H NMR (500 MHz, DMSO) δ 10.98 (s, 1H), 10.41 (s, 1H), 8.70 (s, 1H), 8.58 (d, J=5.0 Hz, 1H), 8.43 (d, J=5.2 Hz, 1H), 8.40 (s, 1H), 7.49 (d, J=5.0 Hz, 1H), 7.47-7.38 (m, 2H), 7.35-7.22 (m, 3H), 2.03 (dq, J=7.1, 5.4 Hz, 1H), 0.89-0.81 (m, 4H).

Example 47

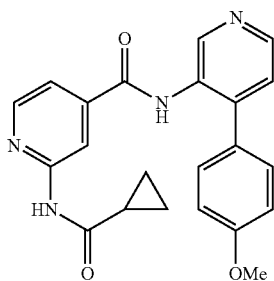 [SMILES: COc1ccc(-c2ccncc2NC(=O)c2ccnc(NC(=O)C3CC3)c2)cc1]

2-(Cyclopropanecarboxamido)-N-(4-(4-methoxyphenyl)pyridine-3-yl)isonicotinamide

MS (ESI) (m/z): 389 (M+H)$^+$; $^1$H NMR (500 MHz, DMSO) δ 11.01 (s, 1H), 10.38 (s, 1H), 8.60 (s, 1H), 8.54 (d, J=5.0 Hz, 1H), 8.47 (d, J=5.0 Hz, 2H), 7.47 (dd, J=9.8, 6.9 Hz, 3H), 7.43 (d, J=6.2 Hz, 1H), 7.05-7.01 (m, 2H), 3.79 (s, 3H), 2.10-1.96 (m, 1H), 0.91-0.79 (m, 4H).

Example 48

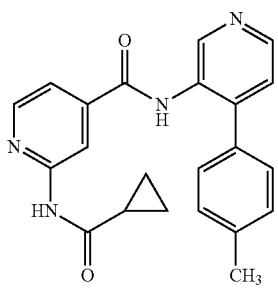

2-(Cyclopropanecarboxamido)-N-(4-(4-(methyl)phenyl)pyridin-3-yl)isonicotinamide

MS (ESI) (m/z): 373 (M+H)$^+$; $^1$H NMR (500 MHz, DMSO) δ 11.00 (s, 1H), 10.38 (s, 1H), 8.62 (s, 1H), 8.56 (d, J=5.0 Hz, 1H), 8.51-8.42 (m, 2H), 7.47 (d, J=5.0 Hz, 1H), 7.42 (d, J=7.8 Hz, 3H), 7.27 (d, J=7.9 Hz, 2H), 2.32 (s, 3H), 2.10-1.99 (m, 1H), 0.90-0.80 (m, 4H).

Example 49

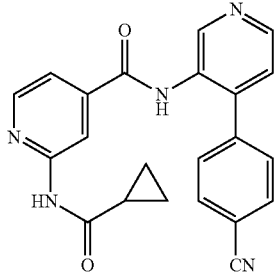 [SMILES: O=C(Nc1cnccc1-c1ccc(Cl)cc1)c1ccnc(NC(=O)C2CC2)c1]

N-(4-(4-cyanophenyl)pyridin-3-yl)-2-(cyclopropanecarboxamido)isonicotinamide

MS (ESI) (m/z): 384 (M+H)$^+$; $^1$H NMR (500 MHz, DMSO) δ 11.01 (s, 1H), 10.50 (s, 1H), 8.72 (s, 1H), 8.61 (d, J=5.0 Hz, 1H), 8.46 (d, J=5.1 Hz, 1H), 8.40 (s, 1H), 7.95-7.90 (m, 2H), 7.70 (d, J=8.4 Hz, 2H), 7.53 (d, J=5.1 Hz, 1H), 7.39 (d, J=4.0 Hz; 1H), 2.09-1.99 (m, 1H), 0.86 (dtd, J=8.0, 5.0, 3.1 Hz, 4H).

Example 51

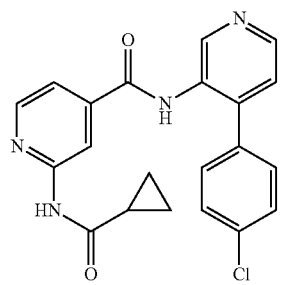

N-(4-(4-chlorophenyl)pyridin-3-yl)-2-(cyclopropanecarboxamido)isonicotinamide

MS (ESI) (m/z): 393 (M+H)$^+$; $^1$H NMR (500 MHz, DMSO) δ 11.01 (s, 1H), 10.44 (s, 1H), 8.67 (s, 1H), 8.58 (d, J=5.0 Hz, 1H), 8.52-8.40 (m, 2H), 7.56-7.51 (m, 4H), 7.50 (d, J=5.1 Hz, 1H), 7.41 (d, J=4.0 Hz, 1H), 2.04 (dq, J=7.5, 5.0 Hz, 1H), 0.92-0.80 (m, 4H).

Example 55

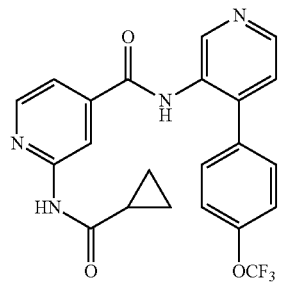

2-(Cyclopropanecarboxamido)-N-(4-(4-(trifluoromethoxy)phenyl)pyridin-3-yl)isonicotinamide MS (ESI) (m/z): 443 (M+H)$^+$; $^1$H NMR (500 MHz, DMSO) δ 11.01 (s, 1H), 10.46 (s, 1H), 8.71 (s, 1H), 8.61 (d, J=5.1 Hz, 1H), 8.46 (d, J=5.2 Hz, 1H), 8.44 (s, 1H), 7.66 (s, 1H), 7.64 (s, 1H), 7.55 (d, J=5.0 Hz, 1H), 7.48 (s, 1H), 7.46 (s, 1H), 7.38 (d, J=5.0 Hz, 1H), 2.10-1.98 (m, 1H), 0.92-0.79 (m, 4H).

Example 56

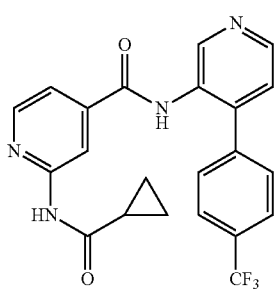 [SMILES: O=C(Nc1cnccc1-c1ccc(C(F)(F)F)cc1)c1ccnc(NC(=O)C2CC2)c1]

2-(Cyclopropanecarboxamido)-N-(4-(4-(trifluoromethyl)phenyl)pyridin-3-yl)isonicotinamide MS (ESI) (m/z): 427 (M+H)+; 1H NMR (500 MHz, DMSO) δ 11.02 (s, 1H), 10.49 (s, 1H), 8.74 (s, 1H), 8.62 (d, J=5.0 Hz, 1H), 8.46 (d, J=5.1 Hz, 1H), 8.43 (s, 1H), 7.85 (d, J=8.2 Hz, 2H), 7.74 (d, J=8.1 Hz, 2H), 7.55 (d, J=5.0 Hz, 1H), 7.39 (d, J=3.9 Hz, 111H), 2.10-1.95 (m, 1H), 0.91-0.81 (m, 4H).

Example 64

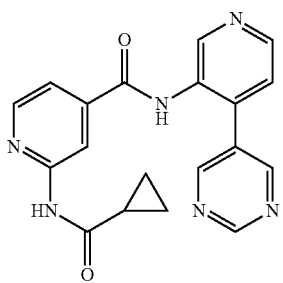

2-(Cyclopropanecarboxamido)-N-(4-(pyrimidin-5-yl)pyridin-3-yl)isonicotinamide

MS (ESI) (m/z): 361 (M+H)+; 1H NMR (500 MHz, DMSO-d6) δ 10.99 (s, 1H), 9.1.9 (s, 1H), 8.94 (s, 2H), 8.74 (s, 1H), 8.63 (d, J=4.9 Hz, 1H), 8.46 (d, J=5.2 Hz, 1H), 8.43 (s, 1H), 7.63 (d, J=5.2 Hz, 1H), 7.41 (d, J=4.9 Hz, 1H), 2.03 (t, J=6.1 Hz, 1H), 0.87-0.81 (m, 4H).

Example 65

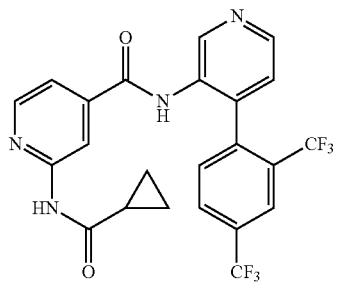 [SMILES: O=C(Nc1cnccc1-c1ccc(C(F)(F)F)cc1C(F)(F)F)c1ccnc(NC(=O)C2CC2)c1]

N-(4-(2,4-bis(trifluoromethyl)phenyl)pyridin-3-yl)-2-(cyclopropanecarboxamido)isonicotinamide MS (ESI) (m/z): 495 (M+H)+; 1H NMR (500 MHz, DMSO-d6) δ 10.95 (s, 1H), 8.84 (s, 1H), 8.40 (d, J=4.9 Hz, 1H), 8.23 (s, 1H), 8.18-8.12 (m, 2H), 7.67 (d, J=7.9 Hz, 1H), 7.41 (d, J=5.2 Hz, 1H), 7.24 (dd, J=5.0, 1.4 Hz, 1H), 2.01 (t, J=5.8 Hz, 1H), 0.86-0.81 (m, 4H).

Example 66

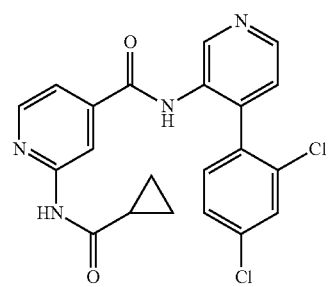 [SMILES: O=C(Nc1cnccc1-c1ccc(Cl)cc1Cl)c1ccnc(NC(=O)C2CC2)c1]

2-(Cyclopropanecarboxamido)-N-(4-(2,4-dichlorophenyl)pyridin-3-yl)isonicotinamide MS (ESI) (m/z): 427 (M+H)+; 1H NMR (500 MHz, DMSO-d6) δ 10.98 (s, 1H), 10.34 (br. s., 1H), 8.77 (s, 1H), 8.58 (d, J=5.2 Hz, 1H), 8.44 (d, J=4.9 Hz, 1H), 8.35 (s, 1H), 7.73 (d, J=1.8 Hz, 1H), 7.51 (dd, J=8.2, 2.1 Hz, 1H), 7.43 (d, J=5.2 Hz, 1H), 7.39 (d, J=8.2 Hz, 1H), 7.31 (d, J=4.0 Hz, 1H), 2.06-1.99 (m, 1H), 0.89-0.82 (m, 4H).

Example 67

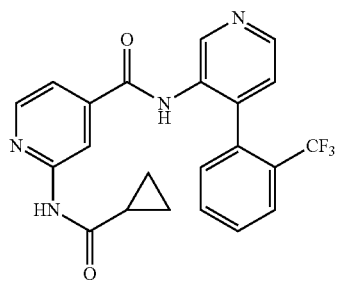 [SMILES: O=C(Nc1cnccc1-c1ccccc1C(F)(F)F)c1ccnc(NC(=O)C2CC2)c1]

2-(Cyclopropanecarboxamido)-N-(4-(2-(trifluoromethyl)phenyl)pyridin-3-yl)isonicotinamide MS (ESI) (m/z): 427 (M+H)+; 1H NMR (500 MHz, DMSO-d6) δ 10.95 (s, 1H), 10.19 (s, 1H), 8.72 (s, 1H), 8.56 (d, J=4.9 Hz, 1H), 8.39 (d, J=5.2 Hz, 1H), 8.31 (s, 1H), 7.83 (d, J=7.6 Hz, 1H), 7.73-7.67 (m, 1H), 7.65-7.59 (m, 1H), 7.40 (d, J=7.6 Hz, 1H), 7.36 (d, J=5.2 Hz, 1H), 7.20 (dd, J=5.0, 1.4 Hz, 1H), 2.05-1.98 (m, 1H), 0.86-0.81 (m, 4H).

Example 68

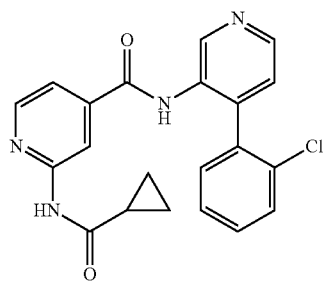 [SMILES: O=C(Nc1cnccc1-c1ccccc1Cl)c1ccnc(NC(=O)C2CC2)c1]

2-(Cyclopropanecarboxamido)-N-(4-(2-chlorophenyl)pyridin-3-yl)isonicotinamide

MS (ESI) (m/z): 393 (M+H)$^+$; $^1$H NMR (500 MHz, DMSO-d$_6$) δ 11.02 (s, 1H), 10.58 (s, 1H), 8.94 (s, 1H), 8.72 (d, J=5.2 Hz, 1H), 8.44 (d, J=5.2 Hz, 1H), 8.37 (s, 1H), 7.71 (d, J=5.5 Hz, 1H), 7.60-7.56 (m, 1H), 7.48-7.40 (m, 3H), 7.30 (dd, J=5.2, 1.2 Hz, 1H), 2.03 (quin, =6.2 Hz, 1H), 0.86-0.83 (m, 4H).

Example 69

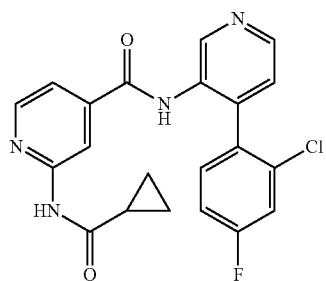 [SMILES: O=C(Nc1cnccc1-c1ccc(F)cc1Cl)c1ccnc(NC(=O)C2CC2)c1]

N-(4-(2-chloro-4-fluorophenyl)pyridin-3-yl)-2-(cyclopropanecarboxamido)isonicotinamide MS (ESI) (m/z): 393 (M+H)$^+$; $^1$H NMR (500 MHz, DMSO-d$_6$) δ 10.98 (s, 1H), 10.32 (br. s., 1H), 8.75 (s, 1H), 8.57 (d, J=4.9 Hz, 1H), 8.43 (d, J=5.2 Hz, 1H), 8.35 (s, 1H), 7.55 (dd, J=9.0, 2.6 Hz, 1H), 7.45-7.39 (m, 2H), 7.34-7.27 (m, 2H), 2.05-1.99 (m, 1H), 0.87-0.83 (m, 4H).

Example 70

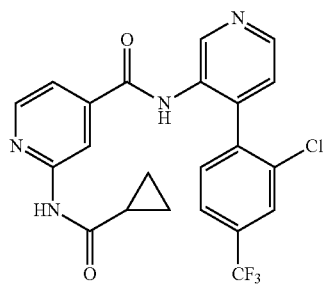 [SMILES: O=C(Nc1cnccc1-c1ccc(C(F)(F)F)cc1Cl)c1ccnc(NC(=O)C2CC2)c1]

N-(4-(2-chloro-4-(trifluoromethyl)phenyl)pyridin-3-yl)-2-(cyclopropanecarboxamido)isonicotinamide MS (ESI) (m/z): 461 (M+H)$^+$; $^1$H NMR (500 MHz, DMSO-d$_6$) δ 10.98 (s, 1H), 10.39 (s, 1H), 8.82 (s, 1H), 8.61 (d, J=4.9 Hz, 1H), 8.43 (d, J=4.9 Hz, 1H), 8.31 (s, 1H), 7.99 (s, 1H), 7.81 (d, J=7.0 Hz, 1H), 7.61 (d, J=7.9 Hz, 1H), 7.48 (d, J=4.9 Hz, 1H), 7.30 (d, J=4.0 Hz, 1H), 2.02 (quin, J=6.2 Hz, 1H), 0.87-0.81 (m, 4H).

Example 71

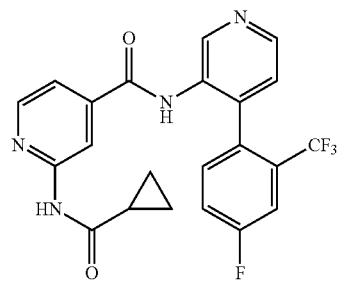 [SMILES: O=C(Nc1cnccc1-c1ccc(F)cc1C(F)(F)F)c1ccnc(NC(=O)C2CC2)c1]

2-(Cyclopropanecarboxamido)-N-(4-(4-fluoro-2-(trifluoromethyl)phenyl)pyridin-3-yl)isonicotinamide MS (ESI) (m/z): 445 (M+H)$^+$; $^1$H NMR (500 MHz, DMSO-d$_6$) δ 10.96 (s, 11H), 10.17 (br. s., 1H), 8.77 (s, 1H), 8.55 (d, J=5.2 Hz, 1H), 8.41 (d, J=4.9 Hz, 1H), 8.28 (s, 1H), 7.75 (dd, J=9.3, 2.6 Hz, 1H), 7.60 (td, J=8.5, 2.6 Hz, 1H), 7.46 (dd, J=8.7, 5.6 Hz, 1H), 7.36 (d, J=4.9 Hz, 1H), 7.23 (dd, J=5.2, 1.2 Hz, 1H), 2.06-1.96 (m, 1H), 0.87-0.81 (m, 4H).

Example 72

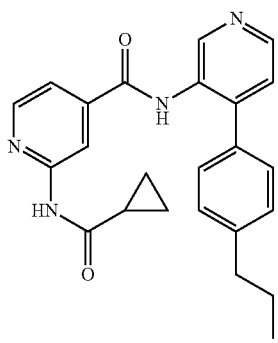 [SMILES: CCCc1ccc(-c2ccncc2NC(=O)c2ccnc(NC(=O)C3CC3)c2)cc1]

2-(Cyclopropanecarboxamido)-N-(4-(4-propylphenyl)pyridin-3-yl)isonicotinamide

MS (ESI) (m/z): 401 (M+H)$^+$; $^1$H NMR (500 MHz, DMSO-d$_6$) δ 10.99 (br. s., 1H), 10.37 (br. s., 1H), 8.63 (s, 1H), 8.56 (d, J=4.9 Hz, 1H), 8.49-8.42 (m, 2H), 7.48 (d, J=5.2 Hz, 1H), 7.44 (d, J=8.2 Hz, 2H), 7.40 (d, J=4.9 Hz, 1H), 7.28 (d, J=8.2 Hz, 2H), 2.60-2.55 (m, 2H), 2.04 (quin, J=6.2 Hz, 1H), 1.60 (sxt, J=7.4 Hz, 2H), 0.90 (t, J=7.3 Hz, 3H), 0.86-0.83 (m, 4H).

Example 73

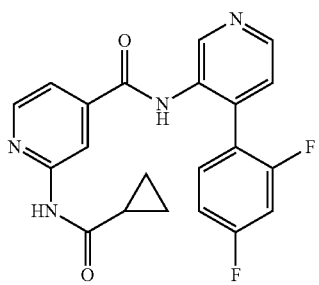 [SMILES: O=C(Nc1cnccc1-c1ccc(F)cc1F)c1ccnc(NC(=O)C2CC2)c1]

2-(Cyclopropanecarboxamido)-N-(4-(2,4-difluorophenyl)pyridin-3-yl)isonicotinamide MS (ESI) (m/z): 395 (M+H)$^+$; $^1$H NMR (500 MHz, DMSO-d$_6$) δ 10.99 (s, 1H), 10.40 (br. s., 1H), 8.73 (s, 1H), 8.58 (d, J=4.9 Hz, 1H), 8.45 (d, J=4.9 Hz, 1H), 8.39 (s, 1H), 7.51-7.43 (m, 2H), 7.39-7.29 (m, 2H), 7.18 (td, J=8.5, 2.4 Hz, 1H), 2.09-2.00 (m, 1H), 0.89-0.80 (m, 4H).

Example 74

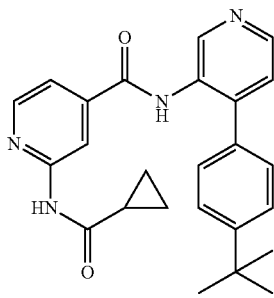 [SMILES: CC(C)(C)c1ccc(-c2ccncc2NC(=O)c2ccnc(NC(=O)C3CC3)c2)cc1]

N-(4-(4-(tert-butyl)phenyl)pyridin-3-yl)-2-(cyclopropanecarboxamido)isonicotinamide MS (ESI) (m/z): 415 (M+H)$^+$; $^1$H NMR (500 MHz, DMSO-d$_6$) δ 11.00 (s, 1H), 10.38 (s, 1H), 8.65 (s, 1H), 8.55 (d, J=5.2 Hz, 1H), 8.49-8.43 (m, 2H), 7.54-7.46 (m, 5H), 7.41 (d, J=4.6 Hz, 1H), 2.08-1.99 (m, 1H), 1.30 (s, 9H), 0.87-0.82 (m, 4H).

Example 75

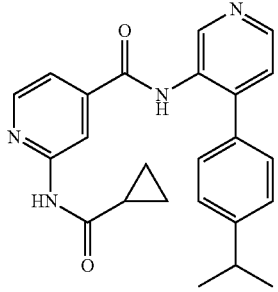 [SMILES: CC(C)c1ccc(-c2ccncc2NC(=O)c2ccnc(NC(=O)C3CC3)c2)cc1]

2-(Cyclopropanecarboxamido)-N-(4-(4-isopropylphenyl)pyridine-3-yl)isonicotinamide MS (ESI) (m/z): 401 (M+H)$^+$; $^1$H NMR (500 MHz, DMSO-d$_6$) δ 11.00 (s, 1H), 10.40 (br. s., 1H), 8.64 (s, 1H), 8.55 (d, J=4.9 Hz, 1H), 8.48-8.43 (m, 2H), 7.51-7.44 (m, 3H), 7.41 (d, J=4.3 Hz, 1H), 7.35 (d, J=8.2 Hz, 2H), 2.96-2.86 (m, 1H), 2.09-2.00 (m, 1H), 1.22 (d, J=6.7 Hz, 6H), 0.88-0.81 (m, 4H).

Example 76

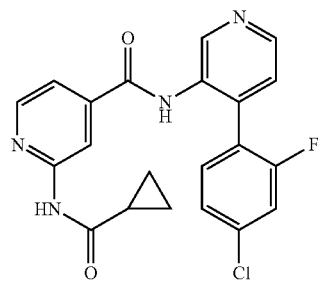 [SMILES: O=C(Nc1cnccc1-c1ccc(Cl)cc1F)c1ccnc(NC(=O)C2CC2)c1]

N-(4-(4-chloro-2-fluorophenyl)pyridin-3-yl)-2-(cyclopropanecarboxamido)isonicotinamide MS (ESI) (m/z): 411 (M+H)$^+$; $^1$H NMR (500 MHz, DMSO-d$_6$) δ 11.00 (s, 1H), 10.42 (br. s., 1H), 8.75 (s, 1H), 8.57 (d, J=4.9 Hz, 1H), 8.45 (d, J=5.2 Hz, 1H), 8.39 (s, 1H), 7.55 (dd, J=10.1, 2.1 Hz, 1H), 7.50-7.43 (m, 2H), 7.41-7.32 (m, 2H), 2.08-1.99 (m, 1H), 0.90-0.82 (m, 4H).

Example 81

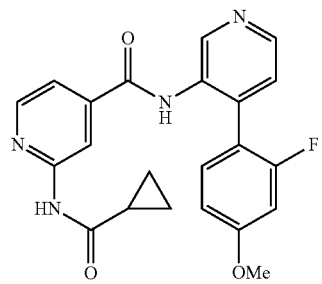 [SMILES: COc1ccc(-c2ccncc2NC(=O)c2ccnc(NC(=O)C3CC3)c2)c(F)c1]

2-(Cyclopropanecarboxamido)-N-(4-(2-fluoro-4-methoxyphenyl)pyridin-3-yl)isonicotinamide MS (ESI) (m/z): 407 (M+H)$^+$; $^1$H NMR (500 MHz, DMSO-d$_6$) δ 10.98 (s, 1H), 10.33 (br. s., 1H), 8.69 (s, 1H), 8.53 (d, J=4.9 Hz, 1H), 8.45 (d, J=5.2 Hz, 1H), 8.40 (s, 1H), 7.44 (d, J=4.9 Hz, 1H), 7.39-7.31 (m, 2H), 6.94 (dd, J=12.5, 2.4 Hz, 1H), 6.87 (dd, J=8.9, 2.4 Hz, 1H), 3.80 (s, 3H), 2.08-2.00 (m, 1H), 0.88-0.81 (m, 4H).

Example 82

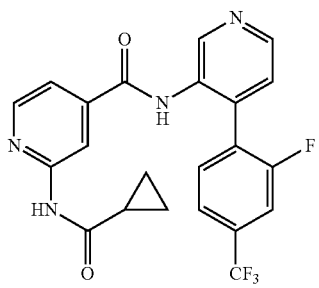 [SMILES: O=C(Nc1cnccc1-c1ccc(C(F)(F)F)cc1F)c1ccnc(NC(=O)C2CC2)c1]

2-(Cyclopropanecarboxamido)-N-(4-(2-fluoro-4-(trifluoromethyl)phenyl)pyridine-3-yl)isonicotinamide MS (ESI) (m/z): 445 (M+H)⁺; ¹H NMR (500 MHz, DMSO-d₆) δ 10.98 (s, 1H), 10.47 (br. s., 1H), 8.82 (s, 1H), 8.60 (d, J=4.9 Hz, 1H), 8.44 (d, J=4.9 Hz, 1H), 8.36 (s, 1H), 7.81 (d, J=10.1 Hz, 1H), 7.70-7.64 (m, 2H), 7.54 (d, J=4.9 Hz, 1H), 7.34 (d, J=4.0 Hz, 1H), 2.06-1.98 (m, 1H), 0.88-0.80 (m, 4H).

Example 84

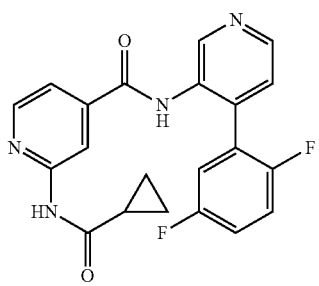 [SMILES: O=C(Nc1cnccc1-c1cc(F)ccc1F)c1ccnc(NC(=O)C2CC2)c1]

2-(Cyclopropanecarboxamido)-N-(4-(2,5-difluoro-phenyl)pyridin-3-yl)isonicotinamide MS (ESI) (m/z): 395 (M+H)⁺; ¹H NMR (500 MHz, DMSO-d₆) δ 10.99 (s, 1H), 10.46 (br. s., 1H), 8.72 (s, 1H), 8.60 (d, J=4.9 Hz, 1H), 8.45 (d, J=5.2 Hz, 1H), 8.40 (s, 1H), 7.51 (d, J=5.2 Hz, 1H), 7.40-7.25 (m, 4H), 2.07-1.98 (m, 1H), 0.87-0.82 (m, 4H).

Example 85

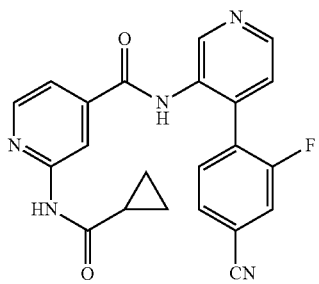

N-(4-(4-cyano-2-fluorophenyl)pyridin-3-yl)-2-(cyclopropanecarboxamido)isonicotinamide MS (ESI) (m/z): 402 (M+H)⁺; ¹H NMR (500 MHz, DMSO-d₆) δ 10.99 (s, 1H), 10.48 (br. s., 1H), 8.79 (s, 1H), 8.61 (d, J=4.9 Hz, 1H), 8.45 (d, J=5.2 Hz, 1H), 8.33 (s, 1H), 7.97 (d, J=9.8 Hz, 1H), 7.79 (d, J=7.9 Hz, 1H), 7.63 (t, J=7.6 Hz, 1H), 7.53 (d, J=4.9 Hz, 1H), 7.33 (d, J=4.6 Hz, 1H), 2.07-1.99 (m, 1H), 0.92-0.79 (m, 4H).

Example 86

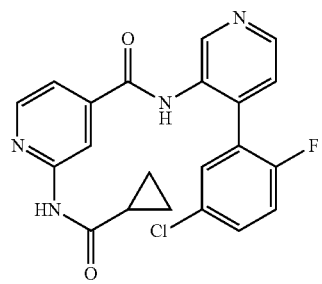 [SMILES: O=C(Nc1cnccc1-c1cc(Cl)ccc1F)c1ccnc(NC(=O)C2CC2)c1]

2-(Cyclopropanecarboxamido)-N-(4-(2-fluoro-5-chloro-phenyl)pyridin-3-yl)isonicotinamide MS (ESI) (m/z): 411 (M+H)⁺; ¹H NMR (500 MHz, DMSO-d₆) δ 10.99 (s, 1H), 10.47 (br. s., 1H), 8.72 (s, 1H), 8.59 (d, J=4.9 Hz, 1H), 8.45 (d, J=5.2 Hz, 1H), 8.40 (s, 1H), 7.51 (dd, J=12.2, 4.9 Hz, 3H), 7.38-7.29 (m, 2H), 2.03 (t, J=5.2 Hz, 1H), 0.87-0.81 (m, 4H).

Example 89

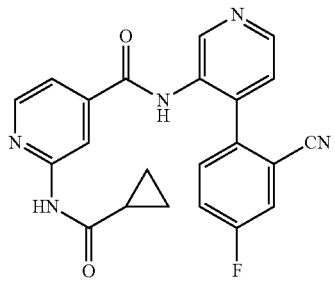 [SMILES: N#Cc1cc(F)ccc1-c1ccncc1NC(=O)c1ccnc(NC(=O)C2CC2)c1]

N-(4-(2-cyano-4-fluorophenyl)pyridin-3-yl)-2-(cyclopropanecarboxamido)isonicotinamide MS (ESI) (m/z): 402 (M+H)⁺; ¹H NMR (500 MHz, DMSO-d₆) δ 11.02 (s, 1H), 9.28 (s, 1H), 9.05 (dd, J=9.0, 5.3 Hz, 1H), 8.76 (d, J=5.5 Hz, 1H), 8.72-8.67 (m, 2H), 8.53 (d, J=4.9 Hz, 1H), 8.13 (d, J=7.9 Hz, 1H), 8.03-7.95 (m, 1H), 7.76 (d, J=4.6 Hz, 1H), 2.12-2.03 (m, 1H), 0.89-0.84 (m, 4H).

Example 91

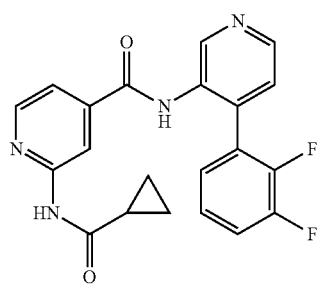 [SMILES: O=C(Nc1cnccc1-c1cccc(F)c1F)c1ccnc(NC(=O)C2CC2)c1]

2-(Cyclopropanecarboxamido)-N-(4-(2,3-difluoro-phenyl)pyridin-3-yl)isonicotinamide MS (ESI) (m/z): 395 (M+H)$^+$; $^1$H NMR (500 MHz, DMSO-d$_6$) δ 10.97 (s, 1H), 8.75 (s, 1H), 8.57 (d, J=4.9 Hz, 1H), 8.43 (d, J=5.2 Hz, 1H), 8.39 (s, 1H), 7.51 (d, J=4.9 Hz, 1H), 7.46 (q, J=8.5 Hz, 1H), 7.34 (d, J=4.6 Hz, 1H), 7.30-7.19 (m, 2H), 2.07-1.99 (m, 1H), 0.87-0.81 (m, 4H).

Example 92

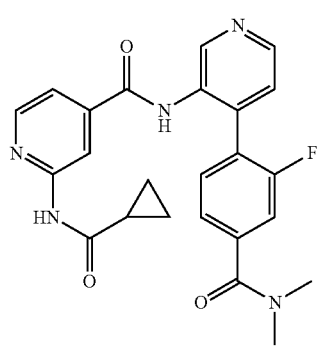 [SMILES: CN(C)C(=O)c1ccc(-c2ccncc2NC(=O)c2ccnc(NC(=O)C3CC3)c2)c(F)c1]

2-(Cyclopropanecarboxamido)-N-(4-(4-(dimethyl-carbamoyl)-2-fluorophenyl)pyridin-3-yl)isonicotina-mide MS (ESI) (m/z): 448 (M+H)$^+$; $^1$H NMR (500 MHz, DMSO-d$_6$) δ 10.98 (s, 1H), 10.48 (s, 1H), 8.80 (s, 1H), 8.63 (d, J=5.2 Hz, 1H), 8.44 (d, J=4.9 Hz, 1H), 8.37 (s, 1H), 7.59 (d, J=5.2 Hz, 1H), 7.48 (t, J=7.6 Hz, 1H), 7.37 (d, J=10.4 Hz, 1H), 7.35-7.28 (m, 2H), 2.99 (s, 3H), 2.87 (s, 3H), 2.02 (quin, J=6.2 Hz, 1H), 0.84 (d, J=6.1 Hz, 4H).

Example 93

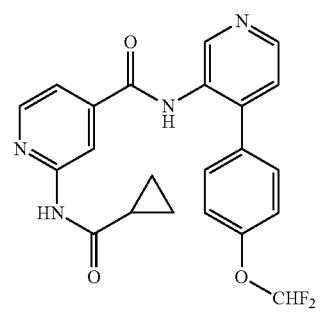 [SMILES: O=C(Nc1cnccc1-c1ccc(OC(F)F)cc1)c1ccnc(NC(=O)C2CC2)c1]

2-(Cyclopropanecarboxamido)-N-(4-(4-(difluo-romethoxy)phenyl)pyridin-3-yl)isonicotinamide MS (ESI) (m/z): 425 (M+H)$^+$; $^1$H NMR (500 MHz, DMSO-d$_6$) δ 11.00 (s, 1H), 10.42 (s, 1H), 8.66 (s, 1H), 8.57 (d, J=4.9 Hz, 1H), 8.46 (d, J=5.2 Hz, 1H), 8.43 (s, 1H), 7.59 (d, J=8.5 Hz, 2H), 7.49 (d, J=4.9 Hz, 1H), 7.41 (d, J=5.2 Hz, 1H), 7.31-7.25 (m, 3H), 2.08-1.99 (m, 1H), 0.88-0.82 (m, 4H).

Example 94

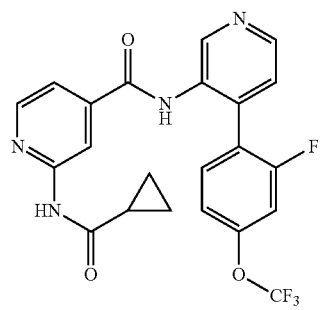 [SMILES: O=C(Nc1cnccc1-c1ccc(OC(F)(F)F)cc1F)c1ccnc(NC(=O)C2CC2)c1]

2-(Cyclopropanecarboxamido)-N-(4-(2-fluoro-4-(trifluoromethoxy)phenyl)pyridin-3-yl)isonicotina-mide MS (ESI) (m/z): 461 (M+H)$^+$; $^1$H NMR (500 MHz, DMSO-d$_6$) δ 10.99 (s, 1H), 10.44 (s, 1H), 8.78 (s, 1H), 8.60 (d, J=4.9 Hz, 1H), 8.44 (d, J=4.9 Hz, 1H), 8.37 (s, 1H), 7.61-7.47 (m, 3H), 7.37-7.29 (m, 2H), 2.07-1.99 (m, 1H), 0.88-0.79 (m, 4H).

Example 95

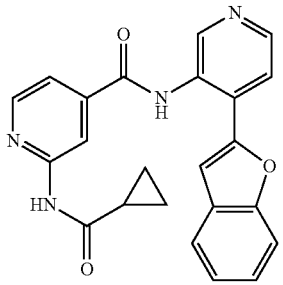 [SMILES: O=C(Nc1cnccc1-c1cc2ccccc2o1)c1ccnc(NC(=O)C2CC2)c1]

N-(4-(benzofuran-2-yl)pyridin-3-yl)-2-(cyclopropanecarboxamido)isonicotinamide

MS (ESI) (m/z): 399 (M+H)$^+$; $^1$H NMR (500 MHz, DMSO-d$_6$) δ 11.09 (s, 1H), 10.74 (br. s., 1H), 8.77 (s, 1H), 8.69 (s, 1H), 8.61 (d, J=5.2 Hz, 1H), 8.57 (d, J=5.2 Hz, 1H), 7.95 (d, J=5.2 Hz, 1H), 7.75 (d, J=7.6 Hz, 1H), 7.66-7.60 (m, 2H), 7.56 (s, 1H), 7.39 (t, J=7.8 Hz, 1H), 7.34-7.28 (m, 1H), 2.12-2.04 (m, 1H), 0.92-0.83 (m, 4H).

Example 96

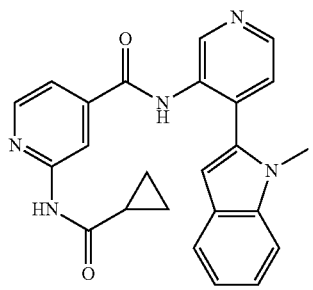 [SMILES: Cn1c(-c2ccncc2NC(=O)c2ccnc(NC(=O)C3CC3)c2)cc2ccccc21]

2-(Cyclopropanecarboxamido)-N-(4-(1-methyl-1H-indol-2-yl)pyridin-3-yl)isonicotinamide MS (ESI) (m/z): 412 (M+H)$^+$; $^1$H NMR (500 MHz, DMSO-d$_6$) δ 10.98 (s, 1H), 10.43 (br. s., 1H), 8.86 (s, 1H), 8.57 (d, J=4.9 Hz, 1H), 8.46 (s, 1H), 8.41 (d, J=5.2 Hz, 1H), 7.59-7.54 (m, 2H), 7.50 (d, J=8.2 Hz, 1H), 7.37 (d, J=4.6 Hz, 1H), 7.20 (1, J=7.3 Hz, 1H), 7.05 (t, J=7.3 Hz, 1H), 6.62 (s, 1H), 3.65 (s, 3H), 2.05-1.98 (m, 1H), 0.88-0.81 (m, 4H).

Example 167

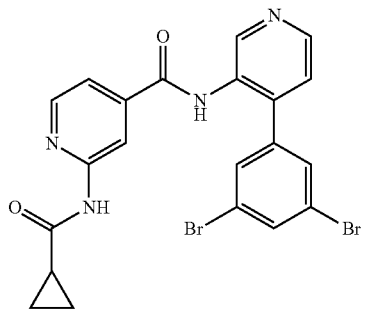 [SMILES: O=C(Nc1cnccc1-c1cc(Br)cc(Br)c1)c1ccnc(NC(=O)C2CC2)c1]

2-(cyclopropanecarboxamido)-N-(4-(3,5-dibromophenyl)pyridin-3-yl)isonicotinamide $^1$H NMR (400 MHz, DMSO-d) δ ppm 10.99 (s, 1H) 10.50 (br. s., 1H) 8.67 (s, 1H) 8.59 (d, J=4.89 Hz, 1H) 8.48 (d, J=5.14 Hz, 1H) 8.44 (s, 1H) 7.87 (t, J=1.71 Hz, 1H) 7.71 (d, J=1.47 Hz, 2H) 7.55 (d, J=5.14 Hz, 1H) 7.38 (d, J=5.14 Hz, 1H) 2.02 (dt, J=12.41, 6.14 Hz, 1H) 0.78-0.87 (m, 4H). MS (ESI) (m/z): 517.0 (M+H)$^+$.

Example 168

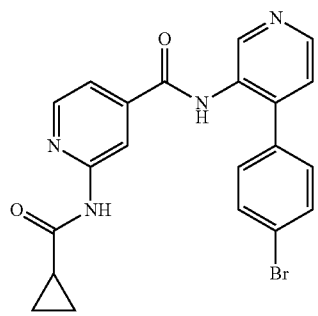 [SMILES: O=C(Nc1cnccc1-c1ccc(Br)cc1)c1ccnc(NC(=O)C2CC2)c1]

N-(4-(4-bromophenyl)pyridin-3-yl)-2-(cyclopropanecarboxamido)isonicotinamide $^1$H NMR (500 MHz, DMSO-d$_6$) δ ppm 11.01 (s, 1H) 10.44 (br. s., 1H) 8.67 (s, 1H) 8.58 (d, J=4.88 Hz, 1H) 8.47 (d, J=4.88 Hz, 1H) 8.45 (s, 1H) 7.67 (d, J=8.55 Hz, 2H) 7.45-7.51 (m, 3H) 7.41 (d, J=4.27 Hz, 1H) 2.00-2.08 (m, 1H) 0.82-0.90 (m, 4H). MS (ESI) (m/z): 439.0 (M+H)$^+$.

Example 169

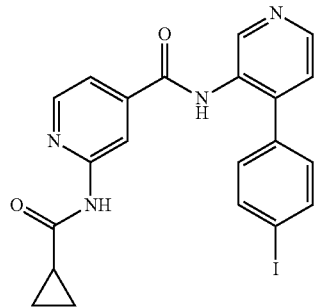 [SMILES: O=C(Nc1cnccc1-c1ccc(I)cc1)c1ccnc(NC(=O)C2CC2)c1]

2-(cyclopropanecarboxamido)-N-(4-(4-iodophenyl)pyridin-3-yl)isonicotinamide

To a microwave vial was added copper(I) iodide (0.218 mg, 1.143 μmol), sodium iodide (6.86 mg, 0.046 mmol), N-(4-(4-bromophenyl)pyridin-3-yl)-2-(cyclopropanecarboxamido)isonicotinamide (0.01 g, 0.023 mmol) and (1S, 2S)—N1,N2-dimethylcyclohexane-1,2-diamine (0.325 mg, 2.287 μmol). The vessel was degassed and flushed with nitrogen (3×). Then dioxane (1 mL) was added and the vessel was degassed, flushed with nitrogen (3×) and then sealed. The reaction mixture was stirred at 110° C. for 24 h.

The mixture was then filtered through a pad of celite, diluted with ethyl acetate and washed with water. The organic layer was dried over sodium sulfate, filtered and then concentrated. The crude material was purified via preparative LC. $^1$H NMR (500 MHz, DMSO-d) δ ppm 11.01 (s, 1H) 10.42 (br. s., 1H) 8.54-8.86 (m, 2H) 8.34-8.54 (m, 2H) 7.83 (d, J=8.24 Hz, 2H) 7.19-7.55 (m, 4H) 1.91-2.14 (m, 1H) 0.75-1.01 (m, 4H). MS (ESI) (m/z): 485.1 (M+H)$^+$.

Example 36

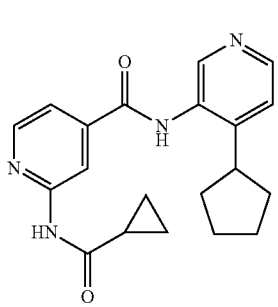 [SMILES: O=C(Nc1cnccc1C1CCCC1)c1ccnc(NC(=O)C2CC2)c1]

N-(4-cyclopentylpyridin-3-yl)-2-(cyclopropanecarboxamido)isonicotinamide

In a 25 mL round-bottom flask under nitrogen was dissolved 2-(cyclopropanecarboxamido)-N-(4-iodopyridin-3-yl)isonicotinamide (77 mg, 0.189 mmol), 1,1'-bis(diphenylphosphino) ferrocenepalladium(II) dichloride, toluene (3.10 mg, 3.77 mol), and CuI (1.257 mg, 6.60 μmol) in tetrahydrofuran (2 mL) to give a tan solution. Cyclopentylzinc(II) bromide (1.132 mL, 0.566 mmol) was added dropwise under nitrogen. The mixture was stirred at rt for 2 h. Another 2 mL of the zinc reagent (5 equiv.), and 1,1'-bis(diphenylphosphino)ferrocenepalladium(II) dichloride, toluene (3.10 mg, 3.77 μmol) were added. The mixture was heated at 60° C. under nitrogen for another 5 h. After cooling to rt, it was treated with 0.5 ml saturated ammonium chloride/anhydrous Na$_2$SO$_4$. The mixture was concentrated in vacuo. The residue was dissolved in 1.5 mL dimethylformamide and purified by prep-HPLC to afford the desired product (8.7 mg, 13%): MS (ESI) (m/z): 351 (M+H)$^+$; $^1$H NMR (500 MHz, DMSO) δ 11.04 (s, 1H), 10.36 (s, 1H), 8.58 (s, 1H), 8.52 (d, J=5.0 Hz, 1H), 8.50-8.32 (m, 2H), 7.59 (d, J=4.2 Hz, 1H), 7.47-7.38 (m, 1H), 3.25-3.14 (m, 1H), 2.09-1.96 (m, 3H), 1.77 (t, J=6.9 Hz, 2H), 1.65-1.53 (m, 4H), 0.89-0.84 (m, 4H).

Example 37

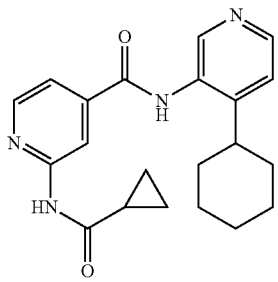 [SMILES: O=C(Nc1cnccc1C1CCCCC1)c1ccnc(NC(=O)C2CC2)c1]

N-(4-cyclohexylpyridin-3-yl)-2-(cyclopropanecarboxamido)isonicotinamide

MS (ESI) (m/z): 365 (M+H)$^+$; $^1$H NMR (500 MHz, DMSO) δ 11.05 (s, 1H), 10.35 (s, 1H), 8.58 (s, 1H), 8.53 (d, J=5.1 Hz, 1H), 8.46-8.39 (m, 2H), 7.57 (d, J=3.9 Hz, 1H), 7.40 (d, J=5.2 Hz, 1H), 2.05 (dd, J=12.3, 5.7 Hz, 1H), 1.75 (dd, J=32.2, 16.2 Hz, 5H), 1.40 (dd, J=22.6, 10.5 Hz, 2H), 1.29 (dd, J=23.5, 11.0 Hz, 4H), 0.89-0.83 (m, 4H).

Example 41

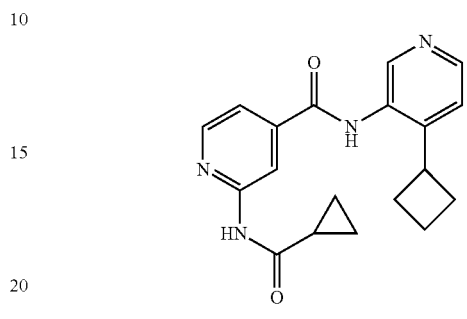

N-(4-cyclobutylpyridin-3-yl)-2-(cyclopropanecarboxamido)isonicotinamide

MS (ESI) (m/z): 337 (M+H)$^+$; $^1$H NMR (500 MHz, DMSO) δ 11.04 (s, 1H), 10.33 (s, 1H), 8.57 (s, 1H), 8.52 (d, J=5.1 Hz, 1H), 8.44 (d, J=5.1 Hz, 1H), 8.41 (s, 1H), 7.56 (d, J=4.4 Hz, 1H), 7.37 (d, J=5.0 Hz, 1H), 3.71 (p, J=9.0 Hz, 1H), 2.26 (q, J=8.4 Hz, 2H), 2.14-2.02 (m, 3H), 2.01-1.89 (m, 1H), 1.77 (q, J=9.2 Hz, 1H), 0.93-0.80 (m, 4H).

Example 110

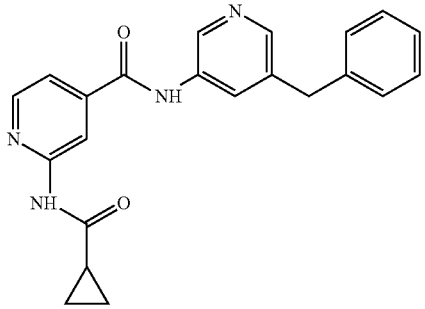 [SMILES: O=C(Nc1cncc(Cc2ccccc2)c1)c1ccnc(NC(=O)C2CC2)c1]

N-(5-benzylpyridin-3-yl)-2-(cyclopropanecarboxamido)isonicotinamide

To a solution of N-(5-bromopyridin-3-yl)-2-(cyclopropanecarboxamido)isonicotinamide and benzylzinc(II) bromide, 0.5 M tetrahydrofuran (1.384 mL, 0.692 mmol) in tetrahydrofuran (3 mL) that had been degassed and flushed with nitrogen (3×) was added PdCl2(dppf)-methylene chloride adduct (0.011 g, 0.014 mmol) and copper (I) iodide (2.64 mg, 0.014 mmol). The reaction mixture was degassed and flushed with nitrogen (3×). The mixture was then heated in an oil bath at 110 C for 20 mins. Water and ethyl acetate were then added and the mixture was filtered through a pad of celite. The organic layer was separated, dried over sodium sulfate and concentrated. The sample was purified using a preparative HPLC to give N-(5-benzylpyridin-3-yl)-2-(cyclopropanecarboxamido)isonicotinamide (1.5 mg, 3.62 µmol, 2.6% yield). MS (ESI) (m/z): 373.2 (M+H)$^+$.

Example 113

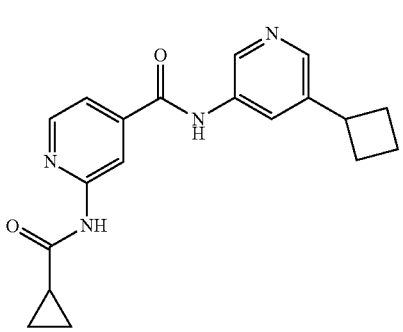 [SMILES: O=C(Nc1cncc(C2CCC2)c1)c1ccnc(NC(=O)C2CC2)c1]

N-(5-cyclobutylpyridin-3-yl)-2-(cyclopropanecarboxamido)isonicotinamide

To a mixture of N-(5-bromopyridin-3-yl)-2-(cyclopropanecarboxamido)isonicotinamide (20 mg, 0.055 mmol) and potassium carbonate (45.9 mg, 0.332 mmol) was added dimethylformamide (1 mL). The reaction was stirred at rt until all solids dissolved and then PdCl2(dppf)-methylene chloride adduct (9.04 mg, 0.011 mmol) was added. The flask was degassed and flushed with nitrogen, and then cyclobutylzinc(II) bromide (1.107 mL, 0.554 mmol) was added dropwise. The flask was degassed and flushed with nitrogen, and then the reaction vessel was sealed and then heated at 90° C. for 10 h. The reaction was diluted with ethyl acetate and saturated ammonium chloride. The organic layer was washed with water, brine and dried over sodium sulfate. The crude material was purified via preparative LC. $^1$H NMR (500 MHz, DMSO-d$_6$) δ ppm 11.06 (s, 1H) 10.69 (br. s., 1H) 8.78 (d, J=2.14 Hz, 1H) 8.55 (s, 1H) 8.52 (d, J=4.88 Hz, 1H) 8.23 (d, J=1.53 Hz, 1H) 8.09 (s, 1H) 7.55-7.60 (m, 1H) 3.60 (quin, J=8.70 Hz, 1H) 2.31-2.40 (m, 2H) 2.00-2.19 (m, 4H) 1.88 (q, J=9.26 Hz, 1H) 0.84-0.90 (m, 4H). MS (ESI) (m/z): 337.2 (M+H)$^+$.

Example 132

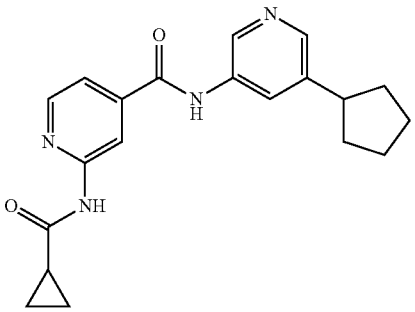 [SMILES: O=C(Nc1cncc(C2CCCC2)c1)c1ccnc(NC(=O)C2CC2)c1]

N-(5-cyclopentylpyridin-3-yl)-2-(cyclopropanecarboxamido)isonicotinamide $^1$H NMR (500 MHz, DMSO-d$_6$) δ ppm 11.05 (s, 1H) 10.64 (s, 1H) 8.78 (d, J=2.44 Hz, 1H) 8.54 (s, 1H) 8.52 (d, J=4.88 Hz, 1H) 8.27 (d, J=2.14 Hz, 1H) 8.02-8.08 (m, 1H) 7.56 (dd, J=5.19, 1.53 Hz, 1H) 3.01-3.11 (m, 1H) 2.02-2.14 (m, 3H) 1.75-1.85 (m, 2H) 1.64-1.74 (m, 2H) 1.49-1.61 (m, 2H) 0.82-0.90 (m, 4H). MS (ESI) (m/z): 351.3 (M+H)$^+$.

Example 43

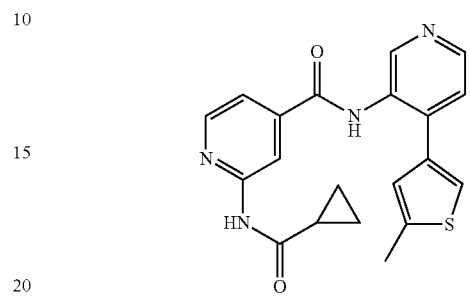

2-(Cyclopropanecarboxamido)-N-(4-(5-methylthiophen-3-yl)pyridin-3-yl)isonicotinamide In a 15 mL vial was dissolved 4-(5-methylthiophen-3-yl)pyridin-3-amine (30 mg, 0.158 mmol) and 2-(cyclopropanecarboxamido)isonicotinic acid (32.5 mg, 0.158 mmol) in dimethylformamide (1 mL) to give a tan solution. HATU (120 mg, 0.315 mmol) and Hunig's base (0.055 mL, 0.315 mmol) were added, and the mixture was stirred at rt over 2 days. The mixture was directly purified by Prep-HPLC to afford the desired product (34.5 mg, 58%): MS (ESI) (m/z): 379 (M+H)$^+$; $^1$H NMR (400 MHz, DMSO) δ 10.95 (s, 1H), 10.17 (s, 1H), 8.70 (s, 1H), 8.52 (d, J=5.0 Hz, 1H), 8.44 (d, J=5.1 Hz, 1H), 8.41 (s, 1H), 7.48 (d, J=3.2 Hz, 1H), 7.38 (d, J=4.9 Hz, 1H), 7.34 (d, J=4.3 Hz, 1H), 7.26 (dd, J=3.2, 1.1 Hz, 1H), 2.10 (d, J=0.6 Hz, 3H), 2.08-2.00 (m, 1H), 0.92-0.82 (m, 4H).

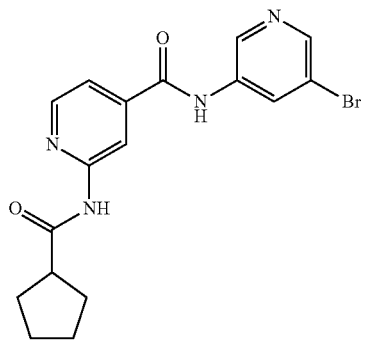 [SMILES: O=C(Nc1cncc(Br)c1)c1ccnc(NC(=O)C2CCCC2)c1]

N-(5-bromopyridin-3-yl)-2-(cyclopentanecarboxamido)isonicotinamide $^1$H NMR (500 MHz, Chloroform-d) δ ppm 8.67 (d, J=2.14 Hz, 1H) 8.58 (s, 1H) 8.54-8.57 (m, 1H) 8.47-8.53 (m, 2H) 8.27 (d, J=9.46 Hz, 2H) 7.60 (dd, J=5.19, 1.53 Hz, 1H) 1.61-1.64 (m, 1H) 1.11-1.20 (m, 2H) 0.95-1.04 (m, 2H). MS (ESI) (m/z): 389,391 (M+H)⁺.

Example 6

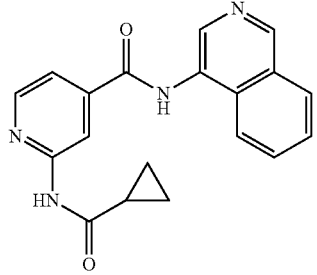 [SMILES: O=C(Nc1cncc2ccccc12)c1ccnc(NC(=O)C2CC2)c1]

2-(Cyclopropanecarboxamido)-N-(isoquinolin-4-yl) isonicotinamide

MS (ESI) (m/z): 333 (M+H)⁺; ¹H NMR (500 MHz, DMSO) δ 11.06 (s, 1H), 10.81 (s, 1H), 9.28 (s, 1H), 8.67 (s, 1H), 8.62 (s, 1H), 8.56 (d, J=5.1 Hz, 1H), 8.22 (d, J=8.1 Hz, 1H), 7.99 (d, J=7.9 Hz, 1H), 7.87-7.82 (m, 1H), 7.76 (ddd, J=8.0, 7.0, 1.0 Hz, 1H), 7.71 (d, J=4.6 Hz, 1H), 2.14-2.01 (m, 1H), 0.91-0.82 (m, 4H).

Example 44

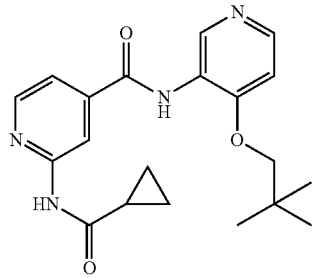 [SMILES: CC(C)(C)COc1ccncc1NC(=O)c1ccnc(NC(=O)C2CC2)c1]

2-(Cyclopropanecarboxamido)-N-(4-(neopentyloxy) pyridin-3-yl)isonicotinamide

MS (ESI) (m/z): 369 (M+H)⁺; ¹H NMR (400 MHz, DMSO) δ 10.98 (s, 1H), 9.97 (s, 1H), 8.56 (s, 1H), 8.51 (dd, J=5.1, 0.6 Hz, 1H), 8.49 (s, 1H), 8.36 (d, J=5.6 Hz, 1H), 7.53 (dd, J=5.1, 1.4 Hz, 1H), 7.16 (d, J=5.7 Hz, 1H), 3.77 (s, 2H), 2.12-1.99 (m, 1H), 0.96 (s, 9H), 0.90-0.83 (m, 4H).

Example 45

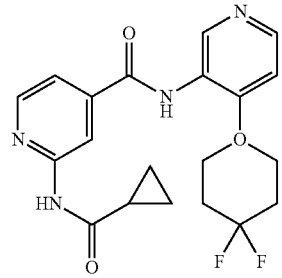

2-(Cyclopropanecarboxamido)-N-(4-(4,4-difluoropiperidin-1-yl)pyridin-3-yl)isonicotinamide MS (ESI) (m/z): 402 (M+H)⁺; ¹H NMR (500 MHz, DMSO) δ 11.07 (s, 1H), 10.05 (s, 1H), 8.58 (d, J=10.6 Hz, 2H), 8.53 (d, J=5.1 Hz, 1H), 8.29 (d, J=5.5 Hz, 1H), 7.57 (d, J=4.7 Hz, 1H), 7.12 (d, J=5.5 Hz, 1H), 3.26-3.16 (m, 4H), 2.18-2.00 (m, 5H), 0.91-0.81 (m, 4H).

Example 46

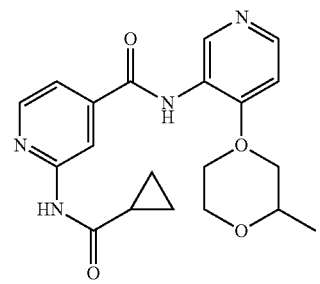

2-(Cyclopropanecarboxamido)-N-(4-(2-methylmorpholino)pyridin-3-yl)isonicotinamide MS (ESI) (m/z): 382 (M+H)⁺; ¹H NMR (500 MHz, DMSO) δ 11.05 (s, 1H), 10.15 (s, 1H), 8.56 (s, 1H), 8.52 (d, J=5.1 Hz, 1H), 8.42 (s, 1H), 8.28 (d, J=5.6 Hz, 1H), 7.54 (d, J=4.4 Hz, 1H), 7.04 (d, J=5.6 Hz, 1H), 3.84 (d, J=10.1 Hz, 1H), 3.71-3.56 (m, 2H), 3.46-3.38 (m, 2H), 2.90-2.81 (m, 1H), 2.60-2.54 (m, 1H), 2.12-2.00 (m, 1H), 1.06 (d, J=6.2 Hz, 3H), 0.86 (d, J=6.0 Hz, 4H).

Example 50

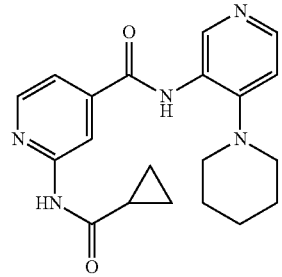 [SMILES: O=C(Nc1cnccc1N1CCCCC1)c1ccnc(NC(=O)C2CC2)c1]

2-(Cyclopropanecarboxamido)-N-(4-(piperidin-1-yl) pyridin-3-yl)isonicotinamide

MS (ESI) (m/z): 366 (M+H)⁺; ¹H NMR (500 MHz, DMSO) δ 11.03 (s, 1H), 10.00 (s, 1H), 8.58 (s, 1H), 8.52 (d,

J=5.1 Hz, 1H), 8.42 (s, 1H), 8.25 (d, J=5.5 Hz, 1H), 7.58 (d, J=4.5 Hz, 1H), 7.01 (d, J=5.6 Hz, 1H), 3.12-3.00 (m, 4H), 2.12-2.00 (m, 1H), 1.60 (s, 4H), 1.54 (d, J=4.6 Hz, 2H), 0.91-0.80 (m, 4H).

Example 52

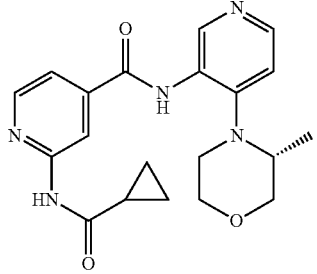 [SMILES: C[C@@H]1COCCN1c1ccncc1NC(=O)c1ccnc(NC(=O)C2CC2)c1]

(R)-2-(cyclopropanecarboxamido)-N-(4-(3-methyl-morpholino)pyridin-3-yl)isonicotinamide MS (ESI) (m/z): 382 (M+H)+; 1H NMR (500 MHz, DMSO) δ 11.07 (s, 1H), 10.00 (s, 1H), 8.78 (s, 1H), 8.60 (s, 1H), 8.53 (d, J=5.1 Hz, 1H), 8.33 (d, J=5.4 Hz, 1H), 7.55 (d, J=4.5 Hz, 1H), 7.20 (d, J=5.4 Hz, 1H), 3.83-3.74 (m, 2H), 3.72-3.65 (m, 1H), 3.57-3.49 (m, 1H), 3.46 (dd, J=11.0, 5.6 Hz, 1H), 3.15 (ddd, J=12.1, 6.6, 2.9 Hz, 1H), 2.90-2.84 (m, 1H), 2.12-2.01 (m, 1H), 0.94-0.84 (m, 7H).

Example 53

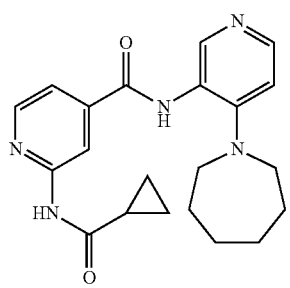 [SMILES: O=C(Nc1cnccc1N1CCCCCC1)c1ccnc(NC(=O)C2CC2)c1]

N-(4-(azepan-1-yl)pyridin-3-yl)-2-(cyclopropanecar-boxamido)isonicotinamide

MS (ESI) (m/z): 380 (M+H)+; 1H NMR (500 MHz, DMSO) δ 11.02 (s, 1H), 10.22 (s, 1H), 8.57 (s, 1H), 8.50 (dd, J=5.2, 0.5 Hz, 1H), 8.08 (d, J=6.0 Hz, 1H), 7.97 (s, 1H), 7.57 (dd, J=5.1, 1.5 Hz, 1H), 6.81 (d, J=6.0 Hz, 1H), 3.48-3.43 (m, 4H), 2.10-1.99 (m, 1H), 1.68 (s, 4H), 1.48 (s, 4H), 0.91-0.81 (m, 4H).

Example 54

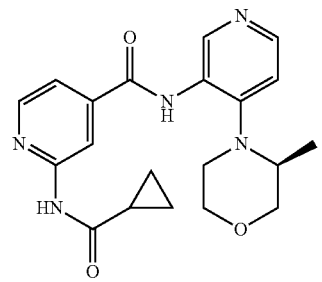 [SMILES: C[C@H]1COCCN1c1ccncc1NC(=O)c1ccnc(NC(=O)C2CC2)c1]

(S)-2-(cyclopropanecarboxamido)-N-(4-(3-methyl-morpholino)pyridin-3-yl)isonicotinamide MS (ESI) (m/z): 382 (M+H)+; 1H NMR (500 MHz, DMSO) δ 11.07 (s, 1H), 10.00 (s, 1H), 8.78 (s, 1H), 8.60 (s, 1H), 8.53 (d, J=5.0 Hz, 1H), 8.32 (d, J=5.4 Hz, 1H), 7.55 (d, J=4.4 Hz, 1H), 7.20 (d, J=5.4 Hz, 1H), 3.83-3.73 (m, 2H), 3.72-3.62 (m, 1H), 3.58-3.51 (m, 1H), 3.46 (dd, J=11.0, 5.6 Hz, 1H), 3.15 (ddd, J=12.2, 6.6, 2.9 Hz, 1H), 2.90-2.82 (m, 1H), 2.11-2.00 (m, 1H), 0.93-0.81 (m, 7H).

Example 57

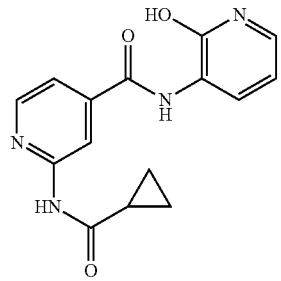 [SMILES: O=C(Nc1cccnc1O)c1ccnc(NC(=O)C2CC2)c1]

2-(Cyclopropanecarboxamido)-N-(2-hydroxypyri-din-3-yl)isonicotinamide

MS (ESI) (m/z): 299 (M+H)+; 1H NMR (500 MHz, DMSO) δ 12.18 (s, 1H), 11.08 (s, 1H), 9.44 (s, 1H), 8.61-8.44 (m, 2H), 8.30 (dd, J=7.3, 1.8 Hz, 1H), 7.51 (dd, J=5.1, 1.6 Hz, 1H), 7.23 (dd, J=6.6, 1.8 Hz, 1H), 6.42-6.22 (m, 1H), 2.05 (dq, J=7.5, 5.0 Hz, 1H), 0.93-0.81 (m, 4H).

Example 58

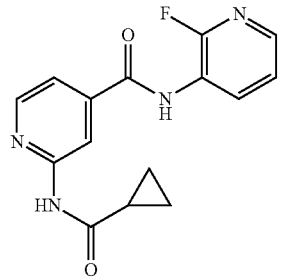 [SMILES: O=C(Nc1cccnc1F)c1ccnc(NC(=O)C2CC2)c1]

2-(Cyclopropanecarboxamido)-N-(2-fluoropyridin-3-yl)isonicotinamide

MS (ESI) (m/z): 301 (M+H)+; 1H NMR (500 MHz, DMSO) δ 11.06 (s, 1H), 10.61 (s, 1H), 8.57 (d, J=0.5 Hz,

1H), 8.53 (dd, J=5.1, 0.6 Hz, 1H), 8.20 (ddd, J=9.6, 7.8, 1.7 Hz, 1H), 8.15-8.09 (m, 1H), 7.56 (dd, J=5.1, 1.6 Hz, 1H), 7.48-7.40 (m, 1H), 2.11-2.00 (m, 1H), 0.92-0.81 (m, 4H).

Example 60

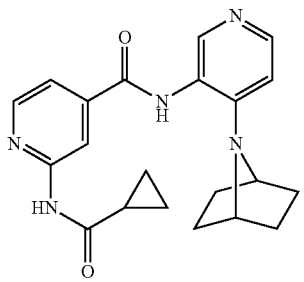 [SMILES: O=C(Nc1cnccc1N1C2CCC1CC2)c1ccnc(NC(=O)C2CC2)c1]

N-(4-(1s,4s)-7-azabicyclo[2.2.1]heptan-7-yl)pyridin-3-yl)-2-(cyclopropanecarboxamido)isonicotinamide MS (ESI) (m/z): 378 (M+H)+; 1H NMR (500 MHz, DMSO) δ 11.03 (s, 1H), 10.21 (s, 1H), 8.59 (s, 1H), 8.52 (d, J=5.1 Hz, 1H), 8.15 (s, 1H), 8.13 (d, J=5.7 Hz, 1H), 7.60 (dd, J=5.1, 1.4 Hz, 1H), 6.98 (d, J=5.7 Hz, 1H), 4.38 (s, 2H), 2.05 (t, J=5.5 Hz, 1H), 1.66 (d, J=6.8 Hz, 4H), 1.41 (d, J=6.9 Hz, 4H), 0.91-0.81 (m, 4H).

Example 61

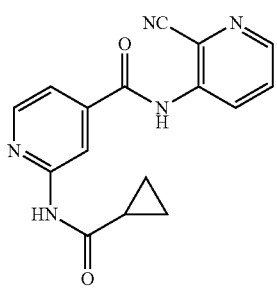 [SMILES: N#Cc1ncccc1NC(=O)c1ccnc(NC(=O)C2CC2)c1]

2-(Cyclopropanecarboxamido)-N-(2-cyanopyridin-3-yl)isonicotinamide

MS (ESI) (m/z): 308 (M+H)+; 1H NMR (500 MHz, DMSO) δ 11.01 (s, 1H), 8.62 (s, 1H), 8.51 (d, J=4.9 Hz, 2H), 8.21 (dd, J=8.4, 1.3 Hz, 1H), 7.73 (dd, J=8.4, 4.6 Hz, 1H), 7.64 (dd, J=5.1, 1.5 Hz, 1H), 2.09-1.99 (m, 1H), 0.91-0.81 (m, 4H).

Example 62

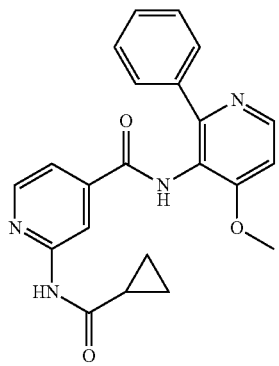 [SMILES: COc1ccnc(-c2ccccc2)c1NC(=O)c1ccnc(NC(=O)C2CC2)c1]

2-(Cyclopropanecarboxamido)-N-(4-methoxy-2-phenylpyridin-3-yl)isonicotinamide

MS (ESI) (m/z): 389 (M+H)+; 1H NMR (500 MHz, DMSO) δ 10.96 (s, 1H), 10.07 (s, 1H), 8.53 (d, J=5.4 Hz, 1H), 8.44 (s, 2H), 7.63 (d, J=7.2 Hz, 2H), 7.45-7.30 (m, 4H), 7.20 (d, J=5.6 Hz, 1H), 3.89 (s, 3H), 2.08-2.00 (m, 1H), 0.90-0.81 (m, 4H).

Example 63

2-(Cyclopropanecarboxamido)-N-(3-phenylisoquinolin-4-yl)isonicotinamide

MS (ESI) (m/z): 409 (M+H)+.

Examples 77 and 78 were resolved from racemic material (example 46) by chiral HPLC, and the absolute configurations were not determined.

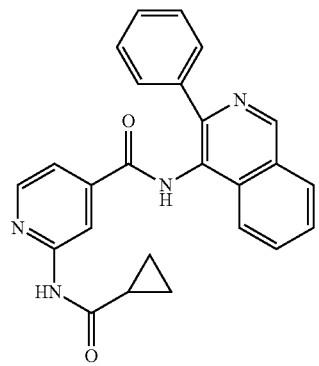 [SMILES: O=C(Nc1c(-c2ccccc2)ncc2ccccc12)c1ccnc(NC(=O)C2CC2)c1]

Example 77

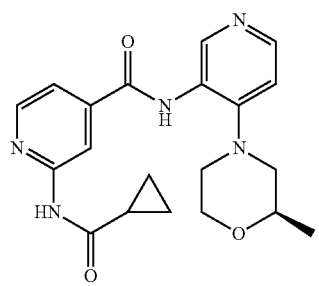 [SMILES: C[C@@H]1CN(c2ccncc2NC(=O)c2ccnc(NC(=O)C3CC3)c2)CCO1]

(R)-2-(Cyclopropanecarboxamido)-N-(4-(2-methylmorpholino)pyridine-3-yl)isonicotinamide MS (ESI) (m/z): 382 (M+H)+.

Example 78

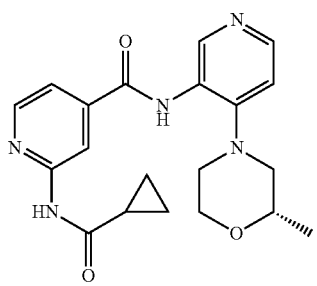 [SMILES: C[C@H]1CN(c2ccncc2NC(=O)c2ccnc(NC(=O)C3CC3)c2)CCO1]

(S)-2-(Cyclopropanecarboxamido)-N-(4-(2-methyl-morpholino)pyridin-3-yl)isonicotinamide MS (ESI) (m/z): 382 (M+H)⁺.

Example 79

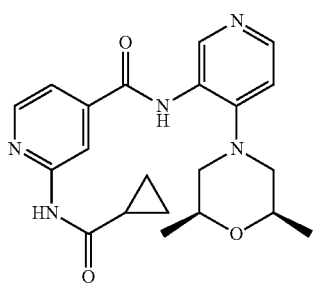 [SMILES: C[C@@H]1CN(c2ccncc2NC(=O)c2ccnc(NC(=O)C3CC3)c2)C[C@H](C)O1]

2-(Cyclopropanecarboxamido)-N-(4-((2S,6R)-2,6-dimethylmorpholino)pyridin-3-yl)isonicotinamide MS (ESI) (m/z): 396 (M+H)⁺; $^1$H NMR (500 MHz, DMSO) δ 11.04 (s, 1H), 10.14 (s, 1H), 8.56 (s, 1H), 8.51 (d, J=5.0 Hz, 1H), 8.39 (s, 1H), 8.26 (d, J=5.6 Hz, 1H), 7.52 (d, J=4.4 Hz, 1H), 7.01 (d, J=5.6 Hz, 1H), 3.76-3.63 (m, 2H), 3.41-3.37 (m, 2H), 2.50-2.40 (m, 2H), 2.05 (dd, J=12.4, 6.2 Hz, 1H), 1.06 (s, 3H), 1.05 (s, 3H), 0.86 (d, J=6.2 Hz, 4H).

Example 80

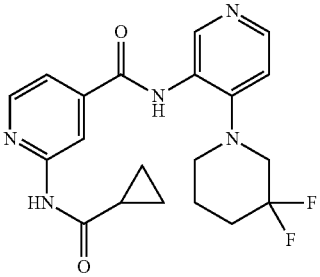 [SMILES: O=C(Nc1cnccc1N1CCCC(F)(F)C1)c1ccnc(NC(=O)C2CC2)c1]

2-(Cyclopropanecarboxamido)-N-(4-(3,3-difluoropi-peridin-1-yl)pyridin-3-yl)isonicotinamide MS (ESI) (m/z): 402 (M+H)⁺; $^1$H NMR (500 MHz, DMSO) δ 11.02 (s, 1H), 10.09 (s, 1H), 8.57 (s, 1H), 8.52 (d, J=5.0 Hz, 1H), 8.38 (s, 1H), 8.29 (d, J=5.5 Hz, 1H), 7.58 (d, J=5.0 Hz, 1H), 7.08 (d, J=5.6 Hz, 1H), 3.42 (t, J=11.7 Hz, 2H), 3.19 (s, 2H), 2.12-1.97 (m, 3H), 1.77 (s, 2H), 0.91-0.79 (m, 4H).

Example 83

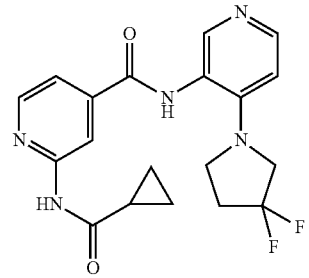 [SMILES: O=C(Nc1cnccc1N1CCC(F)(F)C1)c1ccnc(NC(=O)C2CC2)c1]

2-(Cyclopropanecarboxamido)-N-(4-(3,3-difluoro-pyrrolidin-1-yl)pyridin-3-yl)isonicotinamide MS (ESI) (m/z): 388 (M+H)⁺; $^1$H NMR (500 MHz, DMSO) δ 11.03 (s, 1H), 10.30 (s, 1H), 8.58 (s, 1H), 8.52 (d, J=5.1 Hz, 1H), 8.15 (d, J=5.8 Hz, 1H), 8.04 (s, 1H), 7.58 (dd, J=5.1, 1.5 Hz, 1H), 6.71 (d, J=5.9 Hz, 1H), 3.82 (t, J=13.2 Hz, 2H), 3.65 (t, J=7.3 Hz, 2H), 2.46 (dt, J=21.5, 7.3 Hz, 2H), 2.05 (t, J=6.1 Hz, 1H), 0.92-0.80 (m, 4H).

Example 87

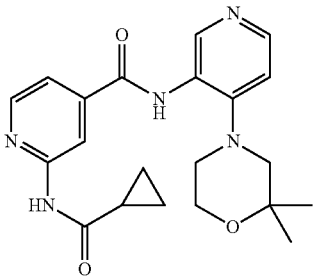 [SMILES: CC1(C)CN(c2ccncc2NC(=O)c2ccnc(NC(=O)C3CC3)c2)CCO1]

2-(Cyclopropanecarboxamido)-N-(4-(2,2-dimethyl-morpholino)pyridin-3-yl)isonicotinamide MS (ESI) (m/z): 396 (M+H)⁺; $^1$H NMR (500 MHz, DMSO) δ 11.03 (s, 1H), 10.10 (s, 1H), 8.58 (s, 1H), 8.51 (d, J=5.1 Hz, 1H), 8.31 (s, 1H), 8.29 (d, J=5.5 Hz, 1H), 7.58 (d, J=4.8 Hz, 1H), 7.01 (d, J=5.6 Hz, 1H), 3.73-3.64 (m, 2H), 3.07-3.02 (m, 2H), 2.91 (s, 2H), 2.10-2.00 (m, 1H), 1.13 (s, 6H), 0.86 (d, J=5.3 Hz, 4H).

Example 88

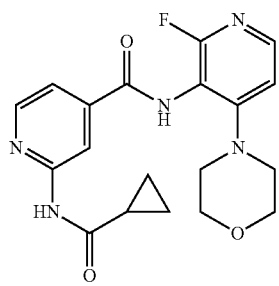 [SMILES: O=C(Nc1c(N2CCOCC2)ccnc1F)c1ccnc(NC(=O)C2CC2)c1]

2-(Cyclopropanecarboxamido)-N-(2-fluoro-4-morpholinopyridin-3-yl)isonicotinamide MS (ESI) (m/z): 386 (M+H)+; 1H NMR (500 MHz, DMSO) δ 11.04 (s, 1H), 10.20 (s, 1H), 8.55 (s, 1H), 8.51 (d, J=5.0 Hz, 1H), 7.95 (d, J=5.7 Hz, 1H), 7.53 (d, J=4.7 Hz, 1H), 6.96 (d, J=5.8 Hz, 1H), 3.72-3.62 (m, 4H), 3.29-3.19 (m, 4H), 2.11-2.00 (m, 1H), 0.91-0.80 (m, 4H).

Example 90

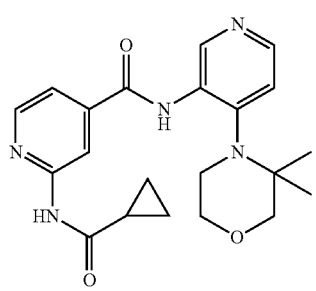 [SMILES: CC1(C)COCCN1c1ccncc1NC(=O)c1ccnc(NC(=O)C2CC2)c1]

2-(Cyclopropanecarboxamido)-N-(4-(3,3-dimethylmorpholino)pyridin-3-yl)isonicotinamide MS (ESI) (m/z): 396 (M+H)+; 1H NMR (500 MHz, DMSO) δ 11.13 (s, 1H), 9.97 (s, 1H), 9.26 (s, 1H), 8.68 (s, 1H), 8.58 (d, J=5.1 Hz, 1H), 8.38 (d, J=5.3 Hz, 1H), 7.59 (d, J=5.0 Hz, 1H), 7.43 (d, J=5.3 Hz, 1H), 3.77 (t, J=4.6 Hz, 2H), 3.49 (s, 2H), 3.01 (br, 2H), 2.13-2.02 (m, 1H), 1.02 (s, 6H), 0.88 (d, J=5.6 Hz, 4H).

Example 170

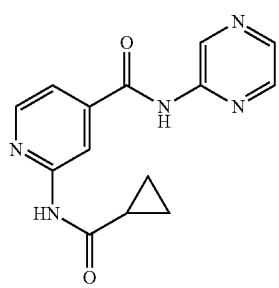 [SMILES: O=C(Nc1cnccn1)c1ccnc(NC(=O)C2CC2)c1]

2-(Cyclopropanecarboxamido)-N-(pyrazin-2-yl)isonicotinamide

MS (ESI) (m/z): 284 (M+H)+.

Example 178

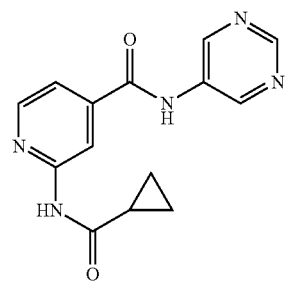 [SMILES: O=C(Nc1cncnc1)c1ccnc(NC(=O)C2CC2)c1]

2-(Cyclopropanecarboxamido)-N-(pyrimidin-5-yl)isonicotinamide

MS (ESI) (m/z): 284 (M+H)+; 1H NMR (500 MHz, DMSO) δ 11.08 (s, 1H), 10.91 (s, 1H), 9.17 (s, 2H), 8.98 (s, 1H), 8.58 (s, 1H), 8.55 (d, J=5.1 Hz, 1H), 7.59 (dd, J=5.1, 1.3 Hz, 1H), 2.12-2.00 (m, 1H), 0.95-0.81 (m, 4H).

Example 179

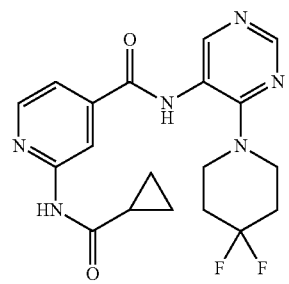 [SMILES: O=C(Nc1cncnc1N1CCC(F)(F)CC1)c1ccnc(NC(=O)C2CC2)c1]

2-(Cyclopropanecarboxamido)-N-(4-(4,4-difluoropiperidin-1-yl)pyrimidin-5-yl)isonicotinamide MS (ESI) (m/z): 403 (M+H)+; 1H NMR (500 MHz, DMSO) δ 10.99 (s, 1H), 10.79-10.15 (m, 1H), 8.58 (s, 1H), 8.55-8.46 (m, 2H), 8.38 (s, 1H), 7.58 (d, J=4.7 Hz, 1H), 3.85-3.69 (m, 4H), 2.13-1.92 (m, 5H), 0.93-0.77 (m, 4H).

Example 187

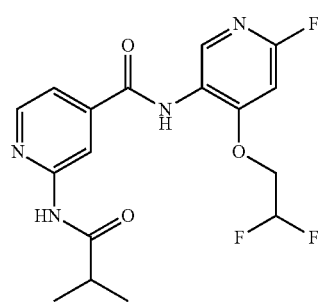 [SMILES: CC(C)C(=O)Nc1cc(C(=O)Nc2cnc(F)cc2OCC(F)F)ccn1]

N-(4-(2,2-difluoroethoxy)-6-fluoropyridin-3-yl)-2-isobutyramidoisonicotinamide

MS (ESI) (m/z): 383 (M+H)+; 1H NMR (500 MHz, DMSO-d6) δ 10.64 (br. s., 1H), 10.14 (br. s., 1H), 8.56 (br.

s., 1H), 8.50 (d, J=4.6 Hz, 1H), 8.22 (s, 1H), 7.52 (br. s., 1H), 7.12 (s, 1H), 6.51-6.25 (m, 1H), 4.55 (t, J=14.2 Hz, 2H), 2.83-2.73 (m, 1H), 1.11 (d, J=6.1 Hz, 6H).

Example 188

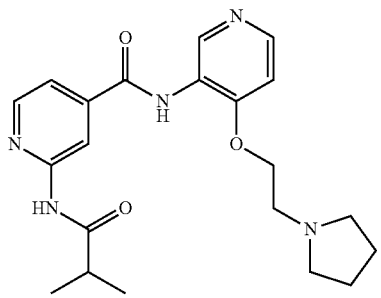 [SMILES: CC(C)C(=O)Nc1cc(C(=O)Nc2cnccc2OCCN2CCCC2)ccn1]

2-Isobutyramido-N-(4-(2-(pyrrolidin-1-yl)ethoxy)pyridin-3-yl)isonicotinamide

MS (ESI) (m/z): 398 (M+H)+; 1H NMR (500 MHz, DMSO-d6) δ 10.64 (s, 1H), 10.16 (s, 1H), 8.66 (s, 1H), 8.57 (s, 1H), 8.49 (d, J=5.2 Hz, 1H), 8.35 (d, J=5.8 Hz, 1H), 7.53 (s, 1H), 7.20 (d, J=5.8 Hz, 1H), 4.25 (s, 2H), 2.94 (s, 2H), 2.82-2.74 (m, 1H), 2.63 (s, 4H), 1.64 (s, 4H), 1.11 (d, J=6.9 Hz, 6H).

Example 189

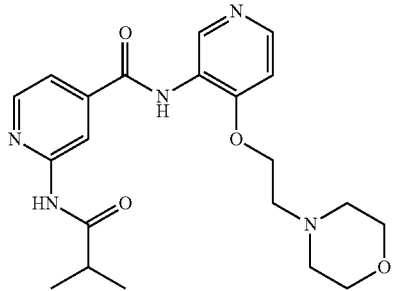 [SMILES: CC(C)C(=O)Nc1cc(C(=O)Nc2cnccc2OCCN2CCOCC2)ccn1]

2-Isobutyramido-N-(4-(2-morpholinoethoxy)pyridin-3-yl)isonicotinamide

MS (ESI) (m/z): 414 (M+H)+; 1H NMR (500 MHz, DMSO-d6) δ 10.64 (s, 1H), 10.04 (s, 1H), 8.60 (s, 1H), 8.56 (s, 1H), 8.49 (d, J=5.3 Hz, 1H), 8.35 (d, J=5.8 Hz, 1H), 7.52 (d, J=5.5 Hz, 1H), 7.19 (d, J=5.8 Hz, 1H), 4.23 (t, J=5.5 Hz, 2H), 2.83-2.73 (m, 1H), 2.72 (t, J=5.5 Hz, 2H), 2.51 (s, 4H), 2.47-2.35 (m, 4H), 1.11 (d, J=6.9 Hz, 6H).

Example 190

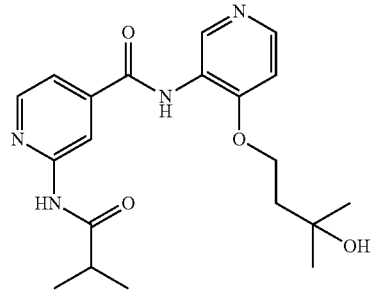 [SMILES: CC(C)C(=O)Nc1cc(C(=O)Nc2cnccc2OCCC(C)(C)O)ccn1]

N-(4-(3-hydroxy-3-methylbutoxy)pyridin-3-yl)-2-isobutyramidoisonicotinamide

MS (ESI) (m/z): 387 (M+H)+; 1H NMR (500 MHz, DMSO-d6) δ 10.64 (s, 1H), 9.92 (s, 1H), 8.61 (s, 1H), 8.56 (s, 1H), 8.49 (d, J=5.2 Hz, 1H), 8.35 (d, J=5.8 Hz, 1H), 7.52 (s, 1H), 7.19 (d, J=5.7 Hz, 1H), 4.23 (t, J=7.1 Hz, 2H), 2.78 (q, J=7.2 Hz, 1H), 1.87 (d, J=7.0 Hz, 2H), 1.14 (s, 6H), 1.11 (d, J=7.6 Hz, 6H).

Example 191

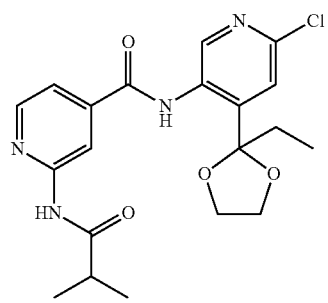 [SMILES: CCC1(c2cc(Cl)ncc2NC(=O)c2ccnc(NC(=O)C(C)C)c2)OCCO1]

N-(6-chloro-4-(2-ethyl-1,3-dioxolan-2-yl)pyridin-3-yl)-2-isobutyramidoisonicotinamide MS (ESI) (m/z): 419 (M+H)+; 1H NMR (500 MHz, DMSO-d6) δ 10.70 (s, 1H), 10.15 (s, 1H), 8.98 (s, 1H), 8.63 (s, 1H), 8.55 (d, J=5.2 Hz, 1H), 7.50 (d, J=5.2 Hz, 1H), 7.47 (s, 1H), 4.14-4.05 (m, 2H), 3.92-3.84 (m, 2H), 2.80 (dt, J=13.4, 6.6 Hz, 1H), 1.89 (q, J=7.1 Hz, 2H), 1.12 (d, J=6.7 Hz, 6H), 0.82 (t, J=7.3 Hz, 3H).

Example 202

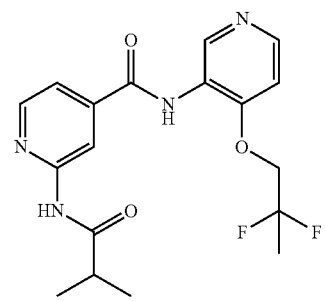 [SMILES: CC(C)C(=O)Nc1cc(C(=O)Nc2cnccc2OCC(C)(F)F)ccn1]

N-(4-(2,2-Difluoropropoxy)pyridin-3-yl)-2-isobutyramidoisonicotinamide

1H NMR (500 MHz, DMSO-d6) δ ppm 10.65 (s, 1H) 10.18 (s, 1H) 8.57 (s, 1H) 8.54 (s, 1H) 8.50 (s, 1H) 8.40 (s, 1H) 7.53 (s, 1H) 7.27 (s, 1H) 4.45 (t, 2H) 2.79 (m, J=6.5 Hz, 1H) 1.72 (t, 3H) 1.11 (d, J=6.5 Hz); MS (ESI) (m/z): 379.2 (M+H)⁺.

Example 203

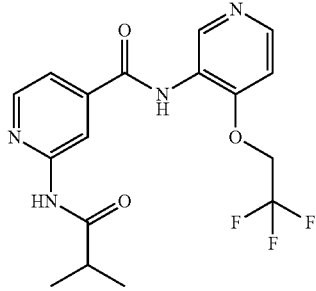

2-Isobutyramido-N-(4-(2,2,2-trifluoroethoxy)pyridin-3-yl)isonicotinamide $^1$H NMR (500 MHz, DMSO-d$_6$) δ ppm 10.64 (s, 1H) 10.21 (s, 1H) 8.56 (s, 1H) 8.53 (s, 1H) 8.50 (d, J=4.5 Hz, 1H) 8.44 (d, J=5 Hz, 1N) 7.51 (d, J=5 Hz, 1H) 7.31 (d, J=5 Hz, 1H) 4.94 (m, 2H) 2.78 (m, J=6.5 Hz, 1H) 1.10 (d, J=6.5 Hz); MS (ESI) (m/z): 383.3 (M+H)⁺.

Example 204

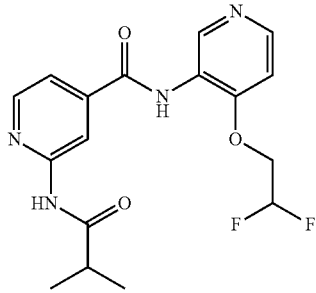 [SMILES: CC(C)C(=O)Nc1cc(C(=O)Nc2cnccc2OCC(F)F)ccn1]

N-(4-(2,2-Difluoroethoxy)pyridin-3-yl)-2-isobutyramidoisonicotinamide $^1$H NMR (500 MHz, DMSO-d$_6$) δ ppm 10.62 (s, 1H) 10.13 (s, 1H) 8.58 (s, 1H) 8.54 (s, 1H) 8.48 (d, J=5.0 Hz, 1H) 8.38 (d, J=5.5 Hz, 1H) 7.52 (d, J=4 Hz, 1H) 7.26 (d, J=5.5 Hz, 1H) 6.36 (t, J=51.5 Hz, 1H), 4.48 (dt, J=3.5 Hz, J=14.2 Hz, 2H) 2.77 (m, J=6.5 Hz, 1H) 1.10 (d, J=6.5 Hz); MS (ESI) (m/z): 365.2 (M+H)⁺.

Example 210

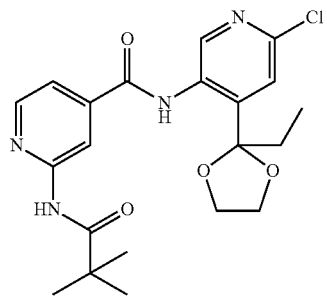 [SMILES: CCC1(c2cc(Cl)ncc2NC(=O)c2ccnc(NC(=O)C(C)(C)C)c2)OCCO1]

N-(6-chloro-4-(2-ethyl-1,3-dioxolan-2-yl)pyridin-3-yl)-2-pivalamidoisonicotinamide MS (ESI) (m/z): 433 (M+H)⁺; $^1$H NMR (500 MHz, DMSO-d$_6$) δ 10.16 (br. s., 1H), 10.11 (s, 1H), 8.99 (s, 1H), 8.61-8.55 (m, 2H), 7.53 (d, J=5.2 Hz, 1H), 7.48 (s, 1H), 4.13-4.06 (m, 2H), 3.92-3.84 (m, 2H), 1.90 (q, J=7.1 Hz, 2H), 1.28 (s, 9H), 0.83 (t, J=7.3 Hz, 3H).

Example 238

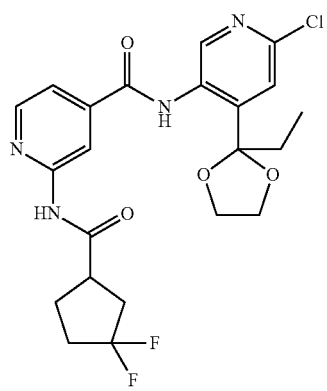 [SMILES: CCC1(c2cc(Cl)ncc2NC(=O)c2ccnc(NC(=O)C3CCC(F)(F)C3)c2)OCCO1]

N-(6-chloro-4-(2-ethyl-1,3-dioxolan-2-yl)pyridin-3-yl)-2-(3,3-difluorocyclopentanecarboxamido)isonicotinamide MS (ESI) (m/z): 481 (M+H)⁺; $^1$H NMR (500 MHz, DMSO-d$_6$) δ 10.92-10.85 (m, 1H), 10.15 (br. s., 1H), 8.98 (s, 1H), 8.63 (s, 1H), 8.57 (d, J=4.9 Hz, 1H), 7.53 (d, J=4.3 Hz, 1H), 7.47 (s, 1H), 4.14-4.03 (m, 2H), 3.93-3.83 (m, 2H), 2.39 (dd, J=17.1, 8.9 Hz, 2H), 2.29-2.03 (m, 3H), 2.00-1.83 (m, 3H), 0.82 (t, J=7.3 Hz, 3H).

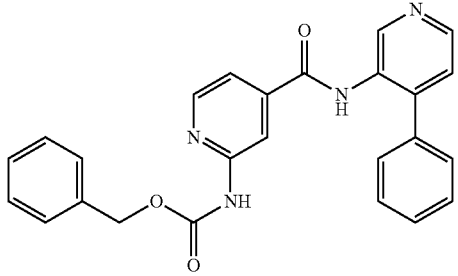 [SMILES: O=C(Nc1cc(C(=O)Nc2cnccc2-c2ccccc2)ccn1)OCc1ccccc1]

Benzyl (4-((4-phenylpyridin-3-yl)carbamoyl)pyridin-2-yl)carbamate

A 100 mL round-bottom flask was charged with 2-chloro-N-(4-phenylpyridin-3-yl)isonicotinamide (200 mg, 0.646 mmol), benzyl carbamate (137 mg, 0.904 mmol), and Cs$_2$CO$_3$ (337 mg, 1.033 mmol) in dioxane (6 mL) to give a tan suspension under nitrogen. Pd(OAc)$_2$ (7.25 mg, 0.032 mmol) and XANTPHOS (28.0 mg, 0.048 mmol) were added, and the mixture was heated at 110° C. under nitrogen overnight for 22 h. The mixture was partitioned between ethyl acetate and water. The layers were separated. The organic layer was washed with brine, dried, and concentrated. The residue was purified by flash chromatography on silica gel, eluting with 0-8% methanol/methylene chloride to afford the product (110 mg, 20%, 50% purity). A small amount was further purified by prep-HPLC to obtain the $^1$H NMR: MS (ESI) (m/z): 425 (M+H)$^+$; $^1$H NMR (500 MHz, MeOD) δ 11.29 (s, 2H), 9.44 (s, 1H), 9.34 (d, J=5.0 Hz, 1H), 9.19 (d, J=5.1 Hz, 1H), 9.02 (s, 1H), 8.37-8.31 (m, 2H), 8.29-8.21 (m, 5H), 8.21-8.12 (m, 5H), 6.01 (s, 2H).

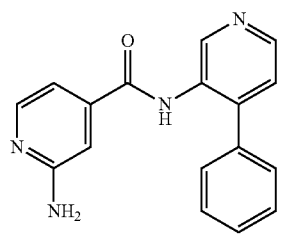 [SMILES: Nc1cc(C(=O)Nc2cnccc2-c2ccccc2)ccn1]

2-Amino-N-(4-phenylpyridin-3-yl)isonicotinamide

A 250 mL round-bottom flask was charged with benzyl (4-((4-phenylpyridin-3-yl)carbamoyl)pyridin-2-yl)carbamate (100 mg, 0.236 mmol) in methanol (4 mL) to give a tan suspension. Pd/C (25.07 mg, 0.024 mmol) was added, and the mixture was stirred under hydrogen (1 atm.) for 6 h. The mixture was filtered, washed, and concentrated to a light tan solid, which was purified using flash chromatography on silica gel, eluting with 0-10% methanol/methylene chloride to afford the desired product (25 mg, 36%) as a white solid: MS (ESI) (m/z): 291 (M+H)$^+$; $^1$H NMR (400 MHz, CDCl3) δ 9.60 (s, 1H), 8.51 (d, J=4.9 Hz, 1H), 8.11 (d, J=5.3 Hz, 1H), 7.95 (s, 1H), 7.63-7.52 (m, 3H), 7.48-7.41 (m, 2H), 7.27 (d, J=5.0 Hz, 1H), 6.85 (s, 1H), 6.60 (dd, J=5.3, 1.5 Hz, 1H), 4.70 (s, 2H).

Example 227

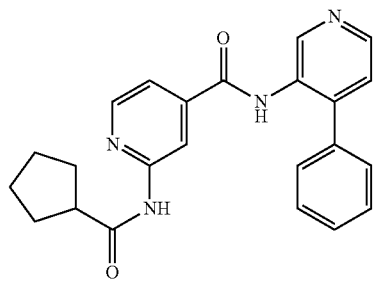 [SMILES: O=C(Nc1cnccc1-c1ccccc1)c1ccnc(NC(=O)C2CCCC2)c1]

2-(Cyclopentanecarboxamido)-N-(4-phenylpyridin-3-yl)isonicotinamide

In a 5 mL vial was dissolved 2-amino-N-(4-phenylpyridin-3-yl)isonicotinamide (8.8 mg, 0.030 mmol) and cyclopentanecarboxylic acid (4.15 mg, 0.036 mmol) in dimethylformamide (0.5 mL) to give a tan solution. HATU (23.05 mg, 0.061 mmol) and Hunig's base (10.59 μl, 0.061 mmol) were added, and the mixture was stirred at rt for 18 h. The mixture was heated at 80° C. overnight. A further 2 equiv. of HATU was added. After 18 h at 80° C., the mixture was purified by prep-HPLC to afford the desired product (5.1 mg, 44%): MS (ESI) (m/z): 387 (M+H)$^+$; $^1$H NMR (500 MHz, DMSO) δ 10.65 (s, 1H), 10.43 (s, 1H), 8.64 (s, 1H), 8.59 (d, J=5.0 Hz, 1H), 8.49 (s, 1H), 8.45 (d, J=5.1 Hz, 1H), 7.55-7.51 (m, 2H), 7.50 (d, J=5.1 Hz, 1H), 7.49-7.44 (m, 2H), 7.43-7.38 (m, 2H), 3.02-2.92 (m, 1H), 1.94-1.80 (m, 2H), 1.78-1.63 (m, 4H), 1.60-1.50 (m, 2H).

Example 212

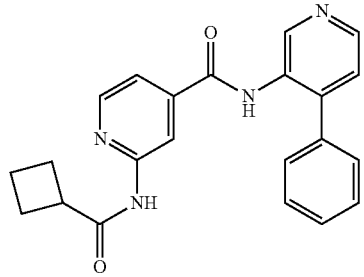 [SMILES: O=C(Nc1cnccc1-c1ccccc1)c1ccnc(NC(=O)C2CCC2)c1]

2-(Cyclobutanecarboxamido)-N-(4-phenylpyridin-3-yl)isonicotinamide

MS (ESI) (m/z): 373 (M+H)$^+$; $^1$H NMR (500 MHz, DMSO) δ 10.52 (s, 1H), 10.44 (s, 1H), 8.64 (s, 1H), 8.59 (d, J=5.0 Hz, 1H), 8.50 (s, 1H), 8.44 (d, J=5.0 Hz, 1H), 7.55-7.51 (m, 2H), 7.50 (d, J=5.0 Hz, 1H), 7.49-7.45 (m,

2H), 7.41 (ddd, J=8.8, 2.8, 1.5 Hz, 2H), 3.45-3.37 (m, 1H), 2.30-2.18 (m, 2H), 2.18-2.07 (m, 2H), 2.02-1.89 (m, 1H), 1.88-1.77 (m, 1H).

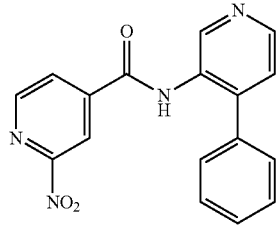

2-Nitro-N-(4-phenylpyridin-3-yl)isonicotinamide

A 100 mL round-bottom flask was charged with 2-nitroisonicotinic acid (412 mg, 2.451 mmol) in methylene chloride (12 mL) to give a white suspension. Dimethylformamide (0.032 mL, 0.408 mmol) was added, followed by oxalyl chloride (0.250 mL, 2.86 mmol) (added dropwise under nitrogen). The solids dissolved within 20 min and the mixture became a tan solution. After stirring at rt for 1 h, the mixture was concentrated in vacuo. 3-Amino-4-phenyl pyridine, dihydrochloride salt (331 mg, 1.361 mmol) was added followed by 10 ml methylene chloride and gradual addition of Hunig's base (1.189 mL, 6.81 mmol). The resulting mixture was stirred at rt for 30 min. The mixture was concentrated and the residue purified using silica gel flash chromatography, eluting with 50% ethyl acetate/hexane to afford the desired product (155 mg, 35%) as a slightly pink solid, as well as the recovered amine (less polar than the product, 132 mg, 57%) as a yellow solid (free base). The desired product: MS (ESI) (m/z): 321 (M+H)+; 1H NMR (400 MHz, CDCl3) δ 9.24 (s, 1H), 9.11 (s, 1H), 8.68 (d, J=4.7 Hz, 1H), 8.47 (s, 1H), 8.33 (d, J=5.0 Hz, 1H), 7.99 (d, J=4.3 Hz, 1H), 7.58-7.45 (m, 3H), 7.45-7.37 (m, 2H), 7.33-7.24 (m, 1H).

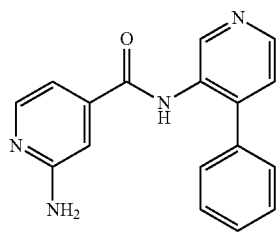 [SMILES: Nc1cc(C(=O)Nc2cnccc2-c2ccccc2)ccn1]

2-Amino-N-(4-phenylpyridin-3-yl)isonicotinamide

A 100 mL round-bottomed flask was charged with 2-nitro-N-(4-phenylpyridin-3-yl)isonicotinamide (153 mg, 0.478 mmol) and Pd/C (50.8 mg, 0.048 mmol) in methanol (4 mL). The mixture was stirred under hydrogen (1 atm.) at rt for 3 h. The mixture was filtered, and concentrated to give a yellow foam (135 mg, 97%): MS (ESI) (m/z): 291 (M+H)+.

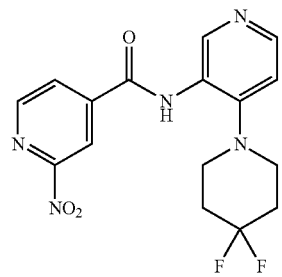 [SMILES: O=C(Nc1cnccc1N1CCC(F)(F)CC1)c1ccnc([N+](=O)[O-])c1]

N-(4-(4,4-difluoropiperidin-1-yl)pyridin-3-yl)-2-nitroisonicotinamide

In a 15 mL vial was 4-(4,4-difluoropiperidin-1-yl)pyridin-3-amine (145 mg, 0.681 mmol) and 2-nitroisonicotinic acid (104 mg, 0.619 mmol) in dimethylformamide (5 mL) to give a tan solution. HATU (470 mg, 1.237 mmol) and Hunig's base (0.216 mL, 1.237 mmol) were added, and the mixture was stirred at rt for 22 h. The mixture was diluted with water and extracted with ethyl acetate. The organic layer was washed with brine, dried and concentrated. The residue was purified using silica gel flash chromatography, eluting with 50% ethyl acetate/hexane to afford the desired product (206 mg, 92%) as a colorless foam: 1H NMR (500 MHz, CDCl3) δ 9.37 (s, 1H), 9.21 (s, 1H), 8.83 (d, J=4.8 Hz, 1H), 8.67 (s, 1H), 8.33 (d, J=5.4 Hz, 1H), 8.19 (d, J=3.9 Hz, 1H), 7.07 (d, J=5.4 Hz, 1H), 3.18-3.14 (m, 4H), 2.18-2.12 (m, 4H); 19F NMR (470 MHz, CDCl3) δ -98.30 (s).

Example 216

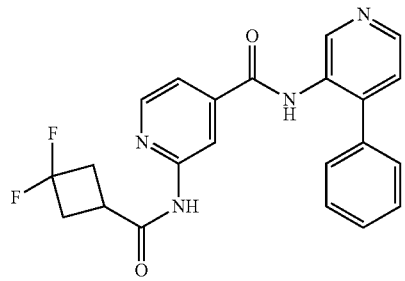 [SMILES: O=C(Nc1cnccc1-c1ccccc1)c1ccnc(NC(=O)C2CC(F)(F)C2)c1]

2-(3,3-Difluorocyclobutanecarboxamido)-N-(4-phenylpyridin-3-yl)isonicotinamide

In a 5 mL vial was dissolved 2-amino-N-(4-phenylpyridin-3-yl)isonicotinamide (7.6 mg, 0.026 mmol) and 3,3-difluorocyclobutanecarboxylic acid (5.34 mg, 0.039 mmol) (1 drop, excess) in dimethylformamide (0.5 mL) to give a tan solution. HATU (19.91 mg, 0.052 mmol) and Hunig's base (9.14 µl, 0.052 mmol) were added, and the mixture was stirred at 85° C. overnight. The mixture was cooled to room temperature and was purified by prep-HPLC to afford the desired product (1.8 mg, 16%): MS (ESI) (m/z): 409 (M+H)+; 1H NMR (500 MHz, DMSO) δ 10.88 (s, 1H), 10.47 (s, 1H), 8.65 (s, 1H), 8.58 (d, J=5.0 Hz, 1H), 8.54-8.42 (m, 2H), 7.54-7.40 (m, 7H), 3.28 (dd, J=10.1, 6.9 Hz, 1H), 2.81 (dd, J=16.6, 8.1 Hz, 4H).

Example 97

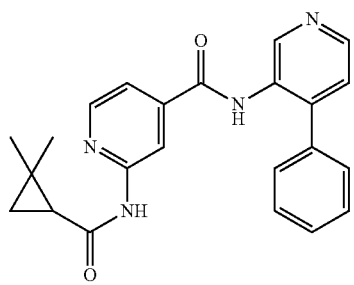 [SMILES: CC1(C)CC1C(=O)Nc1cc(C(=O)Nc2cnccc2-c2ccccc2)ccn1]

2-(2,2-Dimethylcyclopropanecarboxamido)-N-(4-phenylpyridin-3-yl)isonicotinamide

MS (ESI) (m/z): 387 (M+H)⁺.

Example 98

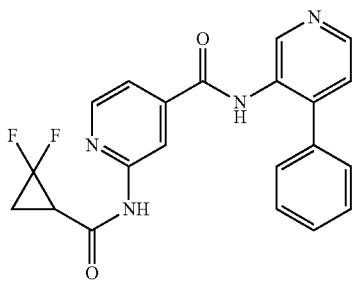 [SMILES: O=C(Nc1cnccc1-c1ccccc1)c1ccnc(NC(=O)C2CC2(F)F)c1]

2-(2,2-Difluorocyclopropanecarboxamido)-N-(4-phenylpyridin-3-yl)isonicotinamide

MS (ESI) (m/z): 395 (M+H)⁺; ¹H NMR (500 MHz, DMSO) δ 11.21 (s, 1H), 10.47 (s, 1H), 8.64 (s, 1H), 8.58 (d, J=5.0 Hz, 1H), 8.50 (d, J=5.0 Hz, 1H), 8.43 (s, 1H), 7.53-7.44 (m, 6H), 7.40 (ddd, J=8.4, 4.2, 1.9 Hz, 1H), 3.08-2.97 (m, 1H), 2.11-2.00 (m, 2H).

Example 99

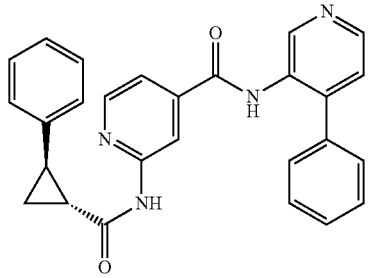 [SMILES: O=C(Nc1cnccc1-c1ccccc1)c1ccnc(NC(=O)[C@@H]2C[C@H]2c2ccccc2)c1]

2-((Trans)-2-phenylcyclopropanecarboxamido)-N-(4-phenylpyridin-3-yl)isonicotinamide MS (ESI) (m/z): 435 (M+H)⁺; ¹H NMR (500 MHz, DMSO) δ 11.01 (s, 1H), 10.45 (s, 1H), 8.64 (s, 1H), 8.59 (d, J=5.0 Hz, 1H), 8.49 (s, 1H), 8.45 (d, J=5.0 Hz, 1H), 7.55-7.44 (m, 5H), 7.41 (t, J=5.0 Hz, 2H), 7.32 (t, J=7.6 Hz, 2H), 7.21 (dd, J=16.7, 7.3 Hz, 3H), 2.47-2.41 (m, 1H), 2.41-2.34 (m, 1H), 1.52 (dt, J=9.2, 4.5 Hz, 1H), 1.46-1.37 (m, 1H).

Example 100

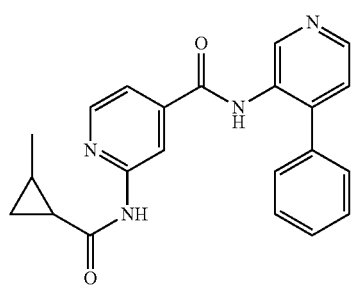 [SMILES: CC1CC1C(=O)Nc1cc(C(=O)Nc2cnccc2-c2ccccc2)ccn1]

2-(2-Methylcyclopropanecarboxamido)-N-(4-phenylpyridin-3-yl)isonicotinamide

MS (ESI) (m/z): 373 (M+H)⁺; ¹H NMR (500 MHz, DMSO) δ 10.90 (s, 1H), 10.43 (s, 1H), 8.63 (s, 1H), 8.57 (d, J=5.0 Hz, 1H), 8.44 (d, J=5.2 Hz, 2H), 7.54-7.43 (m, 5H), 7.39 (dd, J=8.5, 6.1 Hz, 2H), 1.79 (dt, J=8.2, 4.2 Hz, 1H), 1.33-1.23 (m, 1H), 1.11 (d, J=6.0 Hz, 3H), 1.08-1.02 (m, 1H), 0.70 (td, J=8.0, 3.6 Hz, 1H).

Example 185

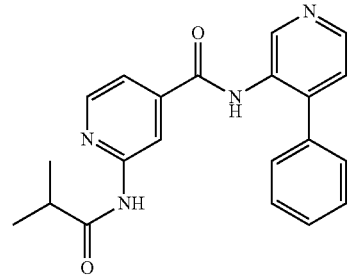 [SMILES: CC(C)C(=O)Nc1cc(C(=O)Nc2cnccc2-c2ccccc2)ccn1]

2-Isobutyramido-N-(4-phenylpyridin-3-yl)isonicotinamide

MS (ESI) (m/z): 361 (M+H)⁺; ¹H NMR (500 MHz, DMSO) δ 10.63 (s, 1H), 10.46 (s, 1H), 8.64 (s, 1H), 8.58 (d, J=5.0 Hz, 1H), 8.53-8.42 (m, 2H), 7.45 (ddt, J=13.2, 9.7, 7.2 Hz, 7H), 2.84-2.69 (m, 1H), 1.11 (d, J=6.8 Hz, 6H).

Example 205

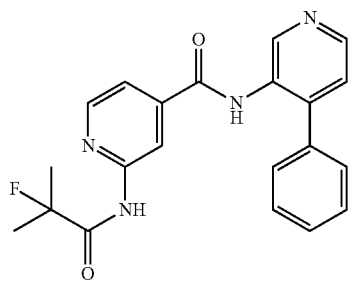 [SMILES: CC(C)(F)C(=O)Nc1cc(C(=O)Nc2cnccc2-c2ccccc2)ccn1]

2-(2-Fluoro-2-methylpropanamido)-N-(4-phenylpyridin-3-yl)isonicotinamide

MS (ESI) (m/z): 379 (M+H)$^+$; $^1$H NMR (500 MHz, DMSO) δ 10.50 (s, 1H), 10.16 (s, 1H), 8.65 (s, 1H), 8.59 (d, J=5.0 Hz, 1H), 8.53 (d, J=5.1 Hz, 1H), 8.39 (s, 1H), 7.56-7.37 (m, 7H), 1.64 (s, 3H), 1.60 (s, 3H).

Example 215

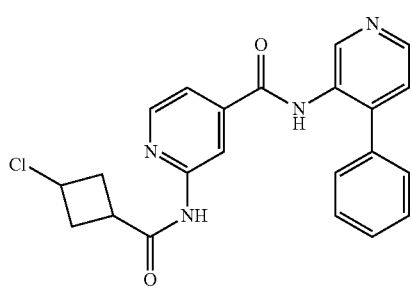 [SMILES: O=C(Nc1cnccc1-c1ccccc1)c1ccnc(NC(=O)C2CC(Cl)C2)c1]

2-(3-Cholorocyclobutanecarboxamido)-N-(4-phenylpyridin-3-yl)isonicotinamide

MS (ESI) (m/z): 407 (M+H)$^+$.

Example 217

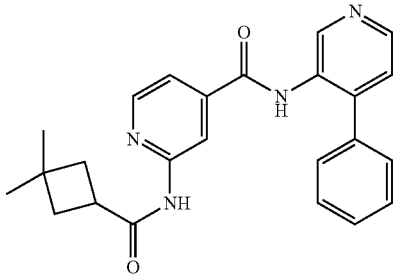 [SMILES: CC1(C)CC(C(=O)Nc2cc(C(=O)Nc3cnccc3-c3ccccc3)ccn2)C1]

2-(3,3-Dimethylcyclobutanecarboxamido)-N-(4-phenylpyridin-3-yl)isonicotinamide

MS (ESI) (m/z): 401 (M+H)$^+$; $^1$H NMR (500 MHz, DMSO) δ 10.50 (s, 1H), 10.43 (s, 1H), 8.65 (s, 1H), 8.59 (d, J=5.0 Hz, 1H), 8.50 (s, 1H), 8.44 (d, J=5.1 Hz, 1H), 7.55-7.44 (m, 5H), 7.40 (dd, J=10.7, 5.3 Hz, 2H), 3.33-3.29 (m, 1H), 2.02 (t, J=10.2 Hz, 2H), 1.95-1.88 (m, 2H), 1.18 (s, 3H), 1.09 (s, 3H).

Example 218

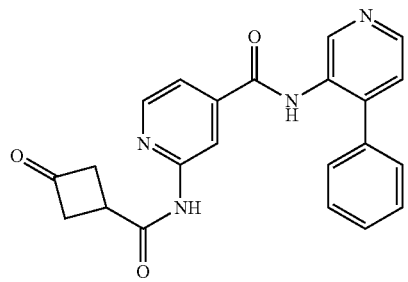 [SMILES: O=C1CC(C(=O)Nc2cc(C(=O)Nc3cnccc3-c3ccccc3)ccn2)C1]

2-(3-Oxocyclobutanecarboxamido)-N-(4-phenylpyridin-3-yl)isonicotinamide

MS (ESI) (m/z): 387 (M+H)$^+$; $^1$H NMR (400 MHz, MeOD/CDCl3) δ 8.82 (s, 1H), 8.64 (d, J=8.2 Hz, 1H), 8.53 (d, J=5.0 Hz, 1H), 8.47 (s, 1H), 8.42 (d, J=5.1 Hz, 1H), 7.73 (s, 1H), 7.54-7.35 (m, 7H), 3.50-3.45 (m, 1H), 1.38 (d, J=6.6 Hz, 4H).

Example 219

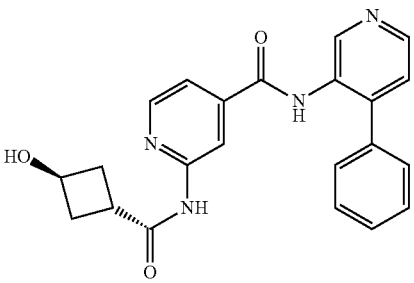

2-((1,3-Trans)-3-hydroxycyclobutanecarboxamido)-N-(4-phenylpyridin-3-yl)isonicotinamide MS (ESI) (m/z): 389 (M+H)$^+$; $^1$H NMR (500 MHz, DMSO) δ 10.59 (s, 1H), 10.46 (s, 1H), 8.64 (s, 1H), 8.58 (d, J=5.0 Hz, 1H), 8.49 (s, 1H), 8.44 (d, J=5.0 Hz, 1H), 7.54 (d, J=7.2 Hz, 2H), 7.51-7.44 (m, 3H), 7.41 (t, J=6.7 Hz, 2H), 5.21 (s, 1H), 3.99 (s, 1H), 2.77 (dd, J=16.1, 8.5 Hz, 1H), 2.37 (dt, J=9.9, 7.4 Hz, 21H), 2.04 (td, J=10.9, 2.6 Hz, 2H).

Example 220

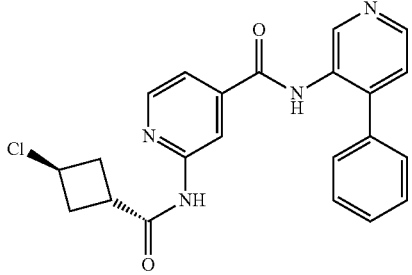

2-((1,3-Trans)-3-chlorocyclobutanecarboxamido)-N-(4-phenylpyridin-3-yl)isonicotinamide MS (ESI) (m/z): 450 (M+H)⁺; ¹H NMR (500 MHz, DMSO) δ 10.80 (s, 1H), 10.09 (s, 1H), 8.63 (s, 1H), 8.57 (s, 1H), 8.53 (d, J=5.1 Hz, 1H), 8.30 (d, J=5.5 Hz, 1H), 7.60 (d, J=4.4 Hz, 1), 7.13 (d, J=5.5 Hz, 1H), 4.65-4.52 (m, 1H), 3.27-3.17 (m, 5H), 2.79-2.72 (m, 2H), 2.47 (ddd, J=18.3, 9.2, 2.8 Hz, 2H), 2.18-2.04 (m, 4H).

Example 221

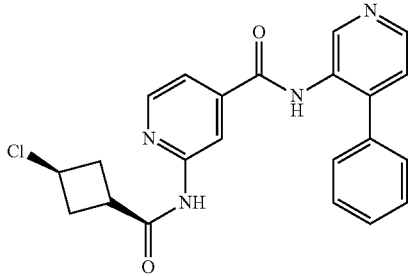

2-((1,3-Cis)-3-chlorocyclobutanecarboxamido)-N-(4-phenylpyridin-3-yl)isonicotinamide MS (ESI) (m/z): 450 (M+H)⁺; ¹H NMR (500 MHz, DMSO) δ 10.78 (s, 1H), 10.08 (s, 1H), 8.64 (s, 1H), 8.59 (s, 1H), 8.53 (d, J=5.0 Hz, 1H), 8.30 (d, J=5.5 Hz, 1H), 7.60 (d, J=4.7 Hz, 1H), 7.14 (d, J=5.5 Hz, 1H), 4.71 (p, J=6.8 Hz, 1H), 3.62 (tt, J=9.7, 4.8 Hz, 1H), 3.24-3.20 (m, 4H), 2.81 (ddd, J=12.3, 7.5, 4.7 Hz, 2H), 2.58-2.52 (m, 2H), 2.13 (ddd, J=19.8, 14.0, 5.5 Hz, 4H).

Example 229

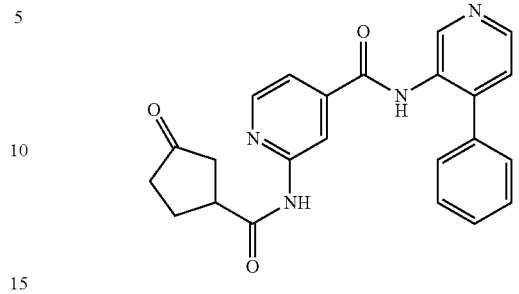

2-(3-Oxocyclopentanecarboxamido)-N-(4-phenylpyridin-3-yl)isonicotinamide

MS (ESI) (m/z): 401 (M+H)⁺; ¹H NMR (400 MHz, MeOD/CDCl3) δ 8.86 (s, 1H), 8.51 (d, J=5.1 Hz, 1H), 8.46-8.37 (m, 2H), 7.48 (dd, J=9.8, 5.0 Hz, 5H), 7.43 (dd, J=6.1, 2.7 Hz, 1H), 7.37 (d, J=5.1 Hz, 1H), 2.67-2.13 (m, 7H).

Example 230

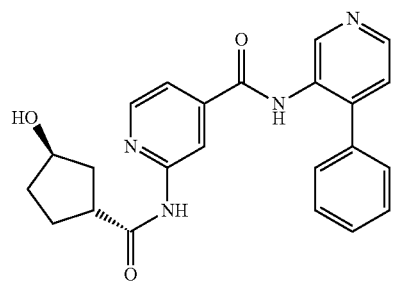

2-((1,3-Trans)-3-hydroxycyclopentanecarboxamido)-N-(4-phenylpyridin-3-yl)isonicotinamide MS (ESI) (m/z): 403 (M+H)⁺; ¹H NMR (500 MHz, DMSO) δ 10.62 (s, 1H), 10.44 (s, 1H), 8.64 (s, 1H), 8.58 (d, J=5.0 Hz, 1H), 8.48 (s, 1H), 8.44 (d, J=5.0 Hz, 1H), 7.55-7.44 (m, 5H), 7.40 (dd, J=8.3, 6.2 Hz, 2H), 4.79 (d, J=4.0 Hz, 1H), 4.14 (s, 1H), 3.00-2.90 (m, 1H), 2.18-2.05 (m, 1H), 1.95-1.77 (m, 2H), 1.77-1.65 (m, 2H), 1.61 (dt, J=16.8, 6.5 Hz, 1H).

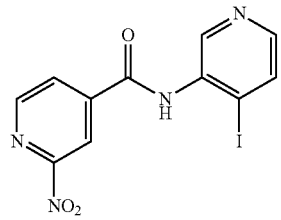 [SMILES: O=C(Nc1cnccc1I)c1ccnc([N+](=O)[O-])c1]

N-(4-iodopyridin-3-yl)-2-nitroisonicotinamide

A 100 mL round-bottomed flask was charged with 2-nitroisonicotinic acid (0.545 g, 3.24 mmol) in methylene chloride (12 mL) to give a white suspension. dimethylformamide (0.025 mL, 0.324 mmol) was added, followed by oxalyl chloride (0.312 mL, 3.57 mmol) (added dropwise under nitrogen). The solids dissolved within 20 min and the mixture became a tan solution. After stirring at rt for 40 min, LCMS showed complete conversion to the acid chloride (as methyl ester). 4-iodopyridin-3-amine (0.856 g, 3.89 mmol) was suspended in 10 ml methylene chloride and cooled at 0° C. The acid chloride solution was slowly added by canuulation, followed by addition of Hunig's base (1.132 mL, 6.48 mmol). The resulting mixture was stirred at rt for 20 h. It was diluted with water and ethyl acetate. The gray solid (0.569 g) was filtered and proved to be the desired product by LCMS. The layers were separated. The organic layer was washed with brine, dried and concentrated. The residue was purified using silica gel flash chromatography, eluting with 50% ethyl acetate/hexane. The combined product (0.699 g, 58%) was used without further purification: MS (ESI) (m/z): 371 (M+H)+.

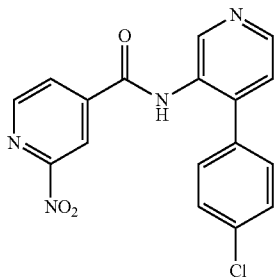 [SMILES: O=C(Nc1cnccc1-c1ccc(Cl)cc1)c1ccnc([N+](=O)[O-])c1]

N-(4-(4-chlorophenyl)pyridin-3-yl)-2-nitroisonicotinamide

In a 15 mL vial was dissolved N-(4-iodopyridin-3-yl)-2-nitroisonicotinamide (130 mg, 0.351 mmol), (4-chlorophenyl)boronic acid (88 mg, 0.562 mmol), and $Na_2CO_3$ (0.527 mL, 1.054 mmol) in dioxane (4 mL) to give a tan solution under nitrogen. 1,1'-Bis(diphenylphosphino) ferrocenepalladium (II) dichloride, toluene (14.45 mg, 0.018 mmol) was added under nitrogen. The vial was sealed and heated at 80° C. for 2 h. The mixture was partitioned between water and ethyl acetate. The layers were separated. The organic layer was washed with brine, dried and concentrated. The residue was purified using silica gel flash chromatography, eluting with 0-8% methanol/methylene chloride to afford the desired product (81 mg, 65%) as a tan oil: MS (ESI) (m/z): 355 (M+H)+; 1H NMR (400 MHz, CDCl3) δ 9.40 (s, 1H), 8.97 (s, 1H), 8.69 (d, J=4.8 Hz, 1H), 8.54 (s, 1H), 8.35 (d, J=5.0 Hz, 1H), 8.03 (d, J=4.3 Hz, 1H), 7.43 (d, J=8.4 Hz, 2H), 7.39-7.30 (m, 2H), 7.30-7.22 (m, 1H).

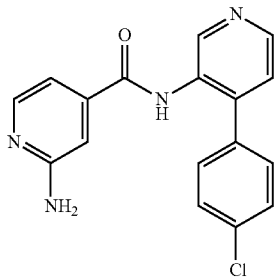 [SMILES: Nc1cc(C(=O)Nc2cnccc2-c2ccc(Cl)cc2)ccn1]

2-Amino-N-(4-(4-chlorophenyl)pyridin-3-yl)isonicotinamide

A 50 mL round-bottom flask was charged with N-(4-(4-chlorophenyl)pyridin-3-yl)-2-nitroisonicotinamide (81 mg, 0.228 mmol) and Pd/C (24.30 mg, 0.023 mmol) in methanol (3 mL). The mixture was stirred under hydrogen (1 atm.) at rt for 2 h. It was filtered, and the combined organic solution was concentrated to a yellow foam (70 mg, 90%): MS (ESI) (m/z): 325 (M+H)+.

Example 186

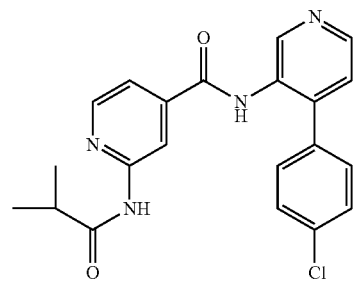 [SMILES: CC(C)C(=O)Nc1cc(C(=O)Nc2cnccc2-c2ccc(Cl)cc2)ccn1]

N-(4-(4-chlorophenyl)pyridin-3-yl)-2-isobutyramidoisonicotinamide

In a 5 mL vial was dissolved 2-amino-N-(4-(4-chlorophenyl)pyridin-3-yl)isonicotinamide (14 mg, 0.043 mmol) and isobutyric acid (7.60 mg, 0.086 mmol) in dimethylformamide (0.5 mL) to give a tan solution. HATU (41.0 mg, 0.108 mmol) and Hunig's base (0.023 mL, 0.129 mmol) were added, and the mixture was stirred at 95° C. for 24 h. The mixture was purified by prep-HPLC to afford the desired product (4.0 mg, 23%): MS (ESI) (m/z): 395 (M+H)+; 1H NMR (500 MHz, DMSO) δ 10.64 (s, 1H), 10.46 (s, 1H), 8.68 (s, 1H), 8.59 (d, J=5.0 Hz, 1H), 8.53-8.41 (m, 2H), 7.55 (s, 4H), 7.50 (d, J=5.0 Hz, 1H), 7.41 (d, J=4.7 Hz, 1H), 2.83-2.71 (m, 1H), 1.13 (s, 3H), 1.11 (s, 3H).

Example 222

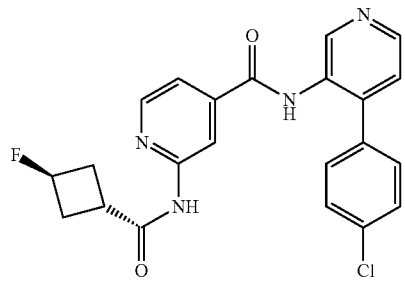

N-(4-(4-chlorophenyl)pyridin-3-yl)-2-((1,3-trans)-3-fluorocyclobutanecarboxamido)isonicotinamide MS (ESI) (m/z): 425 (M+H)+; 1H NMR (500 MHz, DMSO) δ 10.77 (s, 1H), 10.70-10.25 (m, 1H), 8.79 (dd, J=29.0, 5.1 Hz, 1H), 8.72 (d, J=32.8 Hz, 1H), 8.58 (d, J=5.0

Hz, 1H), 8.54-8.43 (m, 2H), 7.60-7.40 (m, 5H), 5.16-4.92 (m, 1H), 2.94-2.79 (m, 1H), 2.63-2.53 (m, 2H), 2.44-2.27 (m, 2H).

Example 223

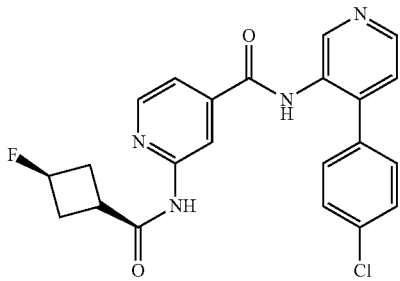

N-(4-(4-chlorophenyl)pyridin-3-yl)-2-((1,3-cis)-3-fluorocyclobutanecarboxamido)isonicotinamide MS (ESI) (m/z): 425 (M+H)$^+$; $^1$H NMR (500 MHz, DMSO) δ 10.76 (s, 1H), 10.49 (s, 1H), 8.70 (s, 1H), 8.56 (d, J=5.0 Hz, 1H), 8.54-8.40 (m, 2H), 7.56 (q, J=8.7 Hz, 4H), 7.49 (d, J=5.0 Hz, 1H), 7.44 (d, J=5.0 Hz, 1H), 5.39-5.14 (m, 1H), 2.62-2.53 (m, 2H), 2.51-2.37 (m, 3H).

Example 224

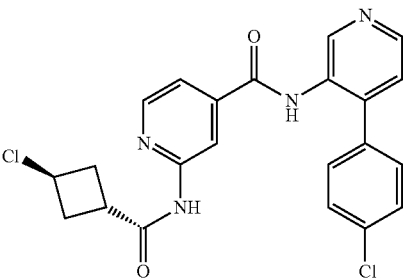

N-(4-(4-chlorophenyl)pyridin-3-yl)-2-((1,3-trans)-3-cholorocyclobutanecarboxamido)isonicotinamide MS (ESI) (m/z): 441 (M+H)$^+$; $^1$H NMR (500 MHz, MeOD) δ 8.82-8.77 (m, 1H), 8.56-8.41 (m, 3H), 7.51-7.33 (m, 6H), 4.50-4.40 (m, 1H), 3.17-3.07 (m, 1H), 2.85-2.75 (m, 2H), 2.65-2.55 (m, 2H).

Example 225

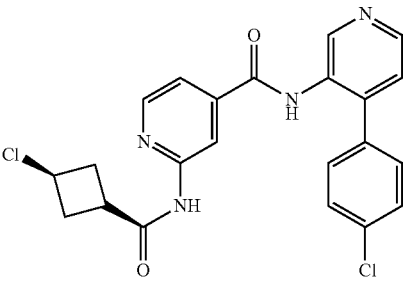

N-(4-(4-chlorophenyl)pyridin-3-yl)-2-((1,3-cis)-3-cholorocyclobutanecarboxamido)isonicotinamide MS (ESI) (m/z): 441 (M+H)$^+$; $^1$H NMR (500 MHz, MeOD) δ 8.81 (s, 1H), 8.56 (d, J=5.2 Hz, 1H), 8.48 (s, 1H), 8.42 (d, J=5.0 Hz, 1H), 7.54-7.47 (m, 6H), 4.78-4.66 (m, 1H), 3.53 (dt, J=9.5, 4.9 Hz, 1H), 2.90 (ddd, J=10.0, 7.3, 3.5 Hz, 2H), 2.58 (ddd, J=13.5, 9.7, 6.6 Hz, 2H).

Example 231

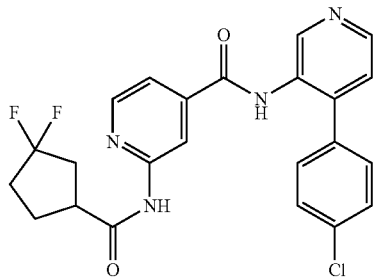 [SMILES: O=C(Nc1cnccc1-c1ccc(Cl)cc1)c1ccnc(NC(=O)C2CCC(F)(F)C2)c1]

N-(4-(4-chlorophenyl)pyridin-3-yl)-2-(3,3-difluorocyclopentanecarboxamido)isonicotinamide MS (ESI) (m/z): 457 (M+H)$^+$; $^1$H NMR (500 MHz, DMSO) δ 10.83 (s, 1H), 10.51 (s, 1H), 8.68 (s, 1H), 8.58 (d, J=5.0 Hz, 1H), 8.54-8.41 (m, 2H), 7.60-7.52 (m, 4H), 7.50 (d, J=5.0 Hz, 1H), 7.45 (d, J=4.7 Hz, 1H), 3.30 (m, 1H), 2.38 (dt, J=18.5, 11.9 Hz, 2H), 2.30-2.03 (m, 3H), 2.00-1.86 (m, 1H).

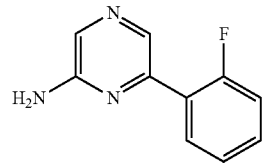 [SMILES: Nc1cncc(-c2ccccc2F)n1]

6-(2-Fluorophenyl)pyrazin-2-amine

In a 15 mL vial was dissolved 2-bromo-6-amino-pyrazine (218 mg, 1.25 mmol), (2-fluorophenyl)boronic acid (280 mg, 2.005 mmol), and Na$_2$CO$_3$ (1.879 mL, 3.76 mmol) in dioxane (6 mL) to give a tan solution under nitrogen. 1,1'-bis(diphenylphosphino)ferrocenepalladium(II) dichloride, toluene (51.5 mg, 0.063 mmol) was added under nitrogen. The vial was sealed and heated at 135° C. for 2 h. The mixture was partitioned between water and ethyl acetate. The layers were separated. The organic layer was washed with brine, dried and concentrated. The residue was purified using silica gel flash chromatography, eluting with 0-60% ethyl acetate/hexane to afford the desired product (211 mg, 89%) as an off-white solid: MS (ESI) (m/z): 190 (M+H)$^+$; $^1$H NMR (400 MHz, CDCl$_3$) δ 8.39 (d, J=2.7 Hz, 1H), 7.93 (s, 1H), 7.88 (td, J=7.8, 1.8 Hz, 1H), 7.43-7.33 (m, 1H), 7.24 (td, J=7.6, 1.0 Hz, 1H), 7.15 (ddd, J=11.1, 8.3, 0.8 Hz, 1H), 4.99 (s, 2H); 19F NMR (376 MHz, CDCl3) δ −114.88 (s).

Example 180

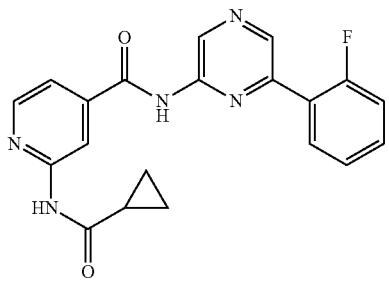

2-(Cyclopropanecarboxamido)-N-(6-(2-fluorophenyl)pyrazin-2-yl)isonicotinamide

In a 5 mL vial was dissolved 6-(2-fluorophenyl)pyrazin-2-amine (18.3 mg, 0.097 mmol) and 2-(cyclopropanecarboxamido)isonicotinic acid (29.9 mg, 0.145 mmol) in dimethylformamide (0.5 mL) to give a colorless solution. HATU (73.6 mg, 0.193 mmol) and Hunig's base (0.034 mL, 0.193 mmol) were added, and the mixture was stirred at 85° C. for 24 h. The mixture was purified by prep-HPLC to afford the desired product (9.0 mg, 24%): MS (ESI) (m/z): 378 (M+H)$^+$; $^1$H NMR (500 MHz, DMSO) δ 11.06 (s, 1H), 9.40 (s, 1H), 8.84 (d, J=2.5 Hz, 11), 8.61 (s, 1H), 8.52 (d, J=5.0 Hz, 1H), 8.01 (td, J=7.8, 1.6 Hz, 1H), 7.65 (dd, J=5.1, 1.5 Hz, 1H), 7.63-7.55 (m, 1H), 7.49-7.39 (m, 2H), 2.11-2.01 (m, 1H), 0.90-0.81 (m, 4H).

Example 207

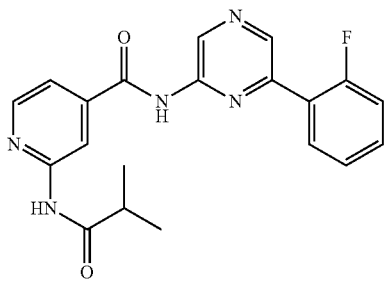 [SMILES: CC(C)C(=O)Nc1cc(C(=O)Nc2cncc(-c3ccccc3F)n2)ccn1]

N-(6-(2-fluorophenyl)pyrazin-2-yl)-2-isobutyramidoisonicotinamide

MS (ESI) (m/z): 380 (M+H)$^+$; $^1$H NMR (500 MHz, DMSO) δ 11.55 (s, 1H), 10.69 (s, 1H), 9.40 (s, 1H), 8.83 (d, J=2.4 Hz, 1H), 8.64 (s, 1H), 8.51 (d, J=5.1 Hz, 1H), 8.02 (td, J=7.8, 1.6 Hz, 1H), 7.65 (dd, J=5.1, 1.5 Hz, 1H), 7.63-7.55 (m, 1H), 7.49-7.38 (m, 2H), 2.88-2.75 (m, 1H), 1.13 (d, J=6.8 Hz, 6H).

Example 208

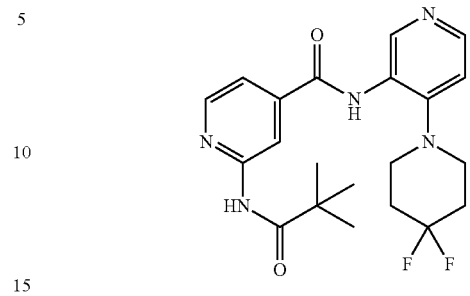

N-(4-(4,4-difluoropiperidin-1-yl)pyridin-3-yl)-2-pivalamidoisonicotinamide

In a 15 mL vial was dissolved 4-(4,4-difluoropiperidin-1-yl)pyridin-3-amine (23.43 mg, 0.110 mmol) and 2-pivalamidoisonicotinic acid (22.2 mg, 0.100 mmol) in dimethylformamide (0.8 mL) to give a tan solution. HATU (76 mg, 0.200 mmol) and Hunig's Base (0.035 mL, 0.200 mmol) were added, and the mixture was stirred at rt over two days. The mixture was purified by prep-HPLC to afford the desired product (9.3 mg, 22%): MS (ESI) (m/z): 418 (M+H)$^+$; $^1$H NMR (500 MHz, DMSO) δ 10.12 (s, 1H), 10.06 (s, 1H), 8.55 (s, 1H), 8.54 (d, J=5.1 Hz, 1H), 8.39 (s, 1H), 8.29 (d, J=5.6 Hz, 1H), 7.61 (d, J=5.0 Hz, 1H), 7.09 (d, J=5.6 Hz, 1H), 3.43 (t, J=11.7 Hz, 2H), 3.20 (s, 2H), 2.11-1.97 (m, 2H), 1.78 (s, 2H), 1.27 (s, 9H).

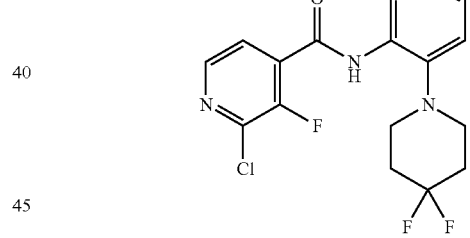

2-Chloro-N-(4-(4,4-difluoropiperidin-1-yl)pyridin-3-yl)-3-fluoroisonicotinamide

In a 15 mL vial was dissolved 4-(4,4-difluoropiperidin-1-yl)pyridin-3-amine (139 mg, 0.650 mmol) and 2-chloro-3-fluoroisonicotinic acid (103.8 mg, 0.591 mmol) in dimethylformamide (4 mL) to give a tan solution. HATU (450 mg, 1.183 mmol) and Hunig's base (0.207 mL, 1.183 mmol) were added, and the mixture was stirred at rt for 22 h. It was diluted with water and extracted with ethyl acetate. The organic layer was washed with brine, dried and concentrated. The residue was purified using silica gel flash chromatography, eluting with 50% ethyl acetate/hexane to afford the desired product (31.8 mg, 14.5%) as a tan oil: MS (ESI) (m/z): 371 (M+H)$^+$; $^1$H NMR (400 MHz, MeOD) δ 9.14 (s, 1H), 8.37 (d, J=5.0 Hz, 1H), 8.30 (dd, J=4.6, 3.7 Hz, 1H), 7.81 (t, J=4.9 Hz, 1H), 7.39 (dd, J=8.4, 4.4 Hz, 1H), 7.19 (d, J=5.8 Hz, 1H), 3.38-3.31 (m, 2H), 3.25-3.18 (m, 2H), 2.16-2.02 (m, 2H), 2.01-1.91 (m, 2H); $^{19}$F NMR (376 MHz, MeOD) δ −73.28 (s), −75.17 (s).

Example 206

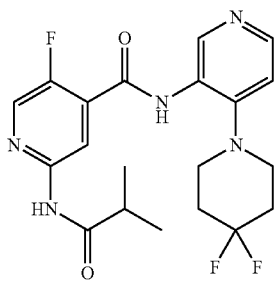 [SMILES: CC(C)C(=O)Nc1cc(C(=O)Nc2cnccc2N2CCC(F)(F)CC2)c(F)cn1]

N-(4-(4,4-difluoropiperidin-1-yl)pyridin-3-yl)-5-fluoro-2-isobutyramidoisonicotinamide In a 5 mL microwave tube was added 2-chloro-N-(4-(4,4-difluoropiperidin-1-yl)pyridin-3-yl)-5-fluoroisonicotinamide (24 mg, 0.065 mmol), isobutyramide (11.28 mg, 0.129 mmol), and K$_2$CO$_3$ (13.42 mg, 0.097 mmol) in dioxane (0.5 mL) (degassed) to give a colorless suspension under nitrogen. Pd(OAc)$_2$ (1.453 mg, 6.47 μmol) and XANTPHOS (7.49 mg, 0.013 mmol) were added. The vial was sealed and heated at 150° C. for 2 h. The mixture was partitioned between water and ethyl acetate. The organic solution was dried and concentrated. The residue was dissolved in dimethylformamide, and purified by prep-HPLC to afford the desired product (3.7 mg, 13%): MS (ESI) (m/z): 422 (M+H)$^+$; $^1$H NMR (500 MHz, DMSO) δ 10.73 (s, 1H), 10.06 (s, 1H), 8.56 (s, 1H), 8.52 (s, 1H), 8.47 (d, J=5.2 Hz, 1H), 8.30 (d, J=5.5 Hz, 1H), 7.11 (d, J=5.5 Hz, 1H), 3.45 (t, J=11.6 Hz, 2H), 3.19 (s, 2H), 2.78 (dt, J=13.4, 6.8 Hz, 1H), 2.05 (dt, J=20.4, 7.0 Hz, 2H), 1.83 (s, 2H), 1.12 (d, J=6.8 Hz, 6H).

Example 228

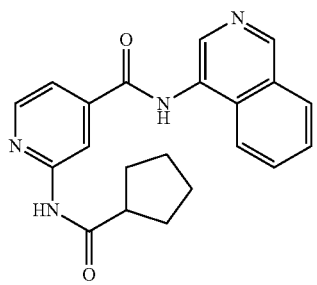 [SMILES: O=C(Nc1cncc2ccccc12)c1ccnc(NC(=O)C2CCCC2)c1]

2-(Cyclopentanecarboxamido)-N-(isoquinolin-4-yl)isonicotinamide

In a 5 mL round-bottom flask was dissolved 2-(cyclopentanecarboxamido)isonicotinic acid (36 mg, 0.154 mmol) and isoquinolin-4-amine (26.6 mg, 0.184 mmol) in dimethylformamide (0.8 mL) to give a tan solution. HATU (117 mg, 0.307 mmol) and Hunig's Base (0.054 mL, 0.307 mmol) were added, and the mixture was stirred at rt overnight for 19 h. The desired product was obtained by prep-HPLC (5.9 mg, 10%): MS (ESI) (m/z): 361 (M+H)$^+$; $^1$H NMR (400 MHz, DMSO) δ 10.81 (s, 1H), 10.67 (s, 1H), 9.32 (s, 1H), 8.69 (s, 1H), 8.65 (s, 1H), 8.59-8.51 (m, 1H), 8.30-8.20 (m, 1H), 8.07-7.99 (m, 1H), 7.91-7.84 (m, 1H), 7.82-7.74 (m, 1H), 7.73-7.66 (m, 1H), 3.05-2.98 (m, 1H), 1.95-1.85 (m, 2H), 1.83-1.66 (m, 4H), 1.64-1.54 (m, 2H).

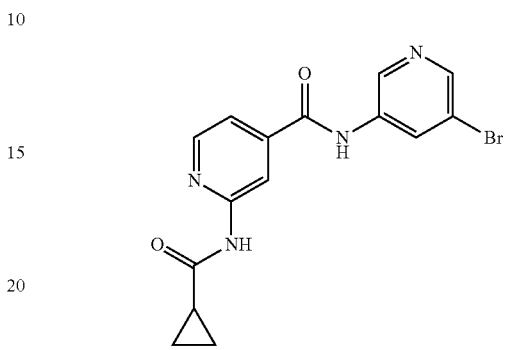

N-(5-bromopyridin-3-yl)-2-(cyclopropanecarboxamido)isonicotinamide

To 5-bromopyridin-3-amine (0.2 g, 1.156 mmol) and 2-(cyclopropanecarboxamido)isonicotinic acid (0.238 g, 1.156 mmol) in dimethylformamide (2 mL) was added DIEA (1.009 mL, 5.78 mmol) followed by 1-propanephosphonic acid cyclic anhydride (0.675 mL, 2.312 mmol) dropwise. The reaction was stirred at rt for 3 days, and then heated to 80° C. for 3 h. The reaction was diluted with ethyl acetate and water. The organic extracts were washed with brine and dried over sodium sulfate and evaporated. The crude product was purified using silica gel flash chromatography, eluting with 0-100% ethyl acetate/hexanes to the desired product (0.155 g, 0.429 mmol, 37% yield) as white solid. $^1$H NMR (500 MHz, Chloroform-d) δ ppm 8.67 (d, J=2.14 Hz, 1H) 8.58 (s, 1H) 8.54-8.57 (m, 1H) 8.47-8.53 (m, 2H) 8.27 (d, J=9.46 Hz, 2H) 7.60 (dd, J=5.19, 1.53 Hz, 1H) 1.61-1.64 (m, 1H) 1.11-1.20 (m, 2H) 0.95-1.04 (m, 2H).

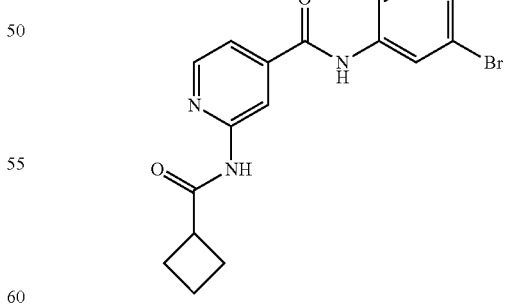

2-(cyclopropanecarboxamido)-N-(5-bromopyridin-3-yl)isonicotinamide

MS (ESI) (m/z): 375 (M+H)$^+$.

Example 102

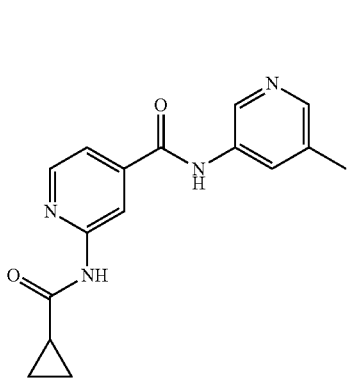 [SMILES: Cc1cncc(NC(=O)c2ccnc(NC(=O)C3CC3)c2)c1]

2-(cyclopropanecarboxamido)-N-(5-methylpyridin-3-yl)isonicotinamide $^1$H NMR (500 MHz, DMSO-d$_6$) δ ppm 11.06 (s, 1H) 10.66 (s, 1H) 8.72 (d, J=2.44 Hz, 1H) 8.44-8.58 (m, 2H) 8.21 (d, J=1.22 Hz, 1H) 7.99-8.08 (m, 1H) 7.56 (dd, J=5.19, 1.53 Hz, 1H) 2.33 (d, J=0.61 Hz, 3H) 2.03-2.13 (m, 1H) 0.77-0.94 (m, 4H). MS (ESI) (m/z): 297.2 (M+H)$^+$.

Example 150

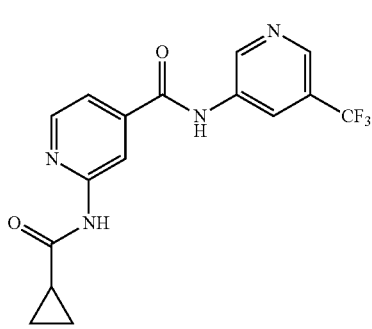 [SMILES: O=C(Nc1cncc(C(F)(F)F)c1)c1ccnc(NC(=O)C2CC2)c1]

2-(cyclopropanecarboxamido)-N-(5-(trifluoromethyl)pyridin-3-yl)isonicotinamide $^1$H NMR (500 MHz, DMSO-d$_6$) δ ppm 11.01-11.11 (m, 2H) 9.19 (d, J=1.83 Hz, 1H) 8.75 (s, 1H) 8.60-8.63 (m, 1H) 8.58 (s, 1H) 8.55 (d, J=5.19 Hz, 1H) 7.59 (dd, J=5.19, 1.53 Hz, 1H) 2.03-2.10 (m, 1H) 0.83-0.90 (m, 4H). MS (ESI) (m/z): 351.2 (M+H)$^+$.

Example 171

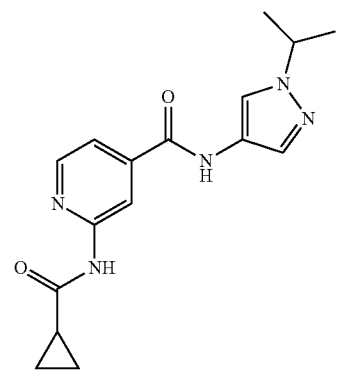 [SMILES: CC(C)n1cc(NC(=O)c2ccnc(NC(=O)C3CC3)c2)cn1]

2-(cyclopropanecarboxamido)-N-(1-isopropyl-1H-pyrazol-4-yl)isonicotinamide $^1$H NMR (500 MHz, DMSO-d) δ ppm 11.01 (s, 1H) 10.69 (br. s., 1H) 8.50-8.54 (m, 1H) 8.49 (dd, J=5.19, 0.92 Hz, 1H) 8.08 (d, J=0.61 Hz, 1H) 7.61 (d, J=0.61 Hz, 1H) 7.53 (dd, J=5.19, 1.53 Hz, 1H) 4.51 (quin, J=6.64 Hz, 1H) 1.99-2.10 (m, 1H) 1.42 (d, J=6.71 Hz, 6H) 0.76-0.91 (m, 4H). MS (ESI) (m/z): 314.1 (M+H)$^+$.

Example 172

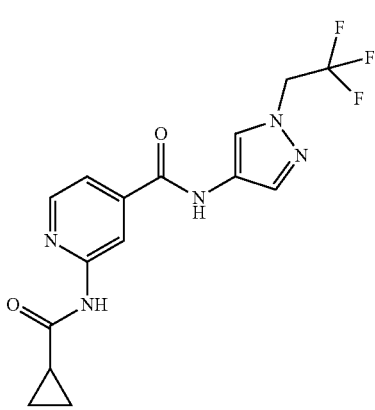 [SMILES: O=C(Nc1cnn(CC(F)(F)F)c1)c1ccnc(NC(=O)C2CC2)c1]

2-(cyclopropanecarboxamido)-N-(1-(2,2,2-trifluoroethyl)-1H-pyrazol-4-yl)isonicotinamide $^1$H NMR (500 MHz, DMSO-d$_6$) δ ppm 11.03 (br. s., 1H) 10.82 (br. s., 1H) 8.53-8.56 (m, 1H) 8.50 (dd, J=5.04, 0.76 Hz, 1H) 8.27 (s, 1H) 7.74 (d, J=0.61 Hz, 1H) 7.54 (dd, J=5.19, 1.53 Hz, 1H) 5.16 (q, J=9.36 Hz, 2H) 2.02-2.10 (m, 1H) 0.83-0.89 (m, 4H). MS (ESI) (m/z): 354.0 (M+H)$^+$.

Example 173

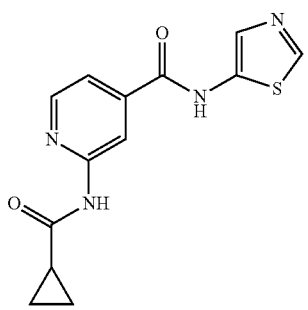 [SMILES: O=C(Nc1cncs1)c1ccnc(NC(=O)C2CC2)c1]

2-(cyclopropanecarboxamido)-N-(thiazol-5-yl)isonicotinamide

¹H NMR (500 MHz, DMSO-d₆) δ ppm 12.04 (br. s., 1H) 11.06 (s, 1H) 8.66 (s, 1H) 8.58-8.63 (m, 1H) 8.53 (d, J=5.19 Hz, 1H) 7.84 (s, 1H) 7.60 (dd, J=5.19, 1.53 Hz, 1H) 2.01-2.12 (m, 1H) 0.83-0.92 (m, 4H). MS (ESI) (m/z): 289.0 (M+H)⁺.

Example 175

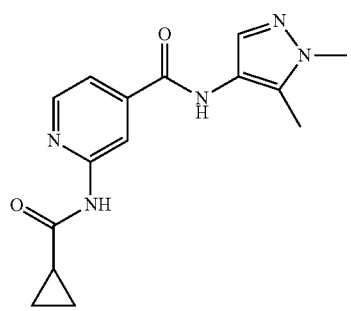 [SMILES: Cc1c(NC(=O)c2ccnc(NC(=O)C3CC3)c2)cnn1C]

2-(cyclopropanecarboxamido)-N-(1,5-dimethyl-1H-pyrazol-4-yl)isonicotinamide

¹H NMR (400 MHz, DMSO-d₆) δ ppm 10.95 (s, 1H) 9.93 (s, 1H) 8.49-8.53 (m, 1H) 8.47 (dd, J=5.02, 0.75 Hz, 1H) 7.53 (dd, J=5.14, 1.63 Hz, 1H) 7.49 (s, 1H) 3.74 (s, 3H) 2.20 (s, 3H) 1.99-2.09 (m, 1H) 0.82-0.89 (m, 4H). MS (ESI) (m/z): 300.1 (M+H)⁺.

Example 177

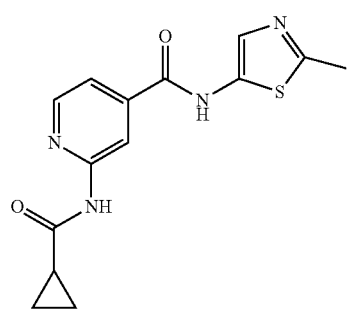 [SMILES: Cc1ncc(NC(=O)c2ccnc(NC(=O)C3CC3)c2)s1]

2-(cyclopropanecarboxamido)-N-(2-methylthiazol-5-yl)isonicotinamide

¹H NMR (400 MHz, DMSO-d₆) δ ppm 11.82 (br. s., 1H) 11.01 (s, 1H) 8.55-8.59 (m, 1H) 8.52 (dd, J=5.15, 0.63 Hz, 1H) 7.58 (dd, J=5.14, 1.63 Hz, 1H) 7.55 (s, 1H) 2.59 (s, 3H) 2.02-2.10 (m, 1H) 0.84-0.89 (m, 4H). MS (ESI) (m/z): 303.1 (M+H)⁺.

Example 101

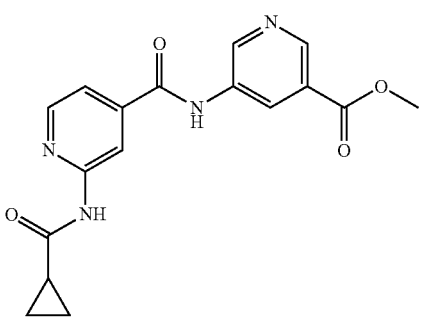 [SMILES: COC(=O)c1cncc(NC(=O)c2ccnc(NC(=O)C3CC3)c2)c1]

Methyl 5-(2-(cyclopropanecarboxamido)isonicotinamido)nicotinate

¹H NMR (500 MHz, DMSO-d₆) δ ppm 11.08 (s, 1H) 10.95 (br. s., 1H) 9.17 (d, J=2.44 Hz, 1H) 8.86 (d, J=1.83 Hz, 1H) 8.74-8.81 (m, 1H) 8.58 (d, J=0.61 Hz, 1H) 8.53-8.56 (m, 1H) 7.60 (dd, J=5.19, 1.53 Hz, 1H) 3.93 (s, 3H) 2.02-2.09 (m, 1H) 0.84-0.89 (m, 4H). MS (ESI) (m/z): 341.0 (M+H)⁺.

Example 103

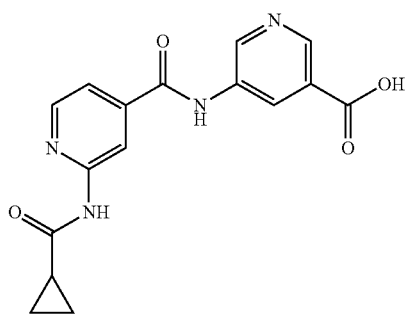 [SMILES: O=C(O)c1cncc(NC(=O)c2ccnc(NC(=O)C3CC3)c2)c1]

5-(2-(cyclopropanecarboxamido)isonicotinamido)nicotinic Acid

To a solution of methyl 5-(2-(cyclopropanecarboxamido)isonicotinamido)nicotinate in tetrahydrofuran (2 mL) and methanol (0.2 mL) was added 2 N LiOH (1.8 mL, 3.60 mmol). The reaction was stirred at rt overnight. The solvent was removed in vacuo, and then re-dissolved in ethyl acetate and 1N HCl. The organic layer was collected, and dried over sodium sulfate, filtered and evaporated. The residue was dried in vacuo to give the desired product (0.02 g, 0.061 mmol, 83% yield). ¹H NMR (500 MHz, DMSO-d₆) δ ppm 11.06 (s, 1H) 10.82 (s, 1H) 9.06 (s, 1H) 8.80 (d, J=1.83 Hz, 1H) 8.64 (br. s., 1H) 8.57 (s, 1H) 8.53 (dd, J=5.19, 0.61 Hz, 1H) 7.97 (s, 1H) 7.60 (dd, J=5.19, 1.53 Hz, 1H) 2.01-2.11 (m, 1H) 0.82-0.90 (m, 4H). MS (ESI) (m/z): 327.2 (M+H)⁺.

Example 105

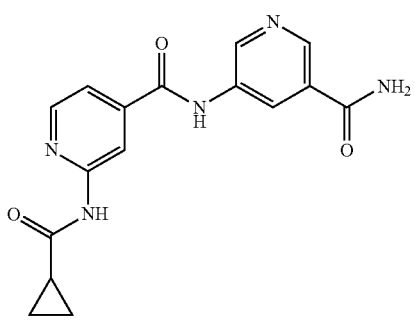 [SMILES: NC(=O)c1cncc(NC(=O)c2ccnc(NC(=O)C3CC3)c2)c1]

5-(2-(cyclopropanecarboxamido)isonicotinamido) nicotinamide

In a small round bottom flask, 5-(2-(cyclopropanecarboxamido)isonicotinamido)nicotinic acid (0.015 g, 0.046 mmol) was dissolved in dimethylformamide (2 mL). To this solution was added HATU (0.026 g, 0.069 mmol) and DIEA (0.080 mL, 0.460 mmol). Finally, ammonium chloride (0.020 g, 0.368 mmol) was added and the reaction mixture was stirred at rt for 3 h. The crude material was purified via preparative LC. ¹H NMR (500 MHz, DMSO-d₆) δ ppm 11.06 (s, 1H) 10.90 (br. s., 1H) 9.05 (d, J=2.44 Hz, 1H) 8.81 (d, J=1.83 Hz, 1H) 8.61 (t, J=2.14 Hz, 1H) 8.57 (d, J=1.53 Hz, 1H) 8.52-8.55 (m, 1H) 8.21 (s, 1H) 7.97 (s, 1H) 7.63 (s, 1H) 7.60 (dd, J=5.19, 1.53 Hz, 1H) 2.02-2.10 (m, 1H) 0.82-0.89 (m, 4H). MS (ESI) (m/z): 326.1 (M+H)⁺.

Example 104

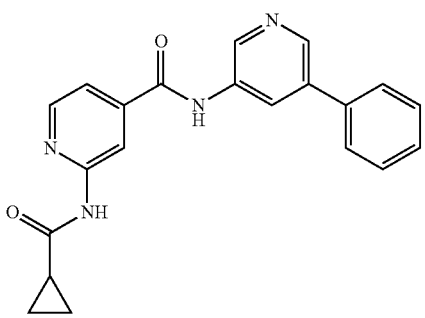

2-(cyclopropanecarboxamido)-N-(5-phenylpyridin-3-yl)isonicotinamide

To N-(5-bromopyridin-3-yl)-2-(cyclopropanecarboxamido)isonicotinamide (26 mg, 0.072 mmol) and phenylboronic acid (8.78 mg, 0.072 mmol) was added dimethylformamide (2 mL). The reaction was stirred at rt until all solids dissolved. Then, [1,1'-bis(diphenylphosphino) ferrocene]dichloropalladium (II) complex with dichloromethane (1:1) (11.76 mg, 0.014 mmol) was added. The flask was degassed and flushed with nitrogen and then 2 M sodium carbonate, (0.054 mL, 0.108 mmol) was added dropwise. The flask was degassed and flushed with nitrogen and then reaction vessel was sealed and then heated at 80° C. for 2.5 h. The reaction was diluted with ethyl acetate and saturated ammonium chloride. The organic layer was washed with water, brine and dried over sodium sulfate. The crude material was purified via preparative LC. ¹H NMR (500 MHz, DMSO-d₆) δ ppm 11.08 (s, 1H) 10.83 (br. s., 1H) 8.95 (d, J=2.14 Hz, 1H) 8.68 (d, J=1.83 Hz, 1H) 8.58 (d, J=0.61 Hz, 1H) 8.55 (dd, J=5.04, 0.76 Hz, 1H) 8.46 (t, J=2.29 Hz, 1H) 7.73 (dd, J=8.24, 1.22 Hz, 2H) 7.60 (dd, J=5.19, 1.53 Hz, 1H) 7.55 (t, J=7.63 Hz, 2H) 7.45-7.50 (m, 1H) 2.03-2.10 (m, 1H) 0.84-0.89 (m, 4H). MS (ESI) (m/z): 359.1 (M+H)⁺.

Example 106

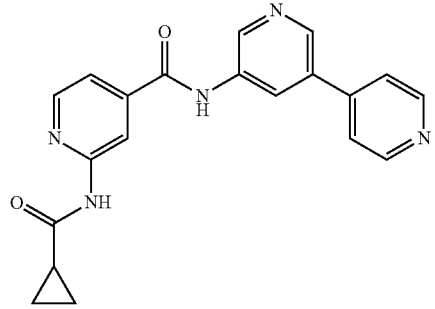 [SMILES: O=C(Nc1cncc(-c2ccncc2)c1)c1ccnc(NC(=O)C2CC2)c1]

N-([3,4'-bipyridin]-5-yl)-2-(cyclopropanecarboxamido)isonicotinamide

¹H NMR (500 MHz, DMSO-d₆) δ ppm 11.08 (s, 1H) 10.89 (s, 1H) 9.02 (d, J=2.14 Hz, 1H) 8.81 (d, J=1.83 Hz, 1H) 8.69-8.75 (m, 2H) 8.59 (s, 1H) 8.58 (t, J=2.14 Hz, 1H) 8.56 (dd, J=5.04, 0.76 Hz, 1H) 7.77-7.80 (m, 2H) 7.60 (dd, J=5.19, 1.53 Hz, 1H) 2.03-2.10 (m, 1H) 0.83-0.89 (m, 4H). MS (ESI) (m/z): 360.1 (M+H)⁺.

Example 111

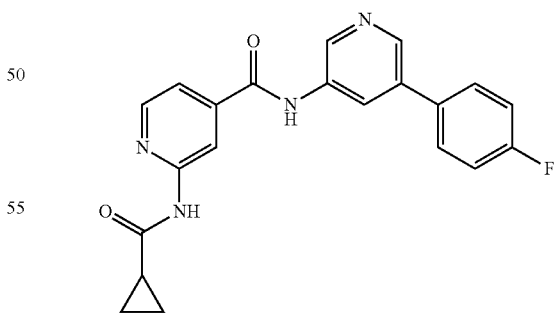

2-(cyclopropanecarboxamido)-N-(5-(4-fluorophenyl) pyridin-3-yl)isonicotinamide

¹H NMR (400 MHz, DMSO-d₆) δ ppm 11.04 (s, 1H) 10.80 (br. s., 1H) 8.93 (d, J=2.20 Hz, 1H) 8.66 (d, J=1.96 Hz, 1H) 8.57 (s, 1H) 8.54 (d, J=5.14 Hz, 1H) 8.43 (t, J=2.20 Hz, 1H) 7.77 (dd, J=8.80, 5.38 Hz, 2H) 7.59 (dd, J=5.14, 1.22 Hz, 1H) 7.37 (t, J=8.80 Hz, 2H) 2.02-2.10 (m, 1H) 0.84-0.89 (m, 4H). MS (ESI) (m/z): 377.2 (M+H)⁺.

Example 112

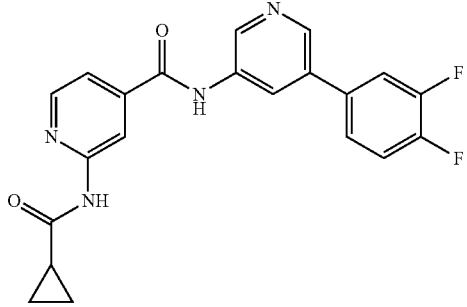 [SMILES: O=C(Nc1cncc(-c2ccc(F)c(F)c2)c1)c1ccnc(NC(=O)C2CC2)c1]

2-(cyclopropanecarboxamido)-N-(5-(3,4-difluoro-phenyl)pyridin-3-yl)isonicotinamide ¹H NMR (400 MHz, DMSO-d₆) δ ppm 11.05 (s, 1H) 10.81 (br. s., 1H) 8.94 (d, J=2.20 Hz, 1H) 8.69 (d, J=1.96 Hz, 1H) 8.57 (s, 1H) 8.54 (d, J=5.14 Hz, 1H) 8.45 (t, J=2.08 Hz, 1H) 7.83-7.90 (m, 1H) 7.56-7.64 (m, 3H) 2.02-2.10 (m, 1H) 0.84-0.89 (m, 4H). MS (ESI) (m/z): 395.1 (M+H)⁺.

Example 114

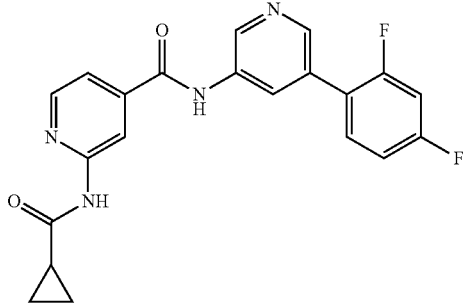 [SMILES: O=C(Nc1cncc(-c2ccc(F)cc2F)c1)c1ccnc(NC(=O)C2CC2)c1]

2-(cyclopropanecarboxamido)-N-(5-(2,4-difluoro-phenyl)pyridin-3-yl)isonicotinamide ¹H NMR (400 MHz, METHANOL-d₄) δ ppm 8.95 (d, J=2.45 Hz, 1H) 8.56 (s, 1H) 8.49-8.53 (m, 2H) 8.46 (s, 1H) 7.65 (td, J=8.86, 6.48 Hz, 2H) 7.57 (dd, J=5.14, 1.47 Hz, 1H) 7.12-7.22 (m, 3H) 1.91-1.98 (m, 1H) 1.01-1.07 (m, 2H) 0.91-0.97 (m, 2H). MS (ESI) (m/z): 395.1 (M+H)⁺.

Example 115

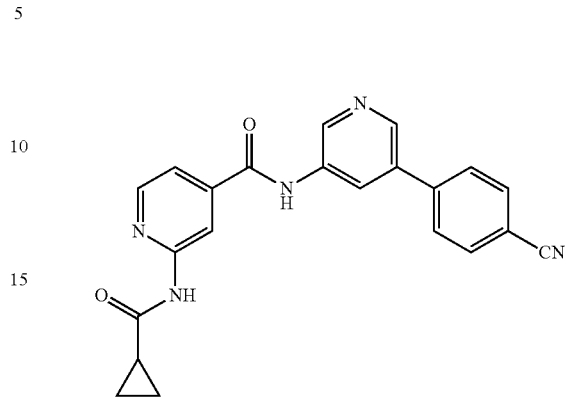

N-(5-(4-cyanophenyl)pyridin-3-yl)-2-(cyclopropan-ecarboxamido)isonicotinamide

¹H NMR (400 MHz, Methanol-d₄) δ ppm 8.97 (s, 1H) 8.69 (d, J=1.71 Hz, 1H) 8.62 (s, 1H) 8.58 (s, 1H) 8.51 (d, J=4.89 Hz, 1H) 7.92 (s, 4H) 7.89 (d, J=2.20 Hz, 1H) 7.58 (d, J=5.14 Hz, 1H) 1.94 (s, 1H) 1.04 (d, J=3.91 Hz, 2H) 0.91-0.98 (m, 2H). MS (ESI) (m/z): 384.2 (M+H)⁺.

Example 116

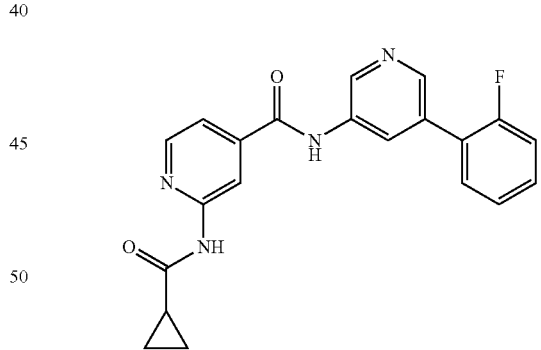

2-(cyclopropanecarboxamido)-N-(5-(2-fluorophenyl)pyridin-3-yl)isonicotinamide

¹H NMR (400 MHz, Chloroform-d) δ ppm 8.86 (d, J=2.45 Hz, 1H) 8.74 (s, 1H) 8.64 (t, J=1.71 Hz, 1H) 8.58 (s, 1H) 8.49 (dd, J=5.14, 0.73 Hz, 1H) 8.45 (s, 1H) 8.33 (s, 1H) 7.66 (dd, J=5.14, 1.71 Hz, 1H) 7.48-7.56 (m, 1H) 7.39-7.46 (m, 1H) 7.18-7.27 (m, 2H) 1.62-1.67 (m, 1H) 1.13-1.21 (m, 2H) 0.94-1.05 (m, 2H). ¹⁹F NMR (376 MHz, Chloroform-d) δ ppm −117.44 (s, 1F). MS (ESI) (m/z): 377.1 (M+H)⁺.

Example 117

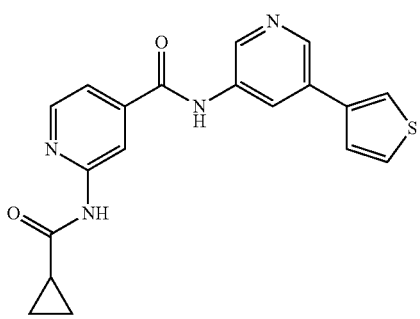 [SMILES: O=C(Nc1cncc(-c2ccsc2)c1)c1ccnc(NC(=O)C2CC2)c1]

2-(cyclopropanecarboxamido)-N-(5-(thiophen-3-yl)pyridin-3-yl)isonicotinamide $^1$H NMR (400 MHz, DMSO-d$_6$) δ ppm 11.04 (s, 1H) 10.76 (s, 1H) 8.85 (d, J=2.20 Hz, 1H) 8.75 (d, J=1.96 Hz, 1H) 8.57 (s, 1H) 8.53 (d, J=5.14 Hz, 1H) 8.44 (t, J=2.20 Hz, 1H) 8.01 (dd, J=2.93, 1.47 Hz, 1H) 7.74 (dd, J=5.14, 2.93 Hz, 1H) 7.59 (ddd, J=5.01, 3.55, 1.47 Hz, 2H) 2.00-2.11 (m, 1H) 0.80-0.90 (m, 4H). MS (ESI) (m/z): 365.1 (M+H)$^+$.

Example 121

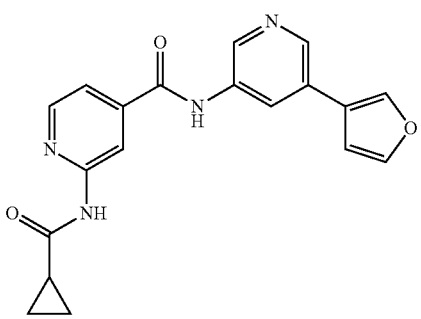

2-(cyclopropanecarboxamido)-N-(5-(furan-3-yl)pyridin-3-yl)isonicotinamide $^1$H NMR (500 MHz, DMSO-d$_6$) δ ppm 11.07 (s, 1H) 10.77 (br. s., 1H) 8.81 (d, J=2.44 Hz, 1H) 8.67 (d, J=1.83 Hz, 1H) 8.58 (s, 1H) 8.54 (d, J=5.19 Hz, 1H) 8.35 (t, J=1.98 Hz, 1H) 8.31 (s, 1H) 7.84 (t, J=1.68 Hz, 1H) 7.59 (dd, J=5.04, 1.37 Hz, 1H) 7.02 (d, J=1.22 Hz, 1H) 2.02-2.11 (m, 1H) 0.83-0.89 (m, 4H). MS (ESI) (m/z): 349.2 (M+H)$^+$.

Example 120

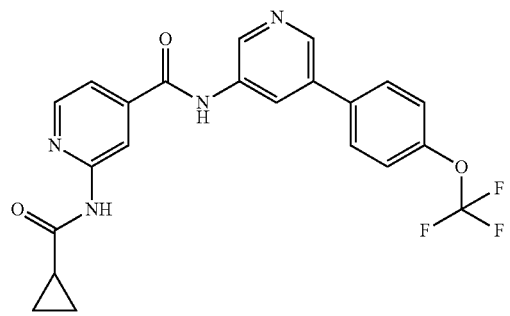 [SMILES: O=C(Nc1cncc(-c2ccc(OC(F)(F)F)cc2)c1)c1ccnc(NC(=O)C2CC2)c1]

2-(cyclopropanecarboxamido)-N-(5-(4-(trifluoromethoxy)phenyl)pyridin-3-yl)isonicotinamide $^1$H NMR (500 MHz, DMSO-d$_6$) δ ppm 11.08 (s, 1H) 10.85 (br. s., 1H) 8.96 (d, J=2.44 Hz, 1H) 8.70 (d, J=1.83 Hz, 1H) 8.58 (s, 1H) 8.55 (d, J=5.19 Hz, 1H) 8.48 (t, J=1.98 Hz, 1H) 7.87 (d, J=8.55 Hz, 2H) 7.60 (dd, J=5.19, 1.22 Hz, 1H) 7.55 (d, J=8.24 Hz, 2H) 2.02-2.10 (m, 1H) 0.83-0.89 (m, 4H). MS (ESI) (m/z): 443.2 (M+H)$^+$.

Example 122

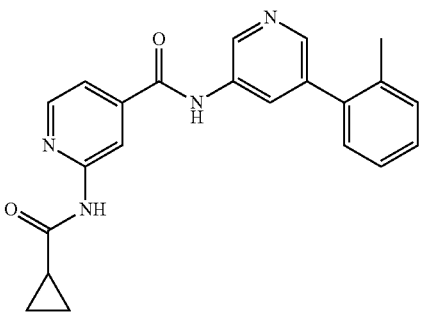 [SMILES: Cc1ccccc1-c1cncc(NC(=O)c2ccnc(NC(=O)C3CC3)c2)c1]

2-(cyclopropanecarboxamido)-N-(5-(o-tolyl)pyridin-3-yl)isonicotinamide $^1$H NMR (500 MHz, DMSO-d$_6$) δ ppm 11.09 (s, 1H) 11.02 (s, 1H) 9.07 (d, J=2.14 Hz, 1H) 8.58 (s, 1H) 8.55 (d, J=5.19 Hz, 1H) 8.48 (d, J=1.83 Hz, 1H) 8.34 (s, 1H) 7.62 (dd, J=5.19, 1.53 Hz, 1H) 7.30-7.42 (m, 4H) 2.31 (s, 3H) 2.06 (quin, J=6.26 Hz, 1H) 0.81-0.91 (m, 4H). MS (ESI) (m/z): 373.3 (M+H)$^+$.

Example 123

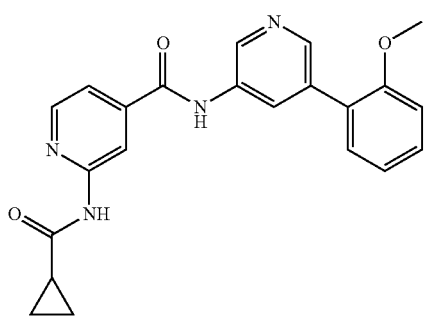 [SMILES: COc1ccccc1-c1cncc(NC(=O)c2ccnc(NC(=O)C3CC3)c2)c1]

2-(cyclopropanecarboxamido)-N-(5-(2-methoxyphenyl)pyridin-3-yl)isonicotinamide $^1$H NMR (500 MHz, DMSO-d$_6$) δ ppm 11.33 (s, 1H) 11.12 (s, 1H) 9.21 (d, J=2.14 Hz, 1H) 8.72-8.79 (m, 2H) 8.53-8.62 (m, 2H) 7.69 (dd, J=5.19, 1.53 Hz, 1H) 7.46-7.58 (m, 2H) 7.22-7.30 (m, 1H) 7.10-7.19 (m, 1H) 3.86 (s, 3H) 2.07 (quin, J=6.26 Hz, 1H) 0.85-0.89 (m, 4H). MS (ESI) (m/z): 389.3 (M+H)$^+$.

Example 124

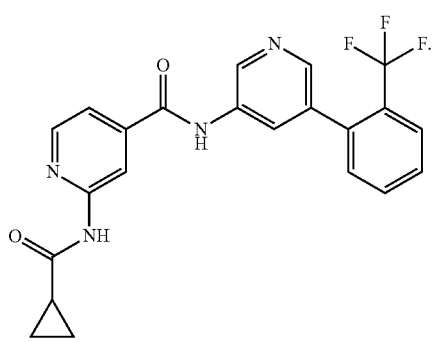 [SMILES: O=C(Nc1cncc(-c2ccccc2C(F)(F)F)c1)c1ccnc(NC(=O)C2CC2)c1]

2-(cyclopropanecarboxamido)-N-(5-(2-(trifluoromethyl)phenyl)pyridin-3-yl)isonicotinamide $^1$H NMR (500 MHz, DMSO-d$_6$) δ ppm 11.13 (d, J=11.29 Hz, 2H) 9.15 (d, J=2.44 Hz, 1H) 8.51-8.60 (m, 2H) 8.46 (d, J=1.22 Hz, 1H) 8.41 (s, 1H) 7.91-8.00 (m, 1H) 7.79-7.87 (m, 1H) 7.70-7.78 (m, 1H) 7.64 (dd, J=5.19, 1.53 Hz, 1H) 7.56 (d, J=7.32 Hz, 1H) 7.09-7.38 (m, 1H) 2.06 (quin, J=6.10 Hz, 1H) 0.80-0.91 (m, 4H). MS (ESI) (m/z): 427.3 (M+H)$^+$.

Example 125

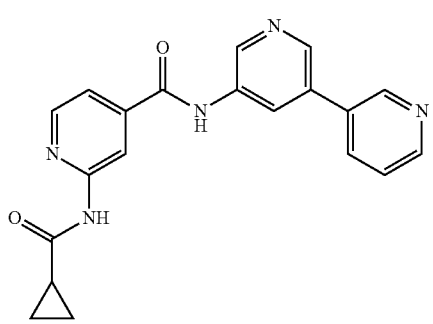 [SMILES: O=C(Nc1cncc(-c2cccnc2)c1)c1ccnc(NC(=O)C2CC2)c1]

N-([3,3'-bipyridin]-5-yl)-2-(cyclopropanecarboxamido)isonicotinamide $^1$H NMR (500 MHz, DMSO-d$_6$) δ ppm 11.08 (s, 1H) 10.87 (s, 1H) 8.99 (d, J=2.14 Hz, 1H) 8.95 (d, J=2.44 Hz, 1H) 8.74 (d, J=1.83 Hz, 1H) 8.67 (dd, J=4.73, 1.37 Hz, 1H) 8.59 (s, 1H) 8.55 (d, J=5.19 Hz, 1H) 8.50 (t, J=2.14 Hz, 1H) 8.16 (dt, J=7.86, 1.87 Hz, 1H) 7.54-7.62 (m, 2H) 2.02-2.11 (m, 1H) 0.84-0.89 (m, 4H). MS (ESI) (m/z): 360.2 (M+H)$^+$.

Example 126

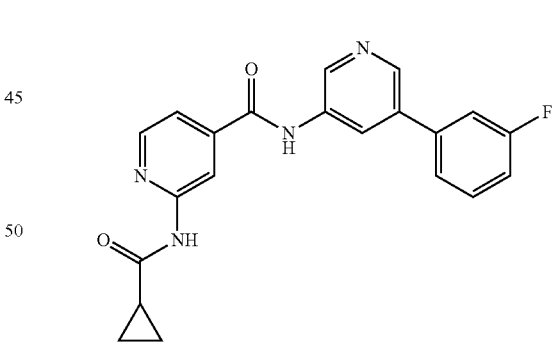

2-(cyclopropanecarboxamido)-N-(5-(3-fluorophenyl)pyridin-3-yl)isonicotinamide $^1$H NMR (500 MHz, DMSO-d$_6$) δ ppm 11.07 (s, 1H) 10.84 (br. s., 1H) 8.96 (d, J=2.14 Hz, 1H) 8.72 (d, J=1.83 Hz, 1H) 8.59 (s, 1H) 8.55 (d, J=4.88 Hz, 1H) 8.48 (t, J=2.14 Hz, 1H) 7.57-7.65 (m, 4H) 7.27-7.34 (m, 1H) 2.03-2.11 (m, 1H) 0.83-0.90 (m, 4H). MS (ESI) (m/z): 377.2 (M+H)$^+$.

Example 127

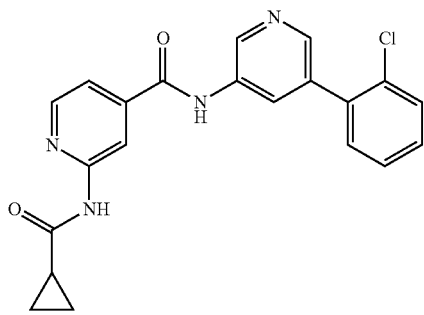 [SMILES: O=C(Nc1cncc(-c2ccccc2Cl)c1)c1ccnc(NC(=O)C2CC2)c1]

N-(5-(2-chlorophenyl)pyridin-3-yl)-2-(cyclopropan-ecarboxamido)isonicotinamide

¹H NMR (500 MHz, DMSO-d₆) δ ppm 11.07 (s, 1H) 10.86 (br. s., 1H) 8.99 (d, J=2.14 Hz, 1H) 8.57 (s, 1H) 8.54 (d, J=5.19 Hz, 1H) 8.42 (d, J=2.14 Hz, 1H) 8.30-8.33 (m, 1H) 7.63-7.68 (m, 1H) 7.59 (d, J=5.19 Hz, 1H) 7.48-7.55 (m, 3H) 2.03-2.10 (m, 1H) 0.83-0.88 (m, 4H). MS (ESI) (m/z): 393.2 (M+H)⁺.

Example 128

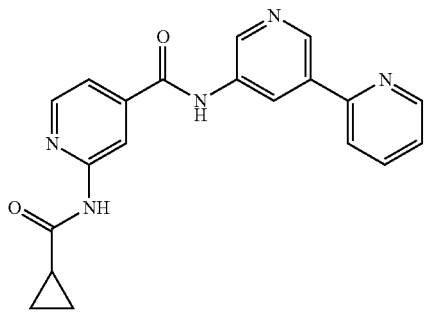 [SMILES: O=C(Nc1cncc(-c2ccccn2)c1)c1ccnc(NC(=O)C2CC2)c1]

N-([2,3'-bipyridin]-5'-yl)-2-(cyclopropanecarbox-amido)isonicotinamide

¹H NMR (500 MHz, DMSO-d₆) δ ppm 11.07 (br. s., 1H) 10.90 (br. s., 1H) 9.00-9.08 (m, 2H) 8.90 (s, 1H) 8.75 (d, J=3.97 Hz, 1H) 8.59 (s, 1H) 8.54 (d, J=5.19 Hz, 1H) 8.08 (d, J=7.93 Hz, 1H) 7.97 (t, J=7.78 Hz, 1H) 7.62 (d, J=4.88 Hz, 1H) 7.46 (dd, J=6.71, 5.49 Hz, 1H) 2.00-2.11 (m, 1H) 0.82-0.91 (m, 4H). MS (ESI) (m/z): 360.2 (M+H)⁺.

Example 129

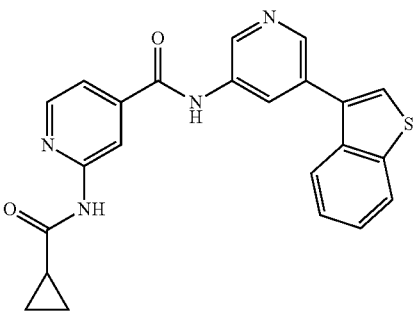 [SMILES: O=C(Nc1cncc(-c2csc3ccccc23)c1)c1ccnc(NC(=O)C2CC2)c1]

N-([2,3'-bipyridin]-5'-yl)-2-(cyclopropanecarbox-amido)isonicotinamide

¹H NMR (500 MHz, DMSO-d₆) δ ppm 11.08 (s, 1H) 10.88 (s, 1H) 9.02 (d, J=2.14 Hz, 1H) 8.63 (d, J=1.83 Hz, 1H) 8.59 (s, 1H) 8.55 (d, J=5.19 Hz, 1H) 8.49 (s, 1H) 8.15 (d, J=7.32 Hz, 1H) 8.07 (s, 1H) 7.99 (d, J=7.63 Hz, 1H) 7.61 (dd, J=5.04, 1.37 Hz, 1H) 7.47-7.56 (m, 2H) 2.02-2.10 (m, 1H) 0.82-0.90 (m, 4H). MS (ESI) (m/z): 415.2 (M+H)⁺.

Example 130

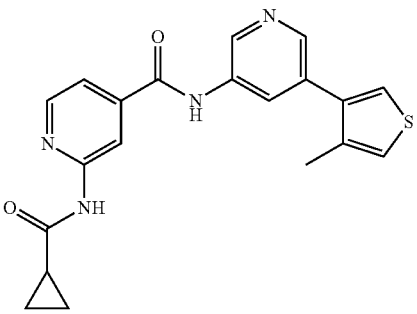 [SMILES: Cc1cscc1-c1cncc(NC(=O)c2ccnc(NC(=O)C3CC3)c2)c1]

2-(cyclopropanecarboxamido)-N-(5-(4-methylthio-phen-3-yl)pyridin-3-yl)isonicotinamide ¹H NMR (500 MHz, DMSO-d₆) δ ppm 11.07 (s, 1H) 10.80 (s, 1H) 8.92 (d, J=2.14 Hz, 1H) 8.56 (s, 1H) 8.52-8.55 (m, 1H) 8.45 (d, J=1.83 Hz, 1H) 8.27 (t, J=2.14 Hz, 1H) 7.68 (d, J=3.36 Hz, 1H) 7.58 (dd, J=5.19, 1.53 Hz, 1H) 7.38 (dd, J=3.20, 1.07 Hz, 1H) 2.30 (s, 3H) 2.02-2.09 (m, 1H) 0.83-0.89 (m, 4H). MS (ESI) (m/z): 379.2 (M+H)⁺.

Example 131

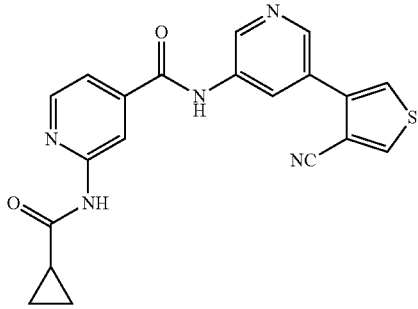 [SMILES: N#Cc1cscc1-c1cncc(NC(=O)c2ccnc(NC(=O)C3CC3)c2)c1]

N-(5-(4-cyanothiophen-3-yl)pyridin-3-yl)-2-(cyclopropanecarboxamido)isonicotinamide ¹H NMR (400 MHz, dimethylformamide) δ ppm 11.25 (br. s., 1H) 11.12 (s, 1H) 9.32 (d, J=2.45 Hz, 1H) 9.00 (d, J=2.93 Hz, 1H) 8.93 (s, 1H) 8.87 (d, J=1.96 Hz, 1H) 8.84 (t, J=2.08 Hz, 1H) 8.69 (d, J=5.14 Hz, 1H) 8.36 (d, J=3.18 Hz, 1H) 7.86 (dd, J=5.14, 1.47 Hz, 1H) 2.34-2.44 (m, 1H) 1.04-1.17 (m, 4H). MS (ESI) (m/z): 390.1 (M+H)⁺.

Example 133

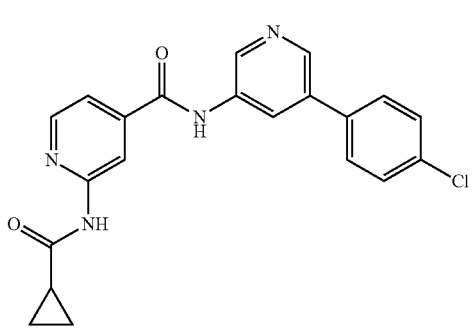 [SMILES: O=C(Nc1cncc(-c2ccc(Cl)cc2)c1)c1ccnc(NC(=O)C2CC2)c1]

N-(5-(4-chlorophenyl)pyridin-3-yl)-2-(cyclopropanecarboxamido)isonicotinamide

¹H NMR (500 MHz, DMSO-d₆) δ ppm 11.07 (s, 1H) 10.85 (br. s., 1H) 8.95 (d, J=2.44 Hz, 1H) 8.69 (d, J=2.14 Hz, 1H) 8.59 (s, 1H) 8.55 (d, J=5.19 Hz, 1H) 8.47 (t, J=2.29 Hz, 1H) 7.74-7.80 (m, 2H) 7.56-7.63 (m, 3H) 2.01-2.12 (m, 1H) 0.82-0.91 (m, 4H). MS (ESI) (m/z): 393.2 (M+H)⁺.

Example 134

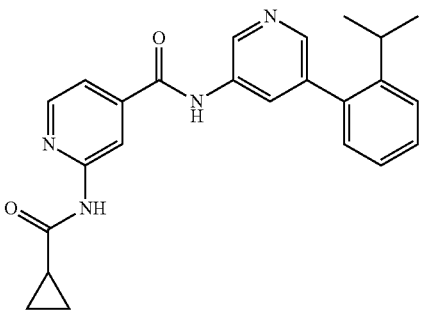

2-(cyclopropanecarboxamido)-N-(5-(2-isopropylphenyl)pyridin-3-yl)isonicotinamide ¹H NMR (500 MHz, DMSO-d₆) δ ppm 11.06 (s, 1H) 10.82 (s, 1H) 8.95 (d, J=2.14 Hz, 1H) 8.55 (s, 1H) 8.53 (d, J=5.19 Hz, 1H) 8.29 (d, J=2.14 Hz, 1H) 8.16 (t, J=1.98 Hz, 1H) 7.58 (dd, J=5.19, 1.53 Hz, 1H) 7.48-7.53 (m, 1H) 7.40-7.47 (m, 1H) 7.30 (td, J=7.40, 1.07 Hz, 1H) 7.21 (dd, J=7.63, 1.22 Hz, 1H) 2.97 (dt, J=13.73, 6.87 Hz, 1H) 2.02-2.10 (m, 1H) 1.17 (d, J=7.02 Hz, 6H) 0.83-0.89 (m, 4H). MS (ESI) (m/z): 401.3 (M+H)⁺.

Example 135

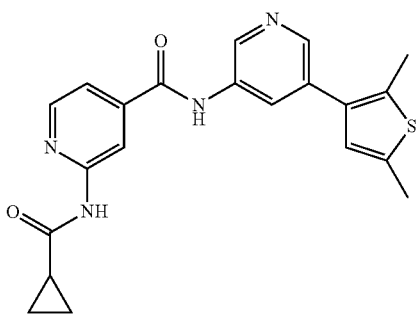 [SMILES: Cc1cc(-c2cncc(NC(=O)c3ccnc(NC(=O)C4CC4)c3)c2)c(C)s1]

2-(cyclopropanecarboxamido)-N-(5-(2,5-dimethylthiophen-3-yl)pyridin-3-yl)isonicotinamide ¹H NMR (500 MHz, DMSO-d₆) δ ppm 11.07 (s, 1H) 10.78 (s, 1H) 8.87 (d, J=2.44 Hz, 1H) 8.56 (s, 1H) 8.54 (d, J=5.19 Hz, 1H) 8.42 (d, J=1.83 Hz, 1H) 8.24 (t, J=1.98 Hz, 1H) 7.58 (dd, J=5.19, 1.53 Hz, 1H) 6.90 (s, 1H) 2.46 (s, 3H) 2.43 (s, 3H) 2.02-2.10 (m, 1H) 0.83-0.89 (m, 4H). MS (ESI) (m/z): 393.2 (M+H)⁺.

Example 136

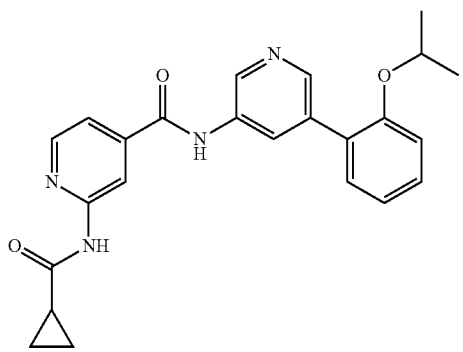 [SMILES: CC(C)Oc1ccccc1-c1cncc(NC(=O)c2ccnc(NC(=O)C3CC3)c2)c1]

2-(cyclopropanecarboxamido)-N-(5-(2-isopropoxy-phenyl)pyridin-3-yl)isonicotinamide $^1$H NMR (500 MHz, DMSO-d$_6$) δ ppm 11.08 (s, 1H) 10.91 (s, 1H) 8.94 (d, J=2.14 Hz, 1H) 8.48-8.62 (m, 4H) 7.59 (dd, J=5.19, 1.53 Hz, 1H) 7.36-7.49 (m, 2H) 7.21 (d, J=8.55 Hz, 1H) 7.05-7.14 (m, 1H) 4.69 (dt, J=11.98, 6.07 Hz, 1H) 2.06 (quin, J=6.18 Hz, 1H) 1.27 (d, J=6.10 Hz, 6H) 0.80-0.90 (m, 4H). MS (ESI) (m/z): 417.3 (M+H)$^+$.

Example 137

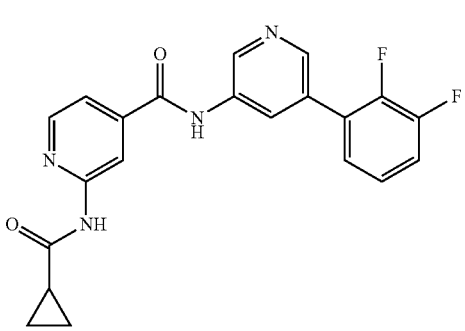 [SMILES: O=C(Nc1cncc(-c2cccc(F)c2F)c1)c1ccnc(NC(=O)C2CC2)c1]

2-(cyclopropanecarboxamido)-N-(5-(2,3-difluoro-phenyl)pyridin-3-yl)isonicotinamide $^1$H NMR (500 MHz, DMSO-d$_6$) δ ppm 11.07 (s, 1H) 10.88 (br. s., 1H) 9.01 (d, J=2.14 Hz, 1H) 8.58 (s, 2H) 8.54 (d, J=5.19 Hz, 1H) 8.44 (s, 1H) 7.59 (dd, J=4.88, 1.53 Hz, 1H) 7.36-7.58 (m, 3H) 2.02-2.10 (m, 1H) 0.83-0.90 (m, 4H). MS (ESI) (m/z): 395.2 (M+H)$^+$.

Example 138

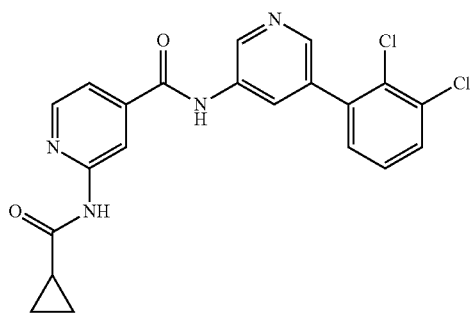 [SMILES: O=C(Nc1cncc(-c2cccc(Cl)c2Cl)c1)c1ccnc(NC(=O)C2CC2)c1]

2-(cyclopropanecarboxamido)-N-(5-(2,3-dichloro-phenyl)pyridin-3-yl)isonicotinamide $^1$H NMR (500 MHz, DMSO-d) δ ppm 11.07 (s, 1H) 10.88 (s, 1H) 9.00 (d, J=2.44 Hz, 1H) 8.56 (s, 1H) 8.54 (d, J=5.19 Hz, 1H) 8.43 (d, J=1.83 Hz, 1H) 8.31 (t, J=1.98 Hz, 1H) 7.77 (dd, J=7.32, 2.14 Hz, 1H) 7.58 (dd, J=5.04, 1.37 Hz, 1H) 7.48-7.55 (m, 2H) 2.02-2.09 (m, 1H) 0.84-0.88 (m, 4H). MS (ESI) (m/z): 427.1 (M+H)$^+$.

Example 139

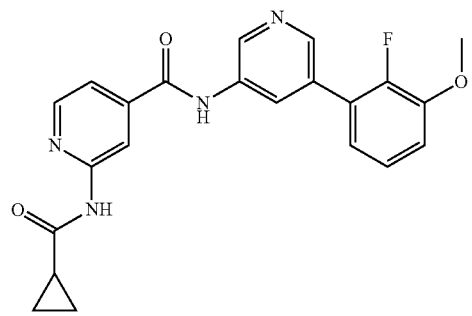 [SMILES: COc1cccc(-c2cncc(NC(=O)c3ccnc(NC(=O)C4CC4)c3)c2)c1F]

2-(cyclopropanecarboxamido)-N-(5-(2-fluoro-3-methoxyphenyl)pyridin-3-yl)isonicotinamide $^1$H NMR (500 MHz, DMSO-d$_6$) δ ppm 11.07 (s, 1H) 10.85 (br. s., 1H) 8.98 (d, J=2.44 Hz, 1H) 8.57 (s, 1H) 8.54 (d, J=5.19 Hz, 1H) 8.52 (s, 1H) 8.38 (s, 1H) 7.59 (dd, J=5.04, 1.37 Hz, 1H) 7.26-7.33 (m, 2H) 7.14 (td, J=6.64, 2.90 Hz, 1H) 3.92 (s, 3H) 2.02-2.11 (m, 1H) 0.82-0.90 (m, 4H); MS (ESI) (m/z): 407.2 (M+H)$^+$.

Example 140

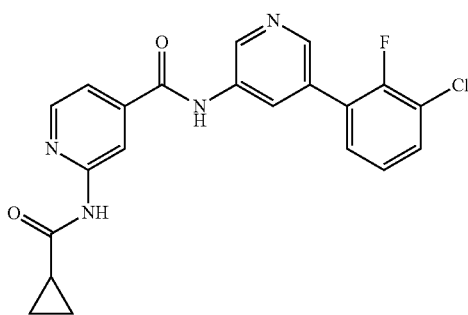

N-(5-(3-chloro-2-fluorophenyl)pyridin-3-yl)-2-(cyclopropanecarboxamido)isonicotinamide $^1$H NMR (500 MHz, DMSO-d$_6$) δ ppm 11.07 (s, 1H) 10.89 (br. s., 1H) 9.00 (d, J=2.44 Hz, 1H) 8.49-8.62 (m, 3H) 8.43 (s, 1H) 7.67-7.76 (m, 1H) 7.56-7.65 (m, 2H) 7.41 (t, J=7.93 Hz, 1H) 1.99-2.14 (m, 1H) 0.81-0.92 (m, 4H). MS (ESI) (m/z): 411.2 (M+H)$^+$.

Example 141

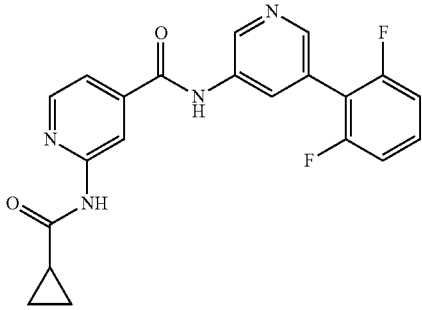 [SMILES: O=C(Nc1cncc(-c2c(F)cccc2F)c1)c1ccnc(NC(=O)C2CC2)c1]

2-(cyclopropanecarboxamido)-N-(5-(2,6-difluorophenyl)pyridin-3-yl)isonicotinamide $^1$H NMR (500 MHz, DMSO-d$_6$) δ ppm 11.07 (s, 1H) 10.88 (br. s., 1H) 9.00 (d, J=2.44 Hz, 1H) 8.57 (s, 1H) 8.54 (d, J=4.88 Hz, 1H) 8.46 (d, J=1.22 Hz, 1H) 8.34 (s, 1H) 7.56-7.61 (m, 2H) 7.32 (t, J=8.09 Hz, 2H) 2.02-2.10 (m, 1H) 0.83-0.89 (m, 4H). MS (ESI) (m/z): 395.2 (M+H)$^+$.

Example 142

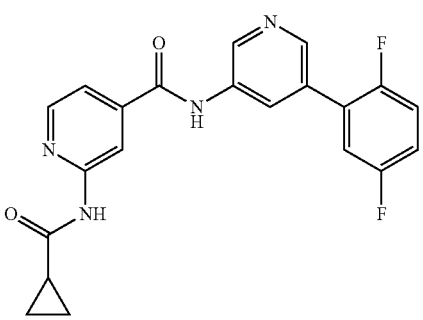 [SMILES: O=C(Nc1cncc(-c2cc(F)ccc2F)c1)c1ccnc(NC(=O)C2CC2)c1]

2-(cyclopropanecarboxamido)-N-(5-(2,5-difluorophenyl)pyridin-3-yl)isonicotinamide $^1$H NMR (500 MHz, DMSO-d$_6$) δ ppm 11.07 (s, 1H) 10.87 (br. s., 1H) 9.00 (d, J=2.14 Hz, 1H) 8.57 (s, 2H) 8.54 (d, J=4.88 Hz, 1H) 8.43 (d, J=1.53 Hz, 1H) 7.54-7.62 (m, 2H) 7.47 (td, J=9.54, 4.73 Hz, 1H) 7.34-7.41 (m, 1H) 2.02-2.11 (m, 1H) 0.83-0.90 (m, 4H). MS (ESI) (m/z): 395.2 (M+H)$^+$.

Example 143

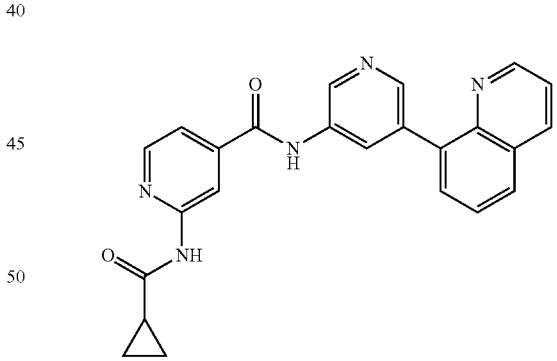

2-(cyclopropanecarboxamido)-N-(5-(quinolin-8-yl)pyridin-3-yl)isonicotinamide $^1$H NMR (500 MHz, DMSO-d$_6$) δ ppm 11.07 (s, 1H) 10.84 (s, 1H) 9.00 (d, J=2.44 Hz, 1H) 8.96 (dd, J=4.12, 1.68 Hz, 1H) 8.64 (d, J=1.83 Hz, 1H) 8.59 (s, 1H) 8.54 (d, J=5.19 Hz, 1H) 8.49 (td, J=4.12, 1.83 Hz, 2H) 8.10 (dd, J=8.09, 1.07 Hz, 1H) 7.89 (dd, J=7.02, 1.22 Hz, 1H) 7.72-7.78 (m, 1H) 7.59-7.65 (m, 2H) 2.03-2.11 (m, 1H) 0.83-0.89 (m, 4H). MS (ESI) (m/z): 410.2 (M+H)$^+$.

Example 144

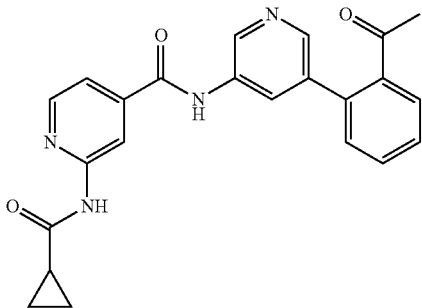 [SMILES: CC(=O)c1ccccc1-c1cncc(NC(=O)c2ccnc(NC(=O)C3CC3)c2)c1]

N-(5-(2-acetylphenyl)pyridin-3-yl)-2-(cyclopropanecarboxamido)isonicotinamide $^1$H NMR (500 MHz, DMSO-d$_6$) δ ppm 11.07 (s, 1H) 10.83 (br. s., 1H) 8.94 (d, J=2.44 Hz, 1H) 8.56 (s, 1H) 8.53 (d, J=5.19 Hz, 1H) 8.28 (d, J=2.14 Hz, 1H) 8.14 (t, J=2.14 Hz, 1H) 7.82 (dd, J=7.63, 1.22 Hz, 1H) 7.65-7.70 (m, 1H) 7.56-7.61 (m, 2H) 7.46-7.51 (m, 1H) 2.40 (s, 3H) 2.02-2.09 (m, 1H) 0.84-0.88 (m, 4H). MS (ESI) (m/z): 401.2 (M+H)$^+$.

Example 145

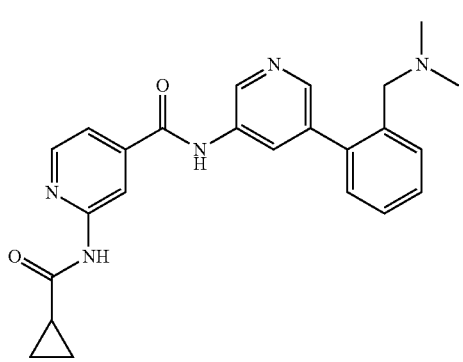

2-(cyclopropanecarboxamido)-N-(5-(2-((dimethylamino)methyl)phenyl)pyridin-3-yl)isonicotinamide $^1$H NMR (500 MHz, DMSO-d$_6$) ppm 11.06 (s, 1H) 10.80 (br. s., 1H) 8.93 (d, J=2.14 Hz, 1H) 8.56 (s, 1H) 8.53 (d, J=4.88 Hz, 1H) 8.40 (d, J=1.83 Hz, 1H) 8.22 (s, 1H) 7.58 (d, J=5.19 Hz, 1H) 7.54 (d, J=7.63 Hz, 1H) 7.38-7.47 (m, 2H) 7.31 (d, J=7.32 Hz, 1H) 2.08 (s, 6H) 2.05 (d, J=6.41 Hz, 1H) 1.90 (s, 2H) 0.79-0.92 (m, 4H). MS (ESI) (m/z): 416.2 (M+H)$^+$.

Example 146

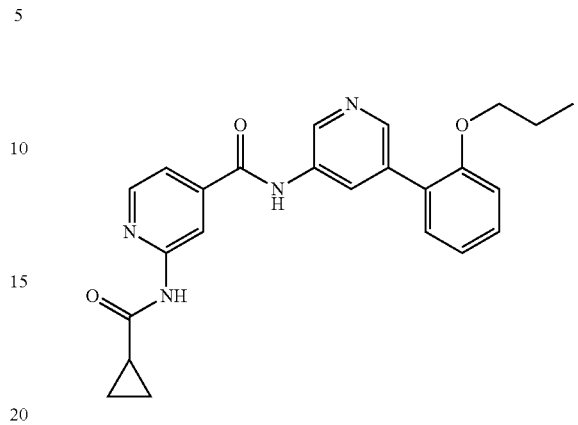

2-(cyclopropanecarboxamido)-N-(5-(2-propoxyphenyl)pyridin-3-yl)isonicotinamide $^1$H NMR (500 MHz, DMSO-d$_6$) δ ppm 11.06 (s, 1H) 10.76 (s, 1H) 8.86 (d, J=2.44 Hz, 1H) 8.56 (s, 1H) 8.53 (d, J=5.19 Hz, 1H) 8.50 (d, J=2.14 Hz, 1H) 8.37 (t, J=2.14 Hz, 1H) 7.57 (dd, J=5.19, 1.53 Hz, 1H) 7.37-7.44 (m, 2H) 7.17 (d, J=7.93 Hz, 1H) 7.06-7.11 (m, 1H) 4.00 (t, J=6.41 Hz, 2H) 2.02-2.10 (m, 1H) 1.65-1.75 (m, 2H) 0.92 (t, J=7.32 Hz, 3H) 0.83-0.88 (m, 4H). MS (ESI) (m/z): 417.3 (M+H)$^+$.

Example 147

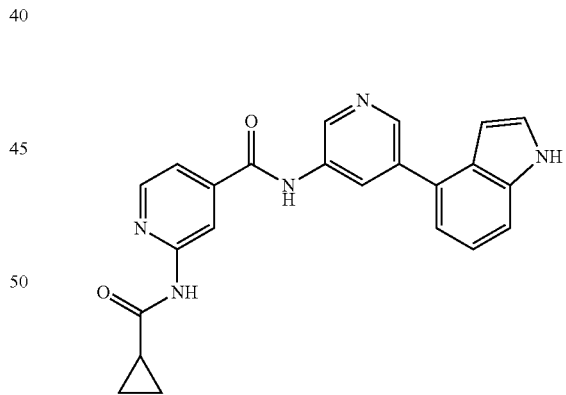

N-(5-(1H-indol-4-yl)pyridin-3-yl)-2-(cyclopropanecarboxamido)isonicotinamide $^1$H NMR (500 MHz, DMSO-d$_6$) δ ppm 11.39 (br. s., 1H) 11.07 (s, 1H) 10.84 (s, 1H) 8.95 (d, J=2.14 Hz, 1H) 8.65 (d, J=2.14 Hz, 1H) 8.59 (s, 1H) 8.57 (t, J=2.14 Hz, 1H) 8.55 (d, J=5.19 Hz, 1H) 7.62 (dd, J=5.19, 1.53 Hz, 1H) 7.46-7.54 (m, 2H) 7.16-7.31 (m, 2H) 6.69 (br. s., 1H) 2.01-2.12 (m, 1H) 0.82-0.91 (m, 4H). MS (ESI) (m/z): 398.3 (M+H)$^+$.

Example 148

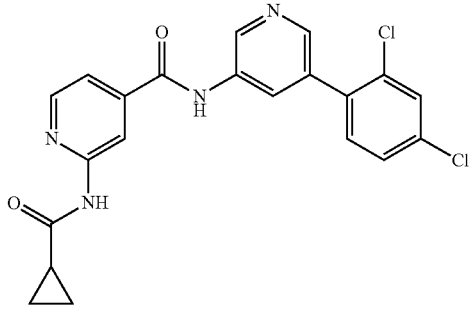

2-(cyclopropanecarboxamido)-N-(5-(2,4-dichloro-phenyl)pyridin-3-yl)isonicotinami $^1$H NMR (500 MHz, DMSO-d$_6$) δ ppm 11.07 (s, 1H) 10.88 (br. s., 1H) 8.99 (d, J=2.14 Hz, 1H) 8.56 (s, 1H) 8.54 (d, J=5.19 Hz, 1H) 8.42 (d, J=1.53 Hz, 1H) 8.31 (s, 1H) 7.84 (d, J=2.14 Hz, 1H) 7.54-7.63 (m, 3H) 2.00-2.11 (m, 1H) 0.82-0.91 (m, 4H). MS (ESI) (m/z): 427.3 (M+H)$^+$.

Example 149

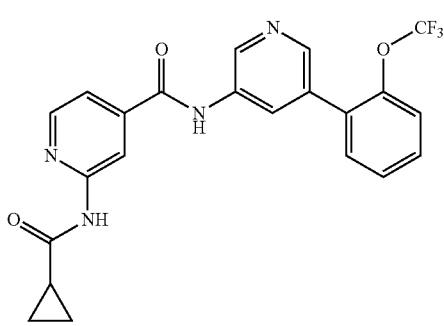 [SMILES: O=C(Nc1cncc(-c2ccccc2OC(F)(F)F)c1)c1ccnc(NC(=O)C2CC2)c1]

2-(cyclopropanecarboxamido)-N-(5-(2-(trifluo-romethoxy)phenyl)pyridin-3-yl)isonicotinamide $^1$H NMR (500 MHz, DMSO-d$_6$) δ ppm 11.07 (s, 1H) 10.87 (br. s., 1H) 8.98 (d, J=2.14 Hz, 1H) 8.57 (s, 1H) 8.54 (d, J=5.19 Hz, 1H) 8.46 (d, J=2.14 Hz, 1H) 8.36 (t, J=2.14 Hz, 1H) 7.55-7.67 (m, 5H) 2.03-2.10 (m, 1H) 0.84-0.89 (m, 4H). MS (ESI) (m/z): 443.3 (M+H)$^+$.

Example 151

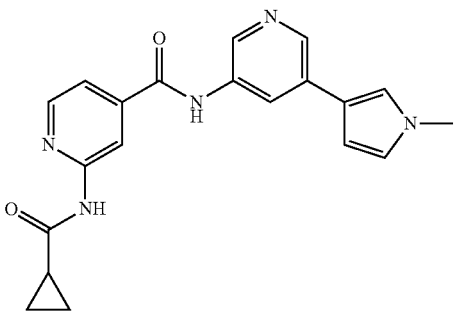 [SMILES: Cn1ccc(-c2cncc(NC(=O)c3ccnc(NC(=O)C4CC4)c3)c2)c1]

2-(cyclopropanecarboxamido)-N-(5-(1-methyl-1H-pyrrol-3-yl)pyridin-3-yl)isonicotinamide $^1$H NMR (500 MHz, DMSO-d$_6$) δ ppm 11.07 (s, 1H) 10.78 (s, 1H) 8.86 (d, J=2.14 Hz, 1H) 8.57 (s, 1H) 8.54 (d, J=5.19 Hz, 1H) 8.47 (d, J=1.83 Hz, 1H) 8.25 (t, J=2.14 Hz, 1H) 7.59 (dd, J=5.04, 1.37 Hz, 1H) 6.95 (t, J=2.14 Hz, 1H) 6.33 (dd, J=3.51, 1.68 Hz, 1H) 6.11-6.16 (m, 1H) 3.73 (s, 3H) 2.02-2.10 (m, 1H) 0.83-0.89 (m, 4H). MS (ESI) (m/z): 362.2 (M+H)$^+$.

Example 152

2-(cyclopropanecarboxamido)-N-(5-(1-methyl-1H-pyrazol-4-yl)pyridin-3-yl)isonicotinamid $^1$H NMR (500 MHz, DMSO-d$_6$) δ ppm 11.06 (s, 1H) 10.73 (s, 1H) 8.73 (d, J=2.14 Hz, 1H) 8.62 (d, J=1.83 Hz, 1H) 8.57 (s, 1H) 8.54 (d, J=5.19 Hz, 1H) 8.32 (t, J=2.14 Hz, 1H) 8.26 (s, 1H) 7.93 (s, 1H) 7.59 (dd, J=5.04, 1.37 Hz, 1H) 3.91 (s, 3H) 2.03-2.10 (m, 1H) 0.85-0.90 (m, 4H). MS (ESI) (m/z): 363.2 (M+H)$^+$.

Example 153

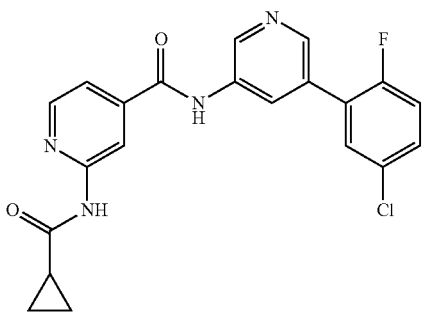 [SMILES: O=C(Nc1cncc(-c2cc(Cl)ccc2F)c1)c1ccnc(NC(=O)C2CC2)c1]

N-(5-(5-chloro-2-fluorophenyl)pyridin-3-yl)-2-(cyclopropanecarboxamido)isonicotinamide ¹H NMR (500 MHz, DMSO-d₆) δ ppm 11.07 (s, 1H) 10.86 (br. s., 1H) 9.00 (d, J=2.44 Hz, 1H) 8.57 (d, J=2.14 Hz, 2H) 8.54 (d, J=5.19 Hz, 1H) 8.41 (d, J=1.53 Hz, 1H) 7.74 (dd, J=6.56, 2.59 Hz, 1H) 7.56-7.63 (m, 2H) 7.48 (dd, J=10.22, 9.00 Hz, 1H) 2.02-2.11 (m, 1H) 0.82-0.92 (m, 4H). MS (ESI) (m/z): 411.3 (M+H)⁺.

Example 154

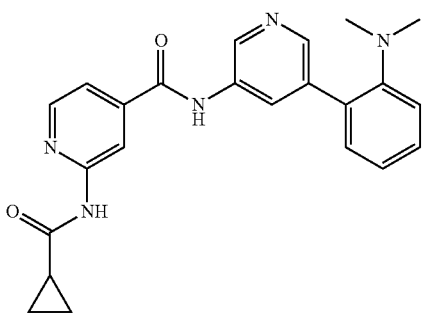

2-(cyclopropanecarboxamido)-N-(5-(2-(dimethylamino)phenyl)pyridin-3-yl)isonicotinamide ¹H NMR (500 MHz, DMSO-d₆) δ ppm 11.06 (s, 1H) 10.77 (s, 1H) 8.90 (d, J=2.14 Hz, 1H) 8.48-8.59 (m, 3H) 8.34 (s, 1H) 7.49-7.63 (m, 1H) 7.31-7.39 (m, 1H) 7.21-7.28 (m, 1H) 7.16 (d, J=8.24 Hz, 1H) 7.03-7.12 (m, 1H) 3.35 (s, 33H) 2.47-2.56 (m, 6H) 2.06 (quin, J=6.10 Hz, 1H) 0.78-0.92 (m, 4H). MS (ESI) (m/z): 402.3 (M+H)⁺.

Example 155

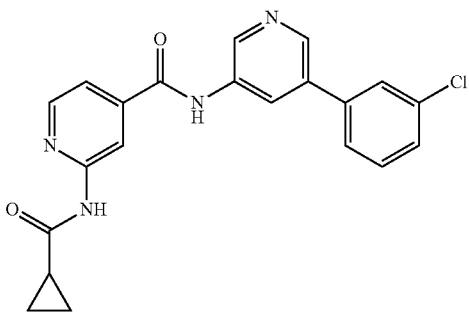

N-(5-(3-chlorophenyl)pyridin-3-yl)-2-(cyclopropanecarboxamido)isonicotinamide

¹H NMR (500 MHz, DMSO-d₆) δ ppm 11.07 (s, 1H) 10.82 (br. s., 1H) 8.98 (d, J=2.14 Hz, 1H) 8.72 (d, J=2.14 Hz, 1H) 8.59 (s, 1H) 8.55 (d, J=4.88 Hz, 1H) 8.47 (t, J=2.14 Hz, 1H) 7.81 (t, J=1.83 Hz, 1H) 7.72 (d, J=7.63 Hz, 1H) 7.50-7.62 (m, 3H) 2.03-2.10 (m, 1H) 0.83-0.89 (m, 4H). MS (ESI) (m/z): 393.2 (M+H)⁺.

Example 156

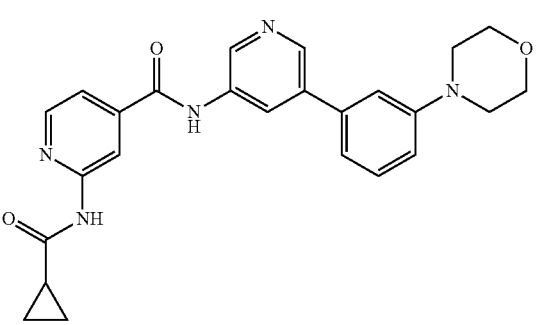 [SMILES: O=C(Nc1cncc(-c2cccc(N3CCOCC3)c2)c1)c1ccnc(NC(=O)C2CC2)c1]

2-(cyclopropanecarboxamido)-N-(5-(3-morpholinophenyl)pyridin-3-yl)isonicotinamide ¹H NMR (500 MHz, DMSO-d₆) δ ppm 11.06 (s, 1H) 10.79 (br. s., 1H) 8.94 (d, J=2.14 Hz, 1H) 8.67 (d, J=1.83 Hz, 1H) 8.58 (s, 1H) 8.54 (d, J=5.19 Hz, 1H) 8.38-8.43 (m, 1H) 7.60 (dd, J=5.04, 1.37 Hz, 1H) 7.39 (t, J=7.93 Hz, 1H) 7.22 (s, 1H) 7.13 (d, J=7.32 Hz, 1H) 7.04 (dd, J=8.24, 2.14 Hz, 1H) 3.73-3.81 (m, 4H) 3.17-3.25 (m, 4H) 2.01-2.12 (m, 1H) 0.81-0.91 (m, 4H). MS (ESI) (m/z): 444.4 (M+H)⁺.

Example 157

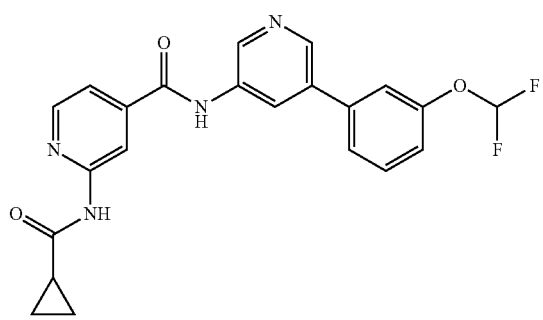 [SMILES: O=C(Nc1cncc(-c2cccc(OC(F)F)c2)c1)c1ccnc(NC(=O)C2CC2)c1]

2-(cyclopropanecarboxamido)-N-(5-(3-(difluoromethoxy)phenyl)pyridin-3-yl)isonicotinamide $^1$H NMR (500 MHz, DMSO-d$_6$) δ ppm 11.07 (s, 1H) 10.86 (br. s., 1H) 8.98 (d, J=2.14 Hz, 1H) 8.71 (d, J=2.14 Hz, 1H) 8.59 (s, 1H) 8.55 (d, J=4.88 Hz, 1H) 8.47 (t, J=1.98 Hz, 1H) 7.58-7.64 (m, 3H) 7.53 (s, 1H) 7.22-7.40 (m, 2H) 2.03-2.12 (m, 1H) 0.83-0.92 (m, 4H). MS(ESI) (m/z): 425.3 (M+H)$^+$.

Example 158

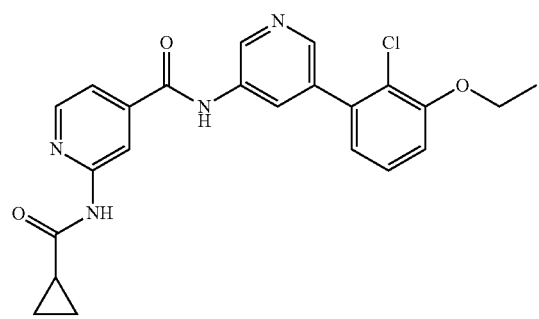 [SMILES: CCOc1cccc(-c2cncc(NC(=O)c3ccnc(NC(=O)C4CC4)c3)c2)c1Cl]

N-(5-(2-chloro-3-ethoxyphenyl)pyridin-3-yl)-2-(cyclopropanecarboxamido)isonicotinamide $^1$H NMR (500 MHz, DMSO-d$_6$) δ ppm 11.06 (s, 1H) 10.87 (br. s., 1H) 8.97 (d, J=2.44 Hz, 1H) 8.56 (s, 1H) 8.53 (d, J=5.19 Hz, 1H) 8.38 (d, J=1.83 Hz, 1H) 8.24-8.30 (m, 1H) 7.59 (dd, J=5.19, 1.22 Hz, 1H) 7.38-7.46 (m, 1H) 7.25 (d, J=7.63 Hz, 1H) 7.02-7.08 (m, 1H) 4.20 (q, J=7.02 Hz, 2H) 2.01-2.10 (m, 1H) 1.41 (t, J=7.02 Hz, 3H) 0.79-0.90 (m, 4H). MS (ESI) (m/z): 437.2 (M+H)$^+$.

Example 159

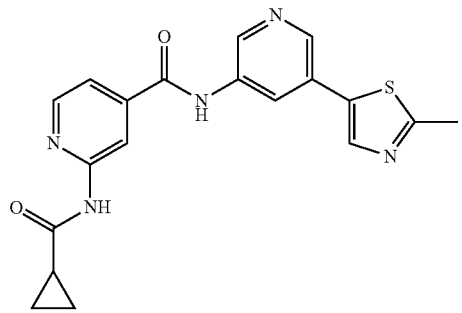 [SMILES: Cc1ncc(-c2cncc(NC(=O)c3ccnc(NC(=O)C4CC4)c3)c2)s1]

2-(cyclopropanecarboxamido)-N-(5-(2-methylthiazol-5-yl)pyridin-3-yl)isonicotinamide $^1$H NMR (500 MHz, DMSO-d$_6$) δ ppm 11.07 (s, 1H) 10.88 (br. s., 1H) 8.90 (d, J=2.44 Hz, 1H) 8.69 (d, J=1.83 Hz, 1H) 8.57 (s, 1H) 8.54 (d, J=4.88 Hz, 1H) 8.39 (t, J=2.14 Hz, 1H) 8.16 (s, 1H) 7.60 (dd, J=5.19, 1.53 Hz, 1H) 2.73 (s, 3H) 2.02-2.11 (m, 1H) 0.82-0.90 (m, 4H). MS (ESI) (m/z): 380.2 (M+H)$^+$.

Example 160

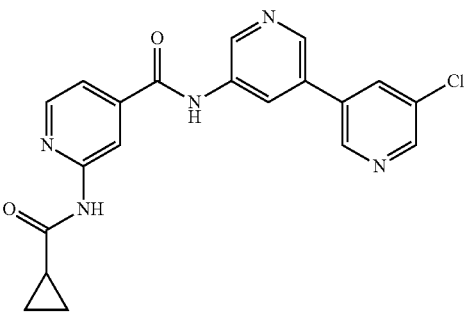

N-(5-(2-chloro-3-ethoxyphenyl)pyridin-3-yl)-2-(cyclopropanecarboxamido)isonicotinamide $^1$H NMR (500 MHz, DMSO-d$_6$) δ ppm 11.07 (s, 1H) 10.89 (br. s., 1H) 9.00 (d, J=2.44 Hz, 1H) 8.92 (d, J=1.83 Hz, 1H) 8.78 (d, J=2.14 Hz, 1H) 8.73 (d, J=2.44 Hz, 1H) 8.55 (d, J=5.19 Hz, 1H) 8.53 (t, J=2.14 Hz, 1H) 8.34 (t, J=2.14 Hz, 1H) 7.97 (s, 1H) 7.60 (dd, J=5.04, 1.37 Hz, 1H) 2.02-2.11 (m, 1H) 0.83-0.91 (m, 4H). MS (ESI) (m/z): 394.2 (M+H)$^+$.

Example 161

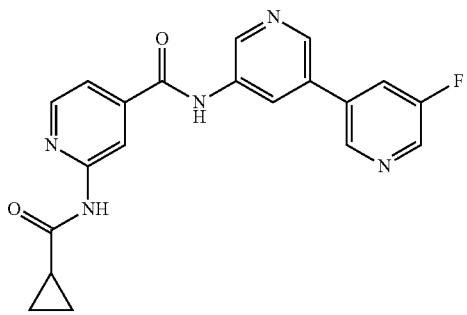

2-(cyclopropanecarboxamido)-N-(5'-fluoro-[3,3'-bipyridin]-5-yl)isonicotinamide $^1$H NMR (500 MHz, DMSO-d$_6$) δ ppm 11.07 (s, 1H) 10.88 (br. s., 1H) 9.00 (d, J=2.14 Hz, 1H) 8.82-8.87 (m, 1H) 8.78 (d, J=2.14 Hz, 1H) 8.69 (d, J=2.44 Hz, 1H) 8.59 (s, 1H) 8.55 (d, J=4.88 Hz, 1H) 8.53 (t, J=2.14 Hz, 1H) 8.18 (dt, J=10.07, 2.29 Hz, 1H) 7.60 (dd, J=5.19, 1.53 Hz, 1H) 2.04-2.10 (m, 1H) 0.85-0.89 (m, 4H). MS (ESI) (m/z): 378.2 (M+H)$^+$.

Example 162

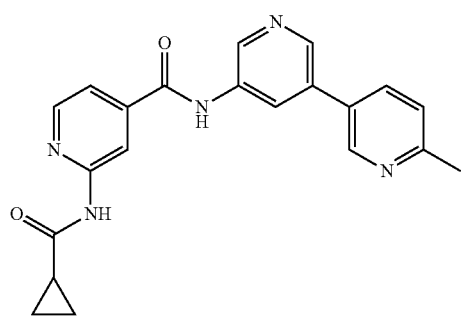 [SMILES: Cc1ccc(-c2cncc(NC(=O)c3ccnc(NC(=O)C4CC4)c3)c2)cn1]

2-(cyclopropanecarboxamido)-N-(6'-methyl-[3,3'-bipyridin]-5-yl)isonicotinamide $^1$H NMR (500 MHz, DMSO-d$_6$) δ ppm 11.07 (s, 1H) 10.85 (br. s., 1H) 8.97 (d, J=2.44 Hz, 1H) 8.81 (d, J=2.44 Hz, 1H) 8.71 (d, J=2.14 Hz, 1H) 8.59 (s, 1H) 8.55 (d, J=4.88 Hz, 1H) 8.47 (t, J=2.14 Hz, 1H) 8.04 (dd, J=7.93, 2.44 Hz, 1H) 7.60 (dd, J=5.19, 1.53 Hz, 1H) 7.43 (d, J=7.93 Hz, 1H) 2.55 (s, 3H) 2.02-2.12 (m, 1H) 0.82-0.90 (m, 4H). MS (ESI) (m/z): 374.2 (M+H)$^+$.

Example 163

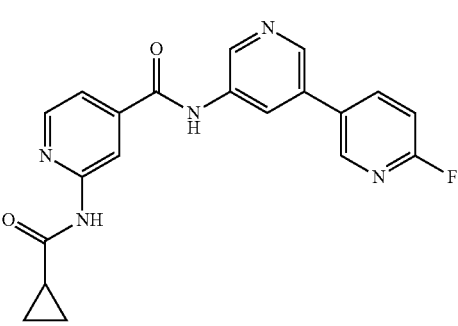 [SMILES: O=C(Nc1cncc(-c2ccc(F)nc2)c1)c1ccnc(NC(=O)C2CC2)c1]

2-(cyclopropanecarboxamido)-N-(6'-fluoro-[3,3'-bipyridin]-5-yl)isonicotinamide $^1$H NMR (500 MHz, DMSO-d$_6$) δ ppm 11.07 (s, 1H) 10.87 (br. s., 1H) 8.98 (d, J=2.14 Hz, 1H) 8.73 (d, J=1.83 Hz, 1H) 8.62 (d, J=2.44 Hz, 1H) 8.59 (s, 1H) 8.55 (d, J=5.19 Hz, 1H) 8.49 (t, J=2.14 Hz, 1H) 8.36 (td, J=8.16, 2.59 Hz, 1H) 7.60 (dd, J=5.04, 1.37 Hz, 1H) 7.38 (dd, J=8.55, 2.75 Hz, 1H) 2.01-2.11 (m, 1H) 0.83-0.90 (m, 4H). MS (ESI) (m/z): 378.3 (M+H)$^+$.

Example 164

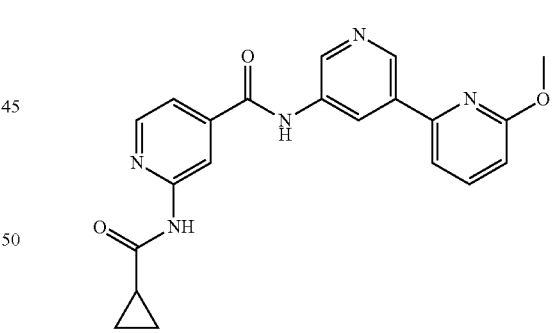

2-(cyclopropanecarboxamido)-N-(6-methoxy-[2,3'-bipyridin]-5'-yl)isonicotinamide $^1$H NMR (500 MHz, DMSO-d$_6$) δ ppm 11.07 (s, 1H) 10.86 (br. s., 1H) 9.05 (d, J=1.83 Hz, 1H) 9.01 (d, J=2.44 Hz, 1H) 8.86 (s, 1H) 8.58 (s, 1H) 8.54 (d, J=4.88 Hz, 1H) 7.87 (t, J=7.93 Hz, 1H) 7.66 (d, J=7.63 Hz, 1H) 7.61 (d, J=4.88 Hz, 1H) 6.89 (d, J=8.24 Hz, 1H) 4.00 (s, 3H) 2.04-2.12 (m, 1H) 0.84-0.90 (m, 4H). MS (ESI) (m/z): 390.3 (M+H)$^+$.

Example 165

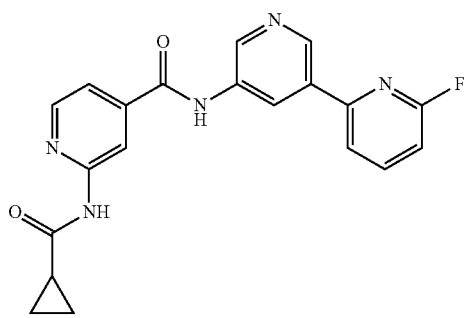

2-(cyclopropanecarboxamido)-N-(6-fluoro-[2,3'-bipyridin]-5'-yl)isonicotinamide $^{1}$H NMR (500 MHz, DMSO-$d_6$) δ ppm 11.07 (s, 1H) 10.90 (br. s., 1H) 9.06 (dd, J=16.33, 2.29 Hz, 2H) 8.84 (t, J=2.14 Hz, 1H) 8.60 (s, 1H) 8.54 (d, J=5.19 Hz, 1H) 8.17 (q, J=8.04 Hz, 1H) 8.06 (dd, J=7.48, 2.29 Hz, 1H) 7.62 (dd, J=5.19, 1.22 Hz, 1H) 7.26 (dd, J=8.09, 2.59 Hz, 1H) 2.01-2.13 (m, 1H) 0.81-0.93 (m, 4H). MS (ESI) (m/z): 378.3 (M+H)$^{+}$.

Example 166

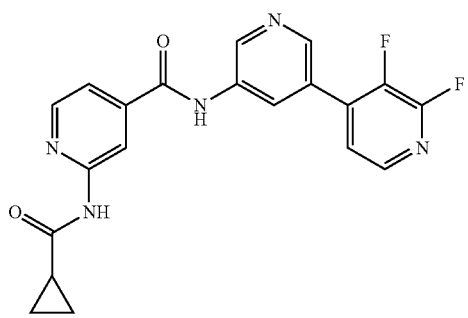

2-(cyclopropanecarboxamido)-N-(2',3'-difluoro-[3,4'-bipyridin]-5-yl)isonicotinamide $^{1}$H NMR (500 MHz, DMSO-$d_6$) δ ppm 11.08 (s, 1H) 9.07 (d, J=2.14 Hz, 1H) 8.69 (s, 1H) 8.52-8.60 (m, 3H) 8.20 (d, J=4.88 Hz, 1H) 7.71 (t, J=5.04 Hz, 1H) 7.60 (d, J=6.71 Hz, 1H) 2.06 (t, J=6.41 Hz, 1H) 0.84-0.89 (m, 4H). MS (ESI) (m/z): 396.2 (M+H)$^{+}$.

Example 174

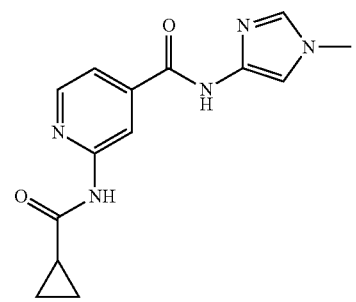 [SMILES: Cn1cnc(NC(=O)c2ccnc(NC(=O)C3CC3)c2)c1]

2-(cyclopropanecarboxamido)-N-(1-methyl-1H-imidazol-4-yl)isonicotinamide $^{1}$H NMR (500 MHz, Chloroform-d) δ ppm 8.61 (s, 1H) 8.49 (br. s., 1H) 8.43 (d, J=5.19 Hz, 1H) 8.18 (br. s., 1H) 7.54 (dd, J=5.04, 1.68 Hz, 1H) 7.46 (d, J=1.53 Hz, 1H) 7.24 (s, 1H) 3.71 (s, 3H) 1.58-1.61 (m, 1H) 1.12-1.18 (m, 2H) 0.92-1.00 (m, 2H); MS (ESI) (m/z): 286.1 (M+H)$^{+}$.

Example 176

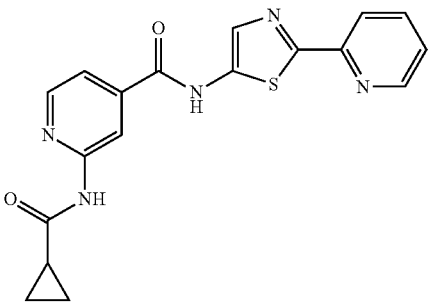 [SMILES: O=C(Nc1cnc(-c2ccccn2)s1)c1ccnc(NC(=O)C2CC2)c1]

2-(cyclopropanecarboxamido)-N-(2-(pyridin-2-yl)thiazol-5-yl)isonicotinamide $^{1}$H NMR (400 MHz, DMSO-$d_6$) δ ppm 12.16 (br. s., 1H) 11.02 (s, 1H) 9.12 (dd, J=2.26, 0.75 Hz, 1H) 8.60-8.64 (m, 2H) 8.54 (dd, J=5.14, 0.63 Hz, 1H) 8.25-8.30 (m, 1H) 7.97 (s, 1H) 7.89 (s, 1H) 7.62-7.65 (m, 1H) 7.52 (ddd, J=7.97, 4.83, 0.75 Hz, 1H) 2.03-2.11 (m, 1H) 0.84-0.91 (m, 4H). MS (ESI) (m/z): 366.0 (M+H)$^{+}$.

Example 181

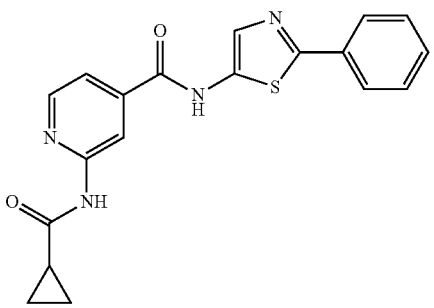 [SMILES: O=C(Nc1cnc(-c2ccccc2)s1)c1ccnc(NC(=O)C2CC2)c1]

2-(cyclopropanecarboxamido)-N-(2-phenylthiazol-5-yl)isonicotinamide $^1$H NMR (400 MHz, DMSO-d$_6$) δ ppm 12.04 (br. s., 1H) 11.03 (s, 1H) 8.62 (dd, J=1.51, 0.75 Hz, 1H) 8.54 (dd, J=5.14, 0.63 Hz, 1H) 7.90-7.99 (m, 2H) 7.84 (s, 1H) 7.60-7.65 (m, 1H) 7.41-7.54 (m, 3H) 2.03-2.12 (m, 1H) 0.84-0.91 (m, 4H). MS (ESI) (m/z): 365.0 (M+H)$^+$.

Example 182

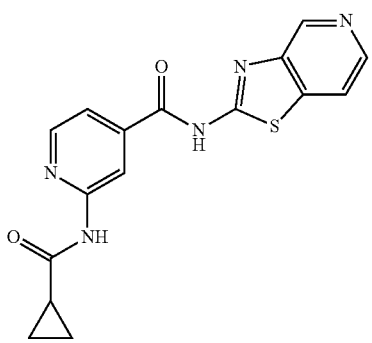 [SMILES: O=C(Nc1nc2cnccc2s1)c1ccnc(NC(=O)C2CC2)c1]

2-(cyclopropanecarboxamido)-N-(thiazolo[4,5-c]pyridin-2-yl)isonicotinamide $^1$H NMR (500 MHz, DMSO-d$_6$) δ ppm 11.05 (s, 1H) 9.04 (s, 1H) 8.69 (s, 1H) 8.53 (d, J=5.19 Hz, 1H) 8.42 (d, J=5.19 Hz, 1H) 8.09 (d, J=5.19 Hz, 1H) 7.97 (s, 1H) 7.74 (dd, J=5.19, 1.53 Hz, 1H) 2.01-2.10 (m, 1H) 0.77-0.92 (m, 4H). MS (ESI) (m/z): 340.1 (M+H)$^+$.

Example 183

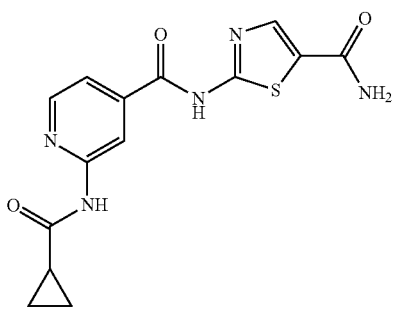 [SMILES: NC(=O)c1cnc(NC(=O)c2ccnc(NC(=O)C3CC3)c2)s1]

2-(2-(cyclopropanecarboxamido)isonicotinamido)thiazole-5-carboxamide $^1$H NMR (500 MHz, DMSO-d$_6$) δ ppm 10.96 (s, 1H) 8.65 (s, 1H) 8.46 (d, J=5.19 Hz, 1H) 8.09 (s, 1H) 7.97 (s, 1H) 7.85 (br. s., 1H) 7.68 (dd, J=5.04, 1.37 Hz, 1H) 7.30 (br. s., 1H) 1.99-2.11 (m, 1H) 0.80-0.95 (m, 4H). MS (ESI) (m/z): 332.1 (M+H)$^+$.

Example 184

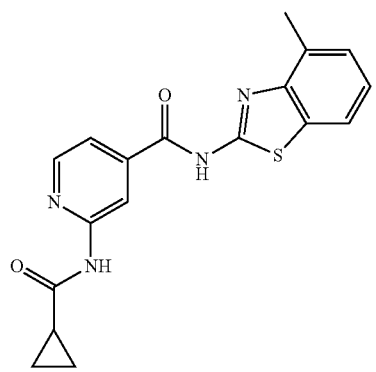 [SMILES: Cc1cccc2sc(NC(=O)c3ccnc(NC(=O)C4CC4)c3)nc12]

2-(cyclopropanecarboxamido)-N-(4-methylbenzo[d]thiazol-2-yl)isonicotinamide $^1$H NMR (500 MHz, DMSO-d$_6$) δ ppm 11.03 (br. s., 1H) 8.69 (s, 1H) 8.51 (d, J=4.88 Hz, 1H) 7.97 (s, 1H) 7.82 (d, J=7.32 Hz, 1H) 7.74 (dd, J=5.19, 1.53 Hz, 1H) 7.21-7.31 (m, 2H) 2.63 (s, 3H) 2.01-2.12 (m, 1H) 0.82-0.92 (m, 4H). MS (ESI) (m/z): 353.1 (M+H)$^+$.

Example 192

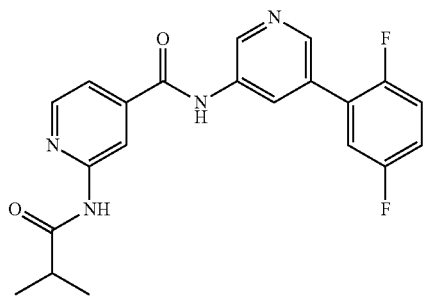 [SMILES: CC(C)C(=O)Nc1cc(C(=O)Nc2cncc(-c3cc(F)ccc3F)c2)ccn1]

N-(5-(2,5-difluorophenyl)pyridin-3-yl)-2-isobutyramidoisonicotinamide $^1$H NMR (500 MHz, DMSO-d$_6$) δ ppm 10.90 (br. s., 1H) 10.70 (s, 1H) 9.01 (d, J=2.44 Hz, 1H) 8.61 (s, 1H) 8.57 (s, 1H) 8.54 (d, J=5.19 Hz, 1H) 8.44 (d, J=1.53 Hz, 1H) 7.60 (dd, J=5.19, 1.53 Hz, 2H) 7.48 (td, J=9.61, 4.58 Hz, 1H) 7.35-7.41 (m, 1H) 2.81 (quin, J=6.87 Hz, 1H) 1.13 (d, J=6.71 Hz, 6H). MS (ESI) (m/z): 397.2 (M+H)$^+$.

Example 193

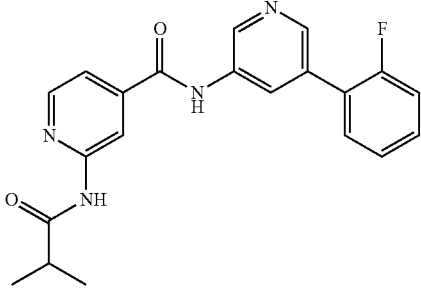 [SMILES: CC(C)C(=O)Nc1cc(C(=O)Nc2cncc(-c3ccccc3F)c2)ccn1]

N-(5-(2-fluorophenyl)pyridin-3-yl)-2-isobutyramidoisonicotinamide $^1$H NMR (500 MHz, DMSO-d$_6$) δ ppm 10.87 (br. s., 1H) 10.70 (s, 1H) 8.99 (d, J=2.14 Hz, 1H) 8.61 (s, 1H) 8.51-8.58 (m, 2H) 8.42 (d, J=1.53 Hz, 1H) 7.65 (td, J=7.78, 1.53 Hz, 1H) 7.60 (dd, J=5.19, 1.53 Hz, 1H) 7.49-7.56 (m, 1H) 7.34-7.45 (m, 2H) 2.81 (quin, J=6.79 Hz, 1H) 1.13 (d, J=6.71 Hz, 6H). MS (ESI) (m/z): 379.1 (M+H)$^+$.

Example-194

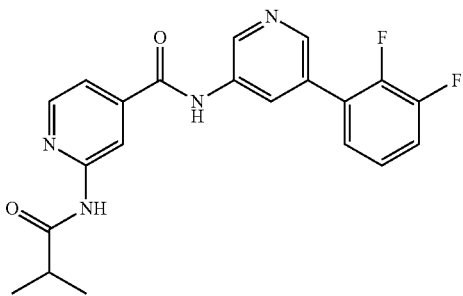 [SMILES: CC(C)C(=O)Nc1cc(C(=O)Nc2cncc(-c3cccc(F)c3F)c2)ccn1]

N-(5-(2,3-difluorophenyl)pyridin-3-yl)-2-isobutyramidoisonicotinamide $^1$H NMR (500 MHz, DMSO-d) δ ppm 10.91 (br. s., 1H) 10.70 (s, 1H) 9.02 (d, J=2.14 Hz, 1H) 8.61 (s, 1H) 8.58 (s, 1H) 8.54 (d, J=4.88 Hz, 1H) 8.45 (d, J=1.22 Hz, 1H) 7.60 (dd, J=5.19, 1.53 Hz, 1H) 7.53-7.59 (m, 1H) 7.45-7.49 (m, 1H) 7.36-7.43 (m, 1H) 2.81 (quin, J=6.87 Hz, 1H) 1.13 (d, J=7.02 Hz, 6H). MS (ESI) (m/z): 397.2 (M+H)$^+$.

Example 195

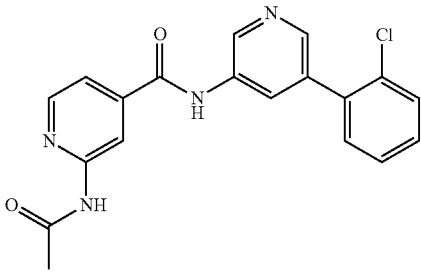 [SMILES: CC(=O)Nc1cc(C(=O)Nc2cncc(-c3ccccc3Cl)c2)ccn1]

N-(5-(2-chlorophenyl)pyridin-3-yl)-2-isobutyramidoisonicotinamide $^1$H NMR (500 MHz, DMSO-d$_6$) δ ppm 10.87 (s, 1H) 10.70 (s, 1H) 9.00 (d, J=2.14 Hz, 1H) 8.60 (s, 1H) 8.53 (d, J=4.88 Hz, 1H) 8.43 (d, J=1.83 Hz, 1H) 8.32 (t, J=1.98 Hz, 1H) 7.64-7.68 (m, 1H) 7.59 (dd, J=5.19, 1.22 Hz, 1H) 7.47-7.55 (m, 3H) 2.81 (quin, J=6.79 Hz, 1H) 1.13 (d, J=6.71 Hz, 6H). MS (ESI) (m/z): 395.1 (M+H)$^+$.

Example 209

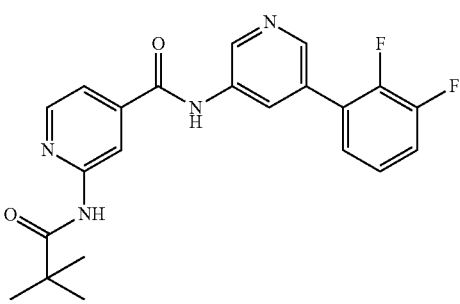 [SMILES: CC(C)(C)C(=O)Nc1cc(C(=O)Nc2cncc(-c3cccc(F)c3F)c2)ccn1]

N-(5-(2,3-difluorophenyl)pyridin-3-yl)-2-pivalamidoisonicotinamide $^1$H NMR (500 MHz, DMSO-d$_6$) δ ppm 10.91 (br. s., 1H) 10.12 (s, 1H) 9.03 (d, J=2.44 Hz, 1H) 8.53-8.63 (m, 3H) 8.45 (s, 1H) 7.61-7.64 (m, 1H) 7.56 (q, J=8.24 Hz, 1H) 7.45-7.51 (m, 1H) 7.36-7.43 (m, 1H) 1.28 (s, 9H). MS (ESI) (m/z): 411.2 (M+H)$^+$.

Example 213

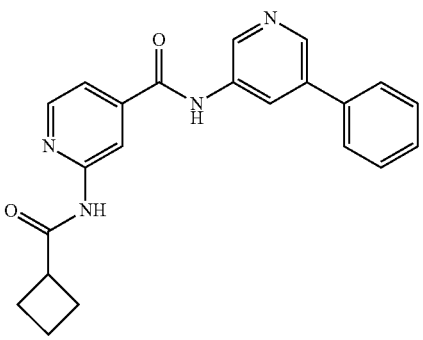 [SMILES: O=C(Nc1cncc(-c2ccccc2)c1)c1ccnc(NC(=O)C2CCC2)c1]

2-(cyclobutanecarboxamido)-N-(5-phenylpyridin-3-yl)isonicotinamide $^1$H NMR (400 MHz, dimethylformamide) δ ppm 11.00 (br. s., 1H) 10.45 (br. s., 1H) 9.12 (d, J=2.20 Hz, 1H) 8.82 (s, 1H) 8.74 (d, J=2.20 Hz, 1H) 8.65 (t, J=2.20 Hz, 1H) 8.52 (dd, J=5.14, 0.73 Hz, 1H) 7.79-7.84 (m, 3H) 7.71 (dd, J=5.14, 1.47 Hz, 1H) 7.59 (t, J=7.58 Hz, 2H) 7.48-7.54 (m, 1H) 3.10 (dt, J=3.85, 1.86 Hz, 1H) 2.57-2.61 (m, 1H) 2.31-2.43 (m, 2H) 2.16-2.28 (m, 2H) 1.96-2.08 (m, 1H). MS (ESI) (m/z): 373.2 (M+H)$^+$.

Example 214

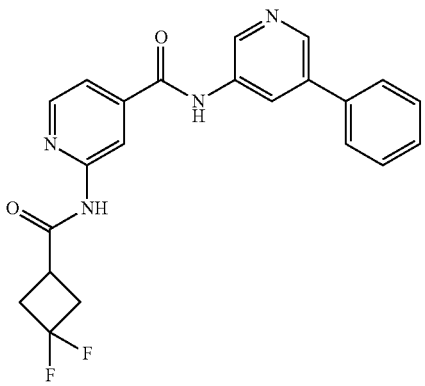 [SMILES: O=C(Nc1cncc(-c2ccccc2)c1)c1ccnc(NC(=O)C2CC(F)(F)C2)c1]

2-(3,3-difluorocyclobutanecarboxamido)-N-(5-phenylpyridin-3-yl)isonicotinamide $^1$H NMR (400 MHz, METHANOL-d$_4$) δ ppm 8.93 (d, J=2.20 Hz, 1H) 8.61-8.67 (m, 2H) 8.54 (t, 0.2.08 Hz, 2H) 7.69-7.76 (m, 2H) 7.61 (dd, J=5.14, 1.47 Hz, 1H) 7.51-7.58 (m, 2H) 7.43-7.50 (m, 1H) 3.19-3.30 (m, 1H) 2.77-3.02 (m, 4H). $^{19}$F NMR (376 MHz, METHANOL-d$_4$) ☐ ppm −87.13−−78.88 (m, 1F) −102.33−−96.40 (m, 1F). MS (ESI) (m/z): 409.2 (M+H)$^+$.

Example 232

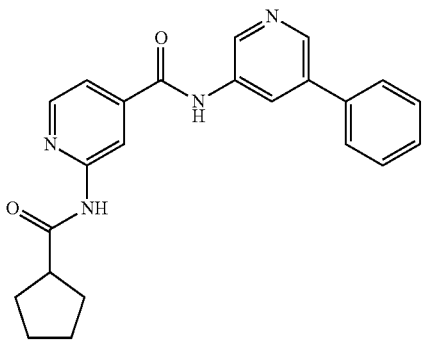 [SMILES: O=C(Nc1cncc(-c2ccccc2)c1)c1ccnc(NC(=O)C2CCCC2)c1]

2-(cyclopentanecarboxamido)-N-(5-phenylpyridin-3-yl)isonicotinamide $^1$H NMR (500 MHz, DMSO-d$_6$) δ ppm 10.93 (s, 1H) 10.73 (s, 1H) 9.03 (s, 1H) 8.75 (s, 1H) 8.62 (s, 1H) 8.51-8.58 (m, 2H) 7.73-7.79 (m, 2H) 7.54-7.63 (m, 3H) 7.46-7.52 (m, 1H) 2.99 (quin, J=7.86 Hz, 1H) 1.83-1.96 (m, 2H) 1.64-1.79 (m, 4H) 1.52-1.63 (m, 2H). MS (ESI) (m/z): 387.2 (M+H)$^+$.

Example 233

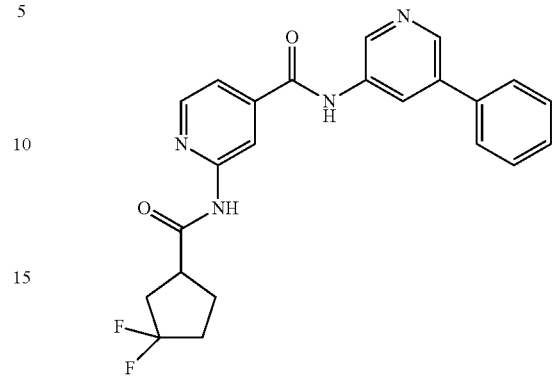

2-(3,3-difluorocyclopentanecarboxamido)-N-(5-phenylpyridin-3-yl)isonicotinamide $^1$H NMR (400 MHz, DMSO-d$_6$) δ ppm 10.94 (s, 1H) 10.88 (s, 1H) 9.03 (d, J=1.96 Hz, 1H) 8.76 (d, J=1.71 Hz, 1H) 8.61 (s, 1H) 8.54-8.58 (m, 2H) 7.75 (d, J=7.58 Hz, 2H) 7.63 (dd, J=5.14, 0.98 Hz, 1H) 7.53-7.59 (m, 2H) 7.46-7.52 (m, 1H) 3.31 (dt, J=16.69, 8.41 Hz, 1H) 2.31-2.45 (m, 2H) 2.05-2.28 (m, 3H) 1.88-2.00 (m, 1H). MS (ESI) (m/z): 423.1 (M+H)$^+$.

Example 234

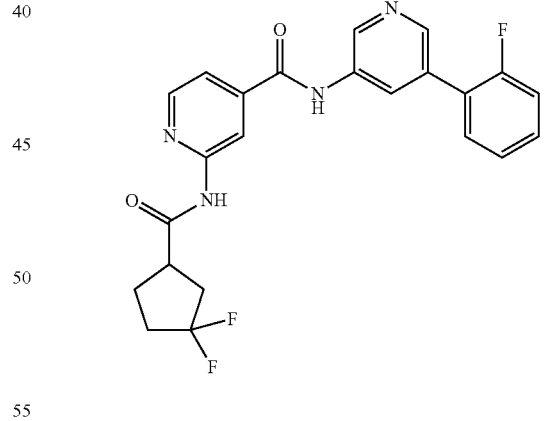

2-(3,3-difluorocyclopentanecarboxamido)-N-(5-(2-fluorophenyl)pyridin-3-yl)isonicotinamide $^1$H NMR (500 MHz, DMSO-d$_6$) δ ppm 10.89 (d, J=3.97 Hz, 2H) 9.01 (d, J=2.14 Hz, 1H) 8.59 (d, J=10.99 Hz, 2H) 8.56 (d, J=5.19 Hz, 1H) 8.44 (s, 1H) 7.60-7.68 (m, 2H) 7.49-7.57 (m, 1H) 7.34-7.46 (m, 2H) 3.25-3.34 (m, 1H) 2.34-2.44 (m, 2H) 2.07-2.29 (m, 3H) 1.90-2.00 (m, 1H). MS (ESI) (m/z): 441.3 (M+H)$^+$.

Example 235

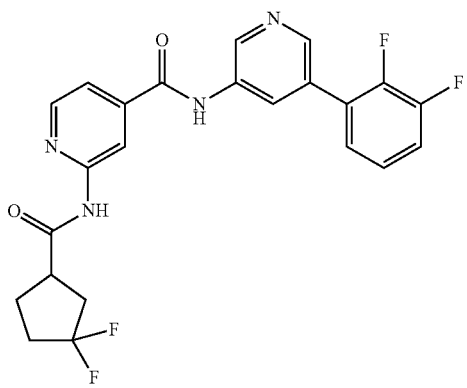 [SMILES: O=C(Nc1cncc(-c2cccc(F)c2F)c1)c1ccnc(NC(=O)C2CCC(F)(F)C2)c1]

2-(3,3-difluorocyclopentanecarboxamido)-N-(5-(2,3-difluorophenyl)pyridin-3-yl)isonicotinamide $^1$H NMR (500 MHz, DMSO-d$_6$) δ ppm 10.89 (s, 2H) 9.02 (d, J=2.44 Hz, 1H) 8.58-8.61 (m, 2H) 8.56 (d, J=5.19 Hz, 1H) 8.45 (s, 1H) 7.64 (dd, J=5.04, 1.37 Hz, 1H) 7.53-7.60 (m, 1H) 7.45-7.50 (m, 1H) 7.34-7.43 (m, 1H) 3.27-3.33 (m, 1H) 2.35-2.45 (m, 2H) 2.06-2.32 (m, 3H) 1.89-1.99 (m, 1H). MS (ESI) (m/z): 459.2 (M+H)$^+$.

Example 236

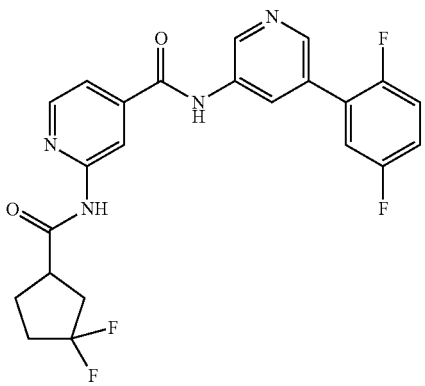 [SMILES: O=C(Nc1cncc(-c2cc(F)ccc2F)c1)c1ccnc(NC(=O)C2CCC(F)(F)C2)c1]

2-(3,3-difluorocyclopentanecarboxamido)-N-(5-(2,5-difluorophenyl)pyridin-3-yl)isonicotinamide $^1$H NMR (500 MHz, DMSO-d$_6$) δ ppm 10.88 (s, 2H) 9.01 (d, J=2.44 Hz, 1H) 8.60 (s, 1H) 8.57 (s, 1H) 8.55 (d, J=4.88 Hz, 1H) 8.44 (d, J=1.53 Hz, 1H) 7.64 (dd, J=5.19, 1.53 Hz, 1H) 7.57 (ddd, J=9.08, 6.03, 3.20 Hz, 1H) 7.47 (td, J=9.54, 4.42 Hz, 1H) 7.35-7.40 (m, 1H) 3.30 (d, J=8.24 Hz, 1H) 2.34-2.45 (m, 2H) 2.04-2.30 (m, 3H) 1.90-2.00 (m, 1H). MS (ESI) (m/z): 459.3 (M+H)$^+$.

Example 237

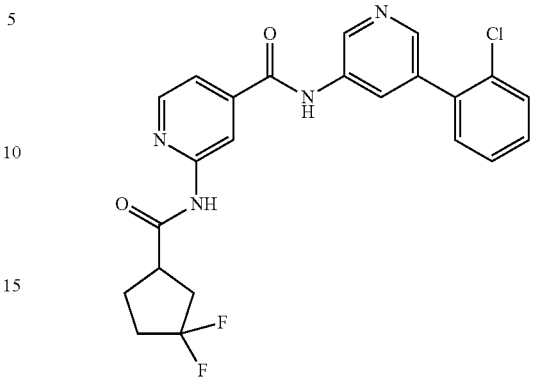

N-(5-(2-chlorophenyl)pyridin-3-yl)-2-(3,3-difluoro-cyclopentanecarboxamido)isonicotinamide $^1$H NMR (500 MHz, DMSO-d$_6$) δ ppm 10.89 (s, 2H) 9.00 (d, J=2.14 Hz, 1H) 8.59 (s, 1H) 8.55 (d, J=5.19 Hz, 1H) 8.43 (d, J=2.14 Hz, 1H) 8.32 (t, J=1.98 Hz, 1H) 7.60-7.69 (m, 2H) 7.45-7.57 (m, 3H) 3.23-3.32 (m, 1H) 2.34-2.45 (m, 2H) 2.06-2.28 (m, 3H) 1.88-2.00 (m, 1H). MS (ESI) (m/z): 457.2 (M+H)$^+$.

Example 107

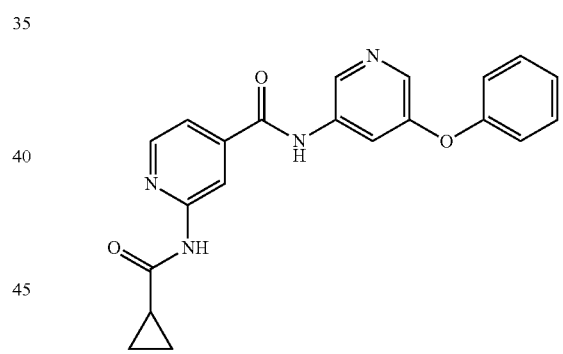

2-(cyclopropanecarboxamido)-N-(5-phenoxypyridin-3-yl)isonicotinamide

To a solution of N-(5-bromopyridin-3-yl)-2-(cyclopropanecarboxamido)isonicotinamide (30 mg, 0.083 mmol) and phenol (15.6 mg, 0.166 mmol) in dimethylformamide (1 mL) was added copper (I) iodide (3.16 mg, 0.017 mmol) and 2-(dimethylamino)acetic acid hydrochloride (6.96 mg, 0.050 mmol). The mixture was stirred at 100° C. for 5 hours. The mixture was partitioned between 1N HCl and ethyl acetate. The organic layer was washed with water, brine and dried over sodium sulfate. The crude material was purified via preparative LC using a C18 column and eluting with acetonitrile/20-mM ammonium acetate. $^1$H NMR (500 MHz, DMSO-d$_6$) δ ppm 11.04 (s, 1H) 10.78 (br. s., 1H) 8.77 (d, J=1.83 Hz, 1H) 8.48-8.54 (m, 2H) 8.19 (d, J=2.75 Hz, 1H) 7.86 (t, J=2.29 Hz, 1H) 7.52-7.55 (m, 1H) 7.46-7.50 (m, 2H) 7.22-7.27 (m, 1H) 7.14-7.18 (m, 2H) 2.01-2.09 (m, 1H) 0.83-0.88 (m, 4H). MS (ESI) (m/z): 375.2 (M+H)+.

Example 108

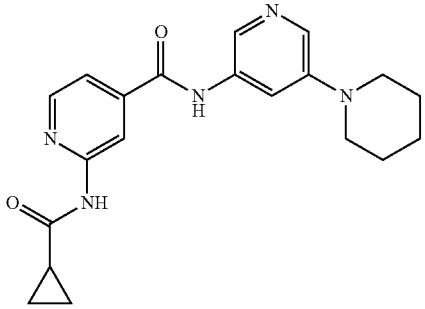 [SMILES: O=C(Nc1cncc(N2CCCCC2)c1)c1ccnc(NC(=O)C2CC2)c1]

2-(cyclopropanecarboxamido)-N-(5-(piperidin-1-yl)pyridin-3-yl)isonicotinamide

A mixture of N-(5-bromopyridin-3-yl)-2-(cyclopropanecarboxamido)isonicotinamide (30.0 mg, 0.083 mmol), piperidine (11 µl, 0.11 mmol), sodium tert-butoxide (12.0 mg, 0.125 mmol), 2-dicyclohexylphosphino-2',6'-di-i-propoxy-1,1'-biphenyl (3.88 mg, 8.31 µmol) and PdOAc$_2$ (1.865 mg, 8.31 µmol) in tetrahydrofuran (1 mL) under nitrogen was heated at 85° C. for 24 h. The mixture was diluted with ethyl acetate and water. The organic layer was washed with brine and dried over sodium sulfate. The crude material was purified via preparative LC using a C18 column, and eluting with methanol/0.01% TFA in water, to give the desired product (1.4 mg, 3.45 µmol, 4.1% yield). MS (ESI) (m/z): 366.2 (M+H)+.

Example 109

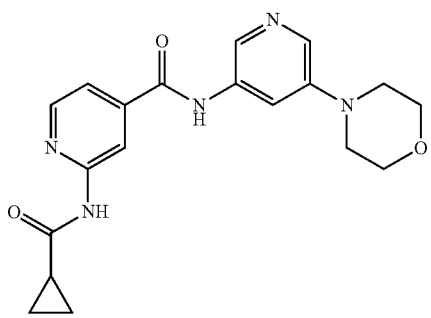 [SMILES: O=C(Nc1cncc(N2CCOCC2)c1)c1ccnc(NC(=O)C2CC2)c1]

2-(cyclopropanecarboxamido)-N-(5-morpholinopyridin-3-yl)isonicotinamide

MS (ESI) (m/z): 368.3 (M+H)+.

Example 118

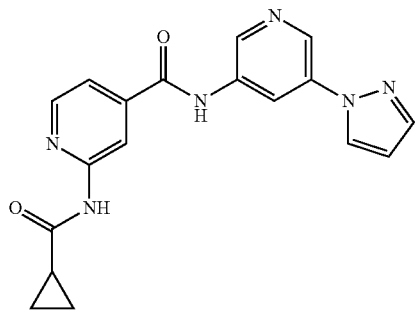 [SMILES: O=C(Nc1cncc(-n2cccn2)c1)c1ccnc(NC(=O)C2CC2)c1]

N-(5-(1H-pyrazol-1-yl)pyridin-3-yl)-2-(cyclopropanecarboxamido)isonicotinamide

To an oven-dried microwave vial was added N-(4-(5-bromophenyl)pyridin-3-yl)-2-(cyclopropanecarboxamido)isonicotinamide (0.05 g, 0.138 mmol), 1H-pyrazole (0.011 g, 0.166 mmol), potassium carbonate (0.038 g, 0.277 mmol) and copper (I) iodide (15 mg, 0.079 mmol). The system was degassed and flushed with nitrogen (3×). Then, 2,2,6,6-tetramethylheptane-3,5-dione (0.040 ml, 0.194 mmol) and dimethylformamide (1 mL) were added and then the reaction mixture was degassed again and flushed with nitrogen (3×). The vial was sealed heated in an oil bath at 110° C. for 20 h. The mixture was cooled, diluted with methylene chloride, and then washed with ammonium hydroxide followed by brine, and then dried over sodium sulfate. The crude product was purified using a preparative HPLC to give N-(5-(1H-pyrazol-1-yl)pyridin-3-yl)-2-(cyclopropanecarboxamido)isonicotinamide (12.7 mg, 0.035 mmol, 25% yield). $^1$H NMR (400 MHz, DMSO-d$_6$) δ ppm 11.04 (s, 1H) 10.90 (br. s., 1H) 8.88 (dd, =3.55, 2.32 Hz, 2H) 8.74 (t, J=2.20 Hz, 1H) 8.61 (d, J=2.45 Hz, 1H) 8.57 (s, 1H) 8.54 (d, J=5.14 Hz, 1H) 7.85 (d, J=1.71 Hz, 1H) 7.60 (dd, J=5.01, 1.59 Hz, 1H) 6.55-6.67 (m, 1H) 2.01-2.11 (m, 1H) 0.81-0.91 (m, 4H). MS (ESI) (m/z): 349.2 (M+H)+.

Example 119

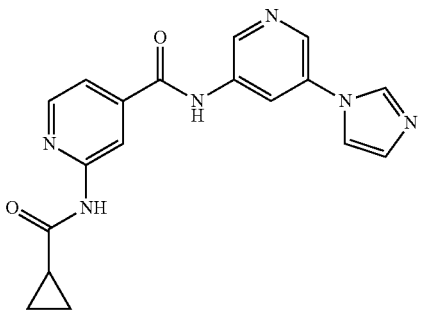 [SMILES: O=C(Nc1cncc(-n2ccnc2)c1)c1ccnc(NC(=O)C2CC2)c1]

N-(5-(1H-imidazol-1-yl)pyridin-3-yl)-2-(cyclopropanecarboxamido)isonicotinamide $^1$H NMR (400 MHz, DMSO-d$_6$) δ ppm 11.09 (d, J=7.82 Hz, 2H) 9.56 (br. s., 1H) 8.97 (d, J=1.71 Hz, 1H) 8.80 (d, J=1.96 Hz, 1H) 8.68 (t, J=2.20 Hz, 1H) 8.51-8.60 (m, 2H) 8.28 (br. s., 1H) 7.88 (br. s., 1H) 7.58 (dd, J=5.14, 1.47 Hz, 1H) 1.99-2.14 (m, 1H) 0.86 (d, J6.11 Hz, 4H). MS (ESI) (m/z): 349.2 (M+H)$^+$.

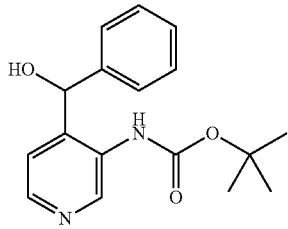 [SMILES: CC(C)(C)OC(=O)Nc1cnccc1C(O)c1ccccc1]

tert-butyl
(4-(hydroxy(phenyl)methyl)pyridin-3-yl)carbamate

To a solution of tert-butyl pyridin-3-ylcarbamate (0.5 g, 2.57 mmol) in tetrahydrofuran (10 mL) at −78° C. was added n-butyllithium, (1.6 M in hexanes, 4.02 mL, 6.44 mmol), dropwise over 1 minute. The reaction was stirred at −78° C. for 15 minutes and then at 0° C. for 1 hr. The reaction was cooled down to −78° C. and then benzaldehyde (0.393 mL, 3.86 mmol) in tetrahydrofuran (1) was added dropwise. The reaction was allowed to warm to rt and stirred overnight. Water was added and then the mixture was extracted with ethyl acetate. The organic extracts were washed with brine, dried over sodium sulfate and concentrated in vacuo. The crude product was purified by flash column chromatography using silica gel, eluting with 0-80% ethyl acetate/hexanes, to give the desired product (0.24 g, 0.799 mmol, 31% yield). $^1$H NMR (400 MHz, Chloroform-d) δ ppm 9.03 (s, 1H) 8.31 (d, J=4.89 Hz, 1H) 7.35-7.42 (m, 6H) 7.03 (d, J=5.14 Hz, 1H) 5.95 (d, J=2.69 Hz, 1H) 3.06 (br. s., 1H) 1.51 (s, 9H). MS (ESI) (m/z): 301.1 (M+H)$^+$.

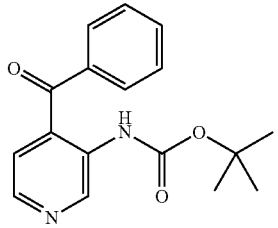 [SMILES: CC(C)(C)OC(=O)Nc1cnccc1C(=O)c1ccccc1]

tert-butyl (4-benzoylpyridin-3-yl)carbamate

Solid manganese dioxide (0.289 g, 3.33 mmol) under nitrogen at room temperature was treated with tert-butyl (4-(hydroxy(phenyl)methyl)pyridin-3-yl)carbamate (0.1 g, 0.333 mmol) in methylene chloride (2 mL). The mixture was stirred overnight at rt, and then filtered through celite. The filtrate was concentrated in vacuo to give the desired product (94 mg, 0.315 mmol, 95% yield). $^1$H NMR (400 MHz, Chloroform-d) δ ppm 9.69 (s, 1H) 9.15 (br. s., 1H) 8.41 (d, J=4.89 Hz, 1H) 7.75-7.83 (m, 2H) 7.63-7.72 (m, 1H) 7.48-7.59 (m, 2H) 7.31-7.36 (m, 1H) 1.55 (s, 9H). MS (ESI) (m/z): 299.1 (M+H)$^+$.

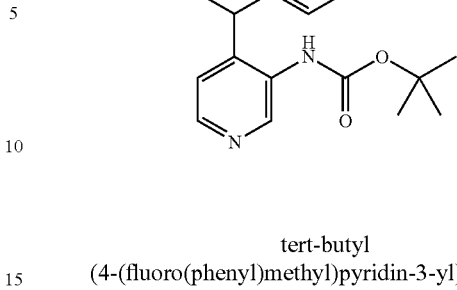

tert-butyl
(4-(fluoro(phenyl)methyl)pyridin-3-yl)carbamate tert-butyl (4-(hydroxy(phenyl)methyl)pyridin-3-yl)carbamate (0.1 g, 0.333 mmol) in methylene chloride (1.5 mL) at 0° C. was added bis(2-methoxyethyl)aminosulfur trifluoride (0.092 mL, 0.499 mmol). The reaction was allowed to warm to rt and stirred at rt for 3 h. Saturated sodium bicarbonate was added and the mixture was extracted with dichloromethane. The organic extracts were dried over sodium sulfate, filtered and evaporated. The crude product was purified by flash column chromatography using silica gel, eluting with 0-50% ethyl acetate/hexanes, to the desired product (31 mg, 0.103 mmol, 31% yield). $^1$H NMR (400 MHz, Chloroform-d) δ ppm 9.05 (s, 1H) 8.42 (d, J=5.14 Hz, 1H) 7.41-7.47 (m, 3H) 7.34 (dd, J=5.38, 2.45 Hz, 2H) 7.16 (d, J=4.89 Hz, 1H) 6.51-6.67 (m, 1H) 6.46 (br. s., 1H) 1.49 (s, 9H). MS (ESI) (m/z): 303 (M+H)$^+$.

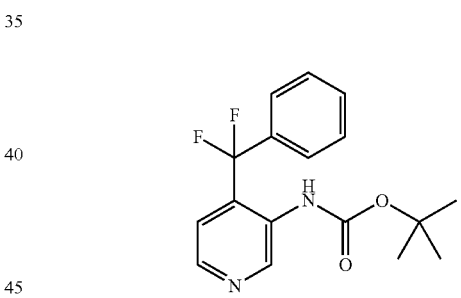

tert-butyl
(4-(difluoro(phenyl)methyl)pyridin-3-yl)carbamate

To a solution of tert-butyl (4-benzoylpyridin-3-yl)carbamate (0.09 g, 0.302 mmol) in methylene chloride (1 mL) at 0° C. was added bis(2-methoxyethyl)aminosulfur trifluoride (0.167 ml, 0.905 mmol) resulting in a yellow solution. The reaction was allowed to warm to room temperature and stirred overnight. Saturated sodium bicarbonate was then added and the product was extracted with dichloromethane (2×). The organic layer was separated and dried over sodium sulfate. The crude product was purified by flash column chromatography using silica gel, eluting with 0-15% dichloromethane/methanol, to give the desired product (0.046 g, 0.144 mmol, 48% yield). $^1$H NMR (400 MHz, Chloroform-d) δ ppm 9.22 (s, 1H) 8.47 (d, J=5.14 Hz, 1H) 7.43-7.51 (m, 5H) 7.38 (d, J=5.14 Hz, 1H) 6.64 (br. s., 1H) 1.42 (s, 9H). MS (ESI) (m/z): 321.0 (M+H)$^+$.

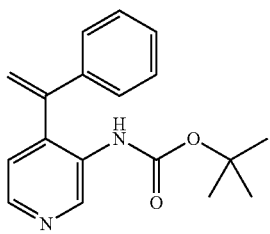 [SMILES: C=C(c1ccccc1)c1ccncc1NC(=O)OC(C)(C)C]

tert-butyl (4-(1-phenylvinyl)pyridin-3-yl)carbamate

To a solution of methyl triphenylphosphonium iodide (0.677 g, 1.676 mmol) in tetrahydrofuran (5 mL) at 0° C. was added n-butyllithium (1.6 M in hexanes, 1.047 mL, 1.676 mmol). The mixture was stirred at 0° C. for 10 min and then at rt for 30 min. The solution was re-cooled to 0° C., and a solution of tert-butyl (4-benzoylpyridin-3-yl)carbamate (0.2 g, 0.670 mmol) in tetrahydrofuran (2 mL) was added slowly. The reaction was stirred at 0° C. for 15 min. and then at rt for 1.0 h. Then it was diluted with ethyl acetate/diethyl ether, quenched with saturated ammonium chloride. The organic layer was washed with brine and dried over sodium sulfate. The crude product was purified by flash column chromatography using silica gel, eluting with 0-50% ethyl acetate/hexanes, to give the desired product (0.12 g, 0.405 mmol, 60% yield). $^1$H NMR (400 MHz, Chloroform-d) δ ppm 9.26 (s, 1H) 8.37 (d, J=4.89 Hz, 1H) 7.36-7.39 (m, 3H) 7.29-7.32 (m, 2H) 7.14 (dd, J=4.89, 0.49 Hz, 1H) 6.27 (br. s., 1H) 5.97 (d, J=0.73 Hz, 1H) 5.42 (d, J=0.49 Hz, 1H) 1.59 (s, 9H). MS (ESI) (m/z): 297.1 (M+H)$^+$.

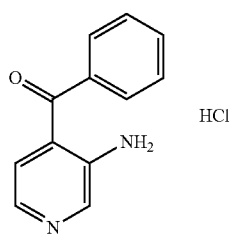 [SMILES: Nc1cnccc1C(=O)c1ccccc1 ; Cl]

(3-aminopyridin-4-yl)(phenyl)methanone Hydrochloride

To tert-butyl (4-benzoylpyridin-3-yl)carbamate (0.09 g, 0.302 mmol) in methylene chloride (1 mL) was added HCl, 4M dioxane (0.377 mL, 1.508 mmol). The reaction was stirred at rt overnight. The mixture was concentrated in vacuo to give the desired product (0.07 g, 0.298 mmol, 99% yield). $^1$H NMR (400 MHz, DMSO-d$_6$) δ ppm 8.34 (s, 1H) 7.87 (d, J=5.38 Hz, 1H) 7.66-7.74 (m, 3H) 7.54-7.61 (m, 2H) 7.33 (d, J=4.40 Hz, 1H) 3.56 (d, J=16.63 Hz, 2H). MS (ESI) (m/z): 199.1 (M+H)$^+$.

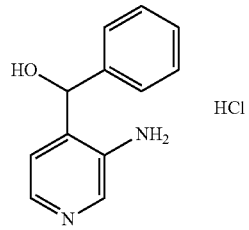 [SMILES: Nc1cnccc1C(O)c1ccccc1 ; Cl]

(3-aminopyridin-4-yl)(phenyl)methanol Hydrochloride

MS (ESI) (m/z): 201.1 (M+H)$^+$.

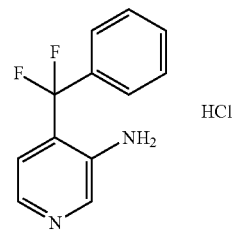 [SMILES: Nc1cnccc1C(F)(F)c1ccccc1 ; Cl]

4-(difluoro(phenyl)methyl)pyridin-3-amine Hydrochloride

MS (ESI) (m/z): 221 (M+H)$^+$.

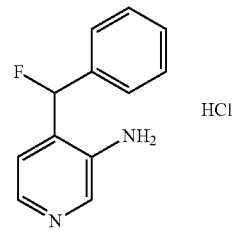 [SMILES: Nc1cnccc1C(F)c1ccccc1 ; Cl]

4-(fluoro(phenyl)methyl)pyridin-3-amine Hydrochloride $^1$H NMR (400 MHz, DMSO-d$_6$) δ ppm 8.10 (s, 1H) 8.06 (d, J=5.62 Hz, 1H) 7.65 (d, J=5.14 Hz, 1H) 7.43-7.53 (m, 5H) 6.83 (d, J=50.86 Hz, 1H) 6.19 (br. s., 2H).

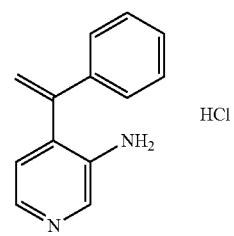

4-(1-phenylvinyl)pyridin-3-amine Hydrochloride

MS (ESI) (m/z): 197.1 (M+H)$^+$.

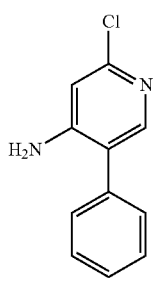

2-chloro-5-phenylpyridin-4-amine

To a mixture of 5-bromo-2-chloropyridin-4-amine (0.2 g, 0.964 mmol) and phenylboronic acid (0.141 g, 1.157 mmol) was added dioxane (3 mL). The reaction was stirred at rt until the mixture became homogeneous, and then PdCl2 (dppf)-methylene chloride adduct (0.039 g, 0.048 mmol) was added. The flask was degassed and flushed with nitrogen and then aqueous sodium carbonate, (2 M, 1.446 mL, 2.89 mmol) was added dropwise. The flask was degassed and sealed and then heated at 100° C. for 2 h. Saturated ammonium chloride and ethyl acetate was added. The organic layer was separated, washed with water and brine and dried over sodium sulfate. The crude product was purified by flash column chromatography using silica gel, eluting with 0-15% dichloromethane/methanol, to give the desired product (0.17 g, 0.831 mmol, 86% yield). MS (ESI) (m/z): 205.1 (M+H)+.

Example 196

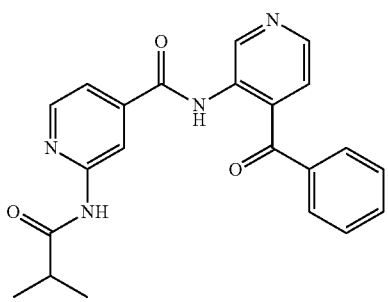 [SMILES: CC(C)C(=O)Nc1cc(C(=O)Nc2cnccc2C(=O)c2ccccc2)ccn1]

N-(4-benzoylpyridin-3-yl)-2-isobutyramidoisonicotinamide

To a solution of 2-isobutyramidoisonicotinic acid (0.062 g, 0.298 mmol) and (3-aminopyridin-4-yl)(phenyl)methanone hydrochloride (0.07 g, 0.298 mmol) in dimethylformamide (3 mL) was added DIEA (0.26 mL, 1.49 mmol) followed by 1-propanephosphonic acid cyclic anhydride (0.871 mL, 1.491 mmol). The reaction was stirred at rt overnight, and then diluted with ethyl acetate and water. The organic extracts were washed with brine, dried over sodium sulfate and concentrated in vacuo. The crude product was purified by flash column chromatography using silica gel, eluting with 0-80% ethyl acetate/hexanes, to give the desired product (0.05 g, 0.129 mmol, 43.2% yield). $^1$H NMR (500 MHz, DMSO-d$_6$) δ ppm 10.93 (br. s., 1H) 10.62 (s, 1H) 8.77 (s, 1H) 8.61 (d, J=4.88 Hz, 1H) 8.40 (d, J=5.19 Hz, 1H) 8.36 (s, 1H) 7.71-7.80 (m, 2H) 7.60-7.67 (m, 1H) 7.48-7.55 (m, 2H) 7.45 (d, J=4.88 Hz, 1H) 7.23 (dd, J=5.19, 1.53 Hz, 1H) 2.77 (quin, J=6.79 Hz, 1H) 1.10 (d, J=6.71 Hz, 6H). MS (ESI) (m/z): 389.2 (M+H)+.

Example 197

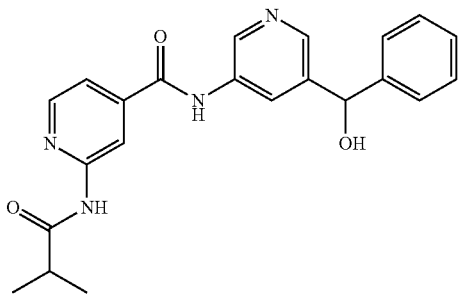 [SMILES: CC(C)C(=O)Nc1cc(C(=O)Nc2cncc(C(O)c3ccccc3)c2)ccn1]

N-(5-(hydroxy(phenyl)methyl)pyridin-3-yl)-2-isobutyramidoisonicotinamide $^1$H NMR (500 MHz, Methanol-d$_4$) δ ppm 8.98 (s, 1H) 8.53 (s, 1H) 8.45 (d, J=4.88 Hz, 2H) 7.64 (d, J=5.19 Hz, 1H) 7.23-7.37 (m, 6H) 6.05 (s, 1H) 2.76 (quin, J=6.87 Hz, 1H) 1.25 (dd, J=6.71, 2.44 Hz, 6H). MS (ESI) (m/z): 391.3 (M+H)+.

Example 198

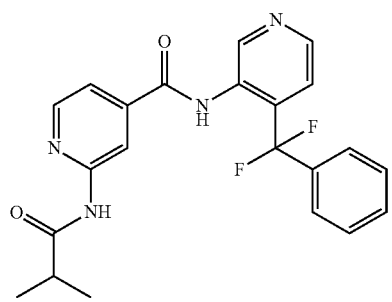 [SMILES: CC(C)C(=O)Nc1cc(C(=O)Nc2cnccc2C(F)(F)c2ccccc2)ccn1]

N-(4-(difluoro(phenyl)methyl)pyridin-3-yl)-2-isobutyramidoisonicotinamide

MS (ESI) (m/z): 411.2 (M+H)+.

Example 199

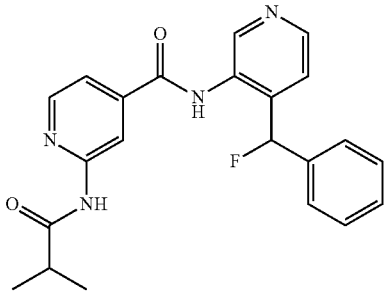 [SMILES: CC(C)C(=O)Nc1cc(C(=O)Nc2cnccc2C(F)c2ccccc2)ccn1]

N-(4-(fluoro(phenyl)methyl)pyridin-3-yl)-2-isobutyramidoisonicotinamide

¹H NMR (500 MHz, DMSO-d₆) δ ppm 10.67 (s, 1H) 10.42 (br. s., 1H) 8.62 (d, J=5.19 Hz, 1H) 8.56 (s, 1H) 8.50 (s, 1H) 8.47 (d, J=4.88 Hz, 1H) 7.66 (d, J=5.19 Hz, 1H) 7.26-7.37 (m, 6H) 6.90 (d, J=48.22 Hz, 1H) 2.80 (quin, J=6.79 Hz, 1H) 1.13 (d, J=7.02 Hz, 6H). MS (ESI) (m/z): 393.2 (M+H)⁺.

Example 200

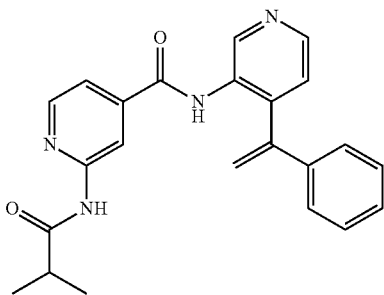 [SMILES: C=C(c1ccccc1)c1ccncc1NC(=O)c1ccnc(NC(=O)C(C)C)c1]

2-Isobutyramido-N-(4-(1-phenylvinyl)pyridine-3-yl)isonicotinamide

¹H NMR (500 MHz, DMSO-d₆) δ ppm 10.56 (s, 1H) 10.10 (br. s., 1H) 8.63 (s, 1H) 8.53 (d, J=5.19 Hz, 1H) 8.27-8.39 (m, 2H) 7.35 (d, J=4.88 Hz, 1H) 7.19-7.29 (m, 5H) 6.98 (dd, J=5.19, 1.53 Hz, 1H) 5.81 (s, 1H) 5.50 (s, 1H) 2.72-2.81 (m, 1H) 1.11 (d, J=7.02 Hz, 6H). MS (ESI) (m/z): 387.2 (M+H)⁺.

Example 201

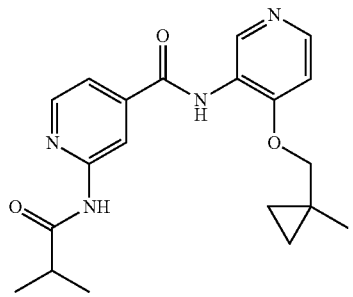 [SMILES: CC(C)C(=O)Nc1cc(C(=O)Nc2cnccc2OCC2(C)CC2)ccn1]

2-isobutyramido-N-(4-((1-methylcyclopropyl)methoxy)pyridin-3-yl)isonicotinamide

¹H NMR (500 MHz, DMSO-d₆) δ ppm 10.64 (br. s., 1H) 9.98 (br. s., 1H) 8.52-8.59 (m, 2H) 8.50 (br. s., 1H) 8.33 (br. s., 1H) 7.53 (br. s., 1H) 7.11 (br. s., 1H) 3.91 (br. s., 2H) 2.78 (d, J=5.49 Hz, 1H) 1.02-1.19 (m, 9H) 0.53 (br. s., 2H) 0.36 (br. s., 2H). MS (ESI) (m/z): 369.3 (M+H)⁺.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound of formula I

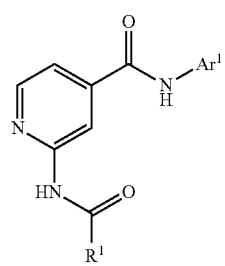

where:

R¹ is alkyl, haloalkyl, cycloalkyl, halocycloalkyl alkylcycloalkyl, dialkylcycloalkyl, phenylcycloalkyl, hydroxycycloalkyl, or ketocycloalkyl;

R² is hydrogen or alkyl;

R³ is hydrogen or alkyl;

or N(R²)(R³) taken together is azetidinyl, pyrrolidinyl, piperidinyl, piperazinyl, morpholinyl, or azabicycloheptane, and is substituted with 0-4 halo or alkyl substituents;

Ar¹ is 3-pyridinyl substituted with 0-3 substituents selected from cyano, halo, alkyl, haloalkyl, hydroxyalkyl, (hydroxyl)haloalkyl, alkoxyalkyl, (N(R²)(R³))alkyl, benzyl, alkenyl, cycloalkyl, hydroxy, alkoxy, haloalkoxy, (hydroxyl)alkoxy, (alkoxy)alkoxy, (cycloalkyl)alkoxy, phenoxy, alkylcarbonyl, (haloalkyl)carbonyl, phenylcarbonyl, alkoxycarbonyl, carboxy, aminocarbonyl, acetamido, N(R²)(R³) and Ar²; and Ar² is phenyl, naphthalenyl, pyrrolyl, furanyl, thienyl, pyrrazolyl, imidazolyl, thiazolyl, pyridinyl, pyrimidinyl, indolyl, benzofuranyl, benzothiophenyl, quinolinyl, and is substituted with 0-1 substituents selected from the group consisting of cyano, halo, alkyl, haloalkyl, alkoxy, haloalkoxy, alkylcarbonyl, and N(R²)(R³);

or a pharmaceutically acceptable salt thereof.

2. A compound of claim 1 selected from the group consisting of

143

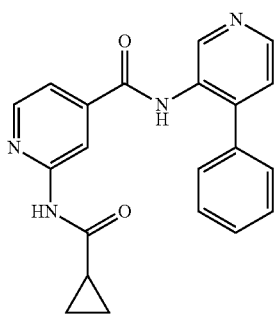 [SMILES: O=C(Nc1cnccc1-c1ccccc1)c1ccnc(NC(=O)C2CC2)c1]

18 2-(cyclopropanecarboxamido)-N-(4-phenylpyridin-3-yl)isonicotinamide;

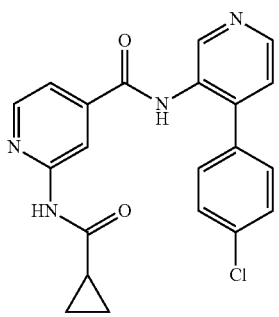 [SMILES: O=C(Nc1cnccc1-c1ccc(Cl)cc1)c1ccnc(NC(=O)C2CC2)c1]

N-(4-(4-chlorophenyl)pyridin-3-yl)-2-(cyclopropanecarboxamido)isonicotinamide;

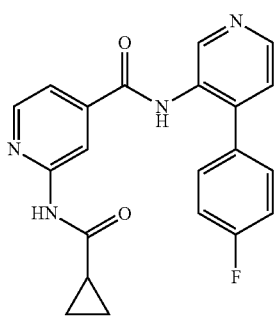 [SMILES: O=C(Nc1cnccc1-c1ccc(F)cc1)c1ccnc(NC(=O)C2CC2)c1]

2-(cyclopropanecarboxamido)-N-(4-(4-fluorophenyl)pyridin-3-yl)isonicotinamide;

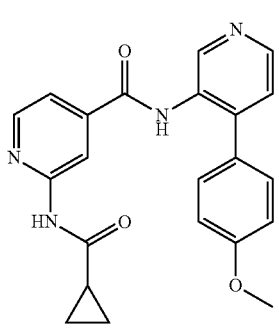 [SMILES: COc1ccc(-c2ccncc2NC(=O)c2ccnc(NC(=O)C3CC3)c2)cc1]

2-(cyclopropanecarboxamido)-N-(4-(4-methoxyphenyl)pyridin-3-yl)isonicotinamide;

144

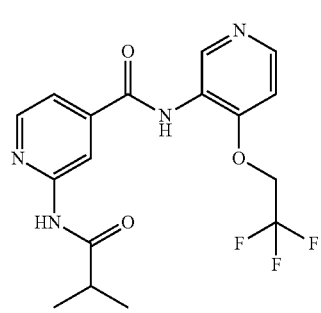

2-isobutyramido-N-(4-(2,2,2-trifluoroethoxy)pyridin-3-yl)isonicotinamide;

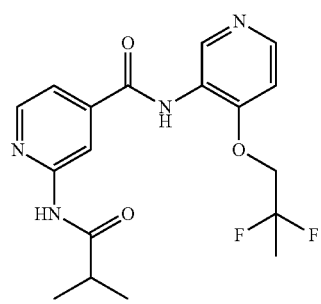 [SMILES: CC(C)C(=O)Nc1cc(C(=O)Nc2cnccc2OCC(C)(F)F)ccn1]

N-(4-(2,2-difluoropropoxy)pyridin-3-yl)-2-isobutyramidoisonicotinamide; and

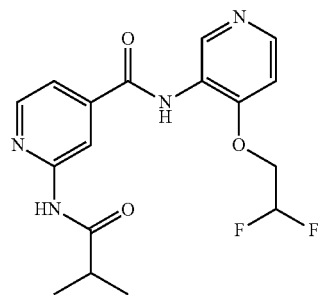 [SMILES: CC(C)C(=O)Nc1cc(C(=O)Nc2cnccc2OCC(F)F)ccn1]

N-(4-(2,2-difluoroethoxy)pyridin-3-yl)-2-isobutyramidoisonicotinamide;

or a pharmaceutically acceptable salt thereof.

3. A pharmaceutical composition comprising a compound of claim 1 or a pharmaceutically acceptable salt thereof and a pharmaceutically acceptable carrier.

* * * * *

UNITED STATES PATENT AND TRADEMARK OFFICE
CERTIFICATE OF CORRECTION

PATENT NO. : 9,809,573 B2
APPLICATION NO. : 15/033770
DATED : November 7, 2017
INVENTOR(S) : Luo et al.

Page 1 of 1

It is certified that error appears in the above-identified patent and that said Letters Patent is hereby corrected as shown below:

In the Claims

Claim 1, Column 142, Line 37:
After "halocycloalkyl" insert -- , --.

Claim 1, Column 142, Lines 58-59:
Delete "pyrrazolyl" and insert -- pyrazolyl --.

Claim 1, Column 142, Line 63:
Delete "and" and insert -- or --.

Signed and Sealed this
Twenty-third Day of October, 2018

Andrei Iancu
*Director of the United States Patent and Trademark Office*